US010466231B2

(12) United States Patent
Geisbert et al.

(10) Patent No.: US 10,466,231 B2
(45) Date of Patent: Nov. 5, 2019

(54) VARIANT ANGOLA MARBURG VIRUS

(71) Applicant: Board of Regents, The University of Texas System, Austin, TX (US)

(72) Inventors: Joan B. Geisbert, Galveston, TX (US); Chad E. Mire, Galveston, TX (US); Thomas W. Geisbert, Galveston, TX (US); Robert W. Cross, Galveston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 139 days.

(21) Appl. No.: 15/261,608

(22) Filed: Sep. 9, 2016

(65) Prior Publication Data

US 2017/0089884 A1    Mar. 30, 2017

Related U.S. Application Data

(60) Provisional application No. 62/217,402, filed on Sep. 11, 2015.

(51) Int. Cl.
*C12N 7/00*     (2006.01)
*G01N 33/50*    (2006.01)
*C12Q 1/70*     (2006.01)

(52) U.S. Cl.
CPC ........... *G01N 33/5008* (2013.01); *C12N 7/00* (2013.01); *C12Q 1/701* (2013.01); *C12N 2760/14121* (2013.01); *C12N 2760/14122* (2013.01); *C12N 2760/14221* (2013.01); *C12N 2760/14222* (2013.01); *C12Q 1/70* (2013.01); *C12Q 2600/156* (2013.01)

(58) Field of Classification Search
CPC ........................ C12N 7/00; C12N 2760/14122
See application file for complete search history.

(56) References Cited

PUBLICATIONS

Cross, R. W.,et al., 2015, Comparison of the Pathogenesis of the Angola and Ravn Strains of Marburg Virus in the Outbred Guinea Pig Model, J. Infect. Dis. 212(Suppl 2):S258-S270, published Sep. 1, 2015.*
Albarino, C.G., et al., "Development of a reverse genetics system to generate recombinant Marburg virus derived from a bat isolate." Virology (2013); 446:230-7.
Albarino, C.G., et al., "Recombinant Marburg viruses containing mutations in the IID region of VP35 prevent inhibition of Host immune responses." Virology (2014); 476C:85-91.
Alves, D.A., et al., "Aerosol exposure to the Angola strain of Marburg virus causes lethal viral hemorrhagic Fever in Cynomolgus macaques." Vet Pathol (2010); 47:831-51.
Bae, J.-P., "Role of High Mobility Group Box 1 in Inflammatory Disease: Focus on Sepsis." Arch Pharm Res (2012); 35:1511-23.
Bamberg, S., et al., "VP24 of Marburg Virus Influences Formation of Infectious Particles." J Virol (2005); 79:13421-33.
Bausch, D.G., et al., "Outbreak of Ebola virus disease in Guinea: where ecology meets economy." PLoS Negl Trop Dis (2014); 8:e3056.
Bray, M., et al., "A mouse model for evaluation of prophylaxis and therapy of Ebola hemorrhagic fever." J Infect Dis 1998; 178:651-61.
Bray, M., et al., "Haematological, biochemical and coagulation changes in mice, guinea-pigs and monkeys infected with a mouse-adapted variant of Ebola Zaire virus." J Comp Pathol (2001); 125:243-53.
Bray, M., et al., "Ebola hemorrhagic fever and septic shock." J Infect Dis (2003); 188:1613-7.
Bruegel, M., et al., "Sepsis-associated changes of the arachidonic acid metabolism and their diagnostic potential in septic patients." Crit Care Med (2012); 40:1478-86.
Colebunders, R., et al., "Marburg hemorrhagic fever in Durba and Watsa, Democratic Republic of the Congo: clinical documentation, features of illness, and treatment" J Infect Dis (2007); 196(suppl 2):S148-53.
Connolly, B.M., et al., "Pathogenesis of experimental Ebola virus infection in guinea pigs." J Infect Dis (1999); 179 (suppl 1): S203-17.
Daddario-DiCaprio, K.M., et al., "Cross-protection against Marburg virus strains by using a live, attenuated recombinant vaccine." J Virol (2006); 80:9659-66.
Davis, K.J., et al., "Pathology of experimental Ebola virus infection in African green monkeys. Involvement of fibroblastic reticular cells." Arch Pathol Lab Med (1997); 121:805-19.
Ebihara, H., et al., "Molecular determinants of Ebola virus virulence in mice." PLoS Pathog (2006); 2:e73.
Ebihara, H., et al., "In vitro and in vivo characterization of recombinant Ebola viruses expressing enhanced green fluorescent protein." J Infect Dis (2007); 196(suppl 2): S313-22.
Ebihara H., et al., "Host response dynamics following lethal infection of rhesus macaques with Zaire ebolavirus". J Infect Dis (2011); 204(suppl 3):S991-9.
Ebihara, H., et al., "A Syrian golden hamster model recapitulating Ebola hemorrhagic fever." J Infect Dis (2013); 207:306-18.
"Ebola hemorrhagic fever in Zaire, 1976" Bull World Health Organ (1978); 56:271-93.
Edwards, M.R., et al., "The Marburg virus VP24 protein interacts with Keap1 to activate the cytoprotective antioxidant response pathway." Cell Rep (2014); 6:1017-25.

(Continued)

*Primary Examiner* — Jeffrey S Parkin
(74) *Attorney, Agent, or Firm* — Edwin S. Flores; Chalker Flores, LLP

(57) ABSTRACT

The present invention includes methods of making, and compositions comprising, a uniformly lethal filovirus for outbred small mammals by mutation of the viral genome through serial passages in a small mammal, the method comprising the steps of: obtaining a filovirus strain from a human subject; passing the filovirus strain one or more times by intramuscular injection of one or more filovirus infected tissues into an inbred small mammal until uniform lethality is obtained; passing the filovirus strain in one or more human cell lines; passing the filovirus strain one or more times by intraperitoneal injection of one or more filovirus infected tissues into an outbred small mammal until uniform lethality is obtained; and isolating the uniformly lethal filovirus obtained thereby.

1 Claim, 25 Drawing Sheets

(56) References Cited

PUBLICATIONS

Escudero-Perez, B., et al., "Shed GP of Ebola virus triggers immune activation and increased vascular permeability." PLoS Pathog (2014); 10:e1004509.

Falzarano, D., et al., "Structure-function analysis of the soluble glycoprotein, sGP, of Ebola virus." ChemBioChem (2006); 7:1605-11.

Feldmann, H., et al., The glycoproteins of Marburg and Ebola virus and their potential roles in pathogenesis. Arch Virol Suppl (1999); 15:159-69.

Feuerstein, G., et al., "Prostaglandins, leukotrienes, and platelet-activating factor in shock." Annu Rev Pharmacol Toxicol (1987); 27: 301-13.

Fiddler, R.N., "Collaborative study of modified AOAC method of analysis for nitrite in meat and meat products." J Assoc Off Anal Chem (1977); 60:594-9.

Fisher-Hoch, SP., et al., "Pathophysiology of shock and hemorrhage in a fulminating viral infection (Ebola)." J Infect Dis (1985); 152:887-94.

Geisbert, T.W., et al., "Apoptosis induced in vitro and in vivo during infection by Ebola and Marburg viruses." Lab Invest (2000); 80:171-86.

Geisbert, T.W., et al., "Pathogenesis of Ebola hemorrhagic fever in Cynomolgus macaques: evidence that dendritic cells are early and sustained targets of infection." Am J Pathol (2003); 163:2347-70.

Geisbert, T.W., et al., "Pathogenesis of Ebola hemorrhagic fever in primate models: evidence that hemorrhage is not a direct effect of virus-induced cytolysis of endothelial cells." Am J Pathol (2003); 163:2371-82.

Geisbert, T.W., et al., "Towards a vaccine against Ebola virus. Expert Rev Vaccines" (2003); 2:777-89.

Geisbert, T.W., et al., "Postexposure protection of guinea pigs against a lethal Ebola virus challenge is conferred by RNA interference." J Infect Dis (2006); 193:1650-7.

Geisbert, T.W., et al., "Marburg virus Angola infection of rhesus macaques: pathogenesis and treatment with recombinant nematode anticoagulant protein c2." J Infect Dis (2007); 196(suppl 2):S372-81.

Geisbert, T.W., et al., "Postexposure protection of non-human primates against a lethal Ebola virus challenge with RNA interference: a proof-of-concept study." Lancet (2010); 375:1896-905.

Gibb, TR., et al., "Pathogenesis of experimental Ebola Zaire virus infection in BALB/c mice." J Comp Pathol (2001); 125:233-42.

Hatada, T., et al., "Plasma concentrations and importance of High Mobility Group Box protein in the prognosis of organ failure in patients with disseminated intravascular coagulation." Thromb Haemost (2005); 94:975-9.

Hutchinson, K.L., et al., "Cytokine and chemokine expression in humans infected with Sudan Ebola virus." J Infect Dis (2007); 196(suppl 2): S357-63.

Johnson, E.D., et al., "Characterization of a new Marburg virus isolated from a 1987 fatal case in Kenya." Arch Virol Suppl (1996); 11:101-14.

Kindrachuk, J., et al., "Ebola virus modulates transforming growth factor beta signaling and cellular markers of mesenchyme-like transition in hepatocytes." J Virol (2014); 88:9877-92.

Lofts, L.L., et al., "Genomic differences between guinea pig lethal and nonlethal Marburg virus variants." J Infect Dis (2007); 196(suppl 2):S305-12.

Marzi, A., et al., "Vesicular stomatitis virus-based Ebola vaccines with improved cross-protective efficacy." J Infect Dis (2011); 204(suppl 3):S1066-74.

Marzi, A., et al., "Ebola virus vaccines: an overview of current approaches." Expert Rev Vaccines (2014); 13:521-31.

McElroy, A.K., et al., "Biomarker correlates of survival in pediatric patients with Ebola virus disease." Emerg Infect Dis (2014); 20:1683-90.

McElroy, A.K., et al., "Von Willebrand Factor Is Elevated in Individuals Infected with Sudan Virus and Is Associated with Adverse Clinical Outcomes." Viral Immunol (2015); 28:71-3.

Munoz, J., "Comparison between Hartley and Strain 13 guinea pigs—antibody production and delayed hypersensitivity." J Immunol (1967); 99:31-9.

Okumura, A., et al., "Interaction be-tween Ebola virus glycoprotein and host toll-like receptor 4 leads to in-duction of proinflammatory cytokines and SOCS1." J Virol (2010); 84:27-33.

Qiu, X., et al., "Ebola GP-specific monoclonal antibodies protect mice and guinea pigs from lethal Ebola virus infection." PLoS Negl Trop Dis (2012); 6:e1575.

Qiu, X., et al., "Reversion of advanced Ebola virus disease in nonhuman primates with ZMapp." Nature (2014); 514:47-53.

Semeraro, N., et al., "Sepsis, thrombosis and organ dysfunction". Thromb Res (2012); 129:290-5.

Smith, D.H., et al., "Marburg-virus disease in Kenya." Lancet (1982); 1:816-20.

Steele, K.E., et al., Fibroblastic reticular cells and their role in viral hemorrhagic fevers. Expert Rev Anti Infect Ther (2009); 7:423-35.

Cross, et al., "Comparison of the Pathogenesis of the Angola and Ravn Strains of Marburg Virus in the Outbred Guinea Pig Model" Journal of Infectious Diseases, Jun. 19, 2015, 1-13.

Cross, et al., "Modeling the Disease Course of Zaire ebolavirus Infection in the Outbred Guinea Pig." Journal of Infectious Diseases, Jun. 2, 2015, pp. 1-11.

Mateo, et al., "VP24 Is a Molecular Determinant of Ebola Virus Virulence in Guinea Pigs." The Journal of Infectious Diseases, vol. 204, 2011, pp. 1-10.

Subbotina, et al., "Genetic Factors of Ebola Virus Virulence in Guinea Pigs." Virus Research, vol. 153, Oct. 2010, pp. 121-133.

Volchkov, et al., "Molecular Characterization of Guinea Pig-Adapted Variants of Ebola Virus." Virology, vol. 277, Issue 1, Nov. 10, 2000, pp. 147-155.

Wong, et al., "Development and Characterization of a Guinea Pig-Adapted Sudan Virus." Journal of Virology, vol. 90 No. 1, Jan. 2016, pp. 392-399.

Steinberg, B.E., et al., "Do viral infections mimic bacterial sepsis? The role of microvascular permeability: A review of mechanisms and methods." Antiviral Res (2012); 93:2-15.

Stroher, U., et al., "Infection and activation of monocytes by Marburg and Ebola viruses." J Virol (2001); 75:11025-33.

Stone, S.H., et al., "Differences in reactivity associated with sex or strain of inbred or random-bred guinea pigs in the massive hemorrhagic reaction and other manifestations of delayed hypersensitivity." Int Arch Allergy Immunol (1962); 20:193-202.

Sunden-Cullberg, J., et al., "Persistent elevation of high mobility group box-1 protein (HMGB1) in patients with severe sepsis and septic shock." Crit Care Med (2005); 33:564-73.

Swenson, D.L., et al., "Monovalent virus-like particle vaccine protects guinea pigs and nonhuman primates against infection with multiple Marburg viruses." Expert Rev Vaccines (2008); 7:417-29.

Thi, E.P., et al., Marburg virus infection in nonhuman primates: Therapeutic treatment by lipid-encapsulated siRNA. Sci Transl Med (2014); 6:250ra116.

Towner, J.S., et al., "Marburgvirus genomics and association with a large hemorrhagic fever outbreak in Angola." J Virol (2006); 80:6497-516.

Ursic-Bedoya, R., et al., "Protection Against Lethal Marburg Virus Infection Mediated by Lipid Encapsulated Small Interfering RNA." J Infect Dis (2014); 209:562-70.

Volchkova, V.A., et al., "Genomic RNA editing and its impact on Ebola virus adaptation during serial passages in cell culture and infection of guinea pigs." J Infect Dis (2011); 204(suppl 3):S941-6.

Wahl-Jensen, V., et al., "Role of Ebola virus secreted glycoproteins and virus-like particles in activation of human macro-phages." J Virol (2005); 79:2413-9.

Wahl-Jensen, V., et al., "Use of the Syrian hamster as a new model of ebola virus disease and other viral hemorrhagic fevers." Viruses (2012); 4:3754-84.

Warfield, K.L., et al., "Marburg virus-like particles protect guinea pigs from lethal Marburg virus infection." Vaccine (2004); 22:3495-502.

(56) References Cited

PUBLICATIONS

Warfield, K.L., et al., "Development and characterization of a mouse model for Marburg hemorrhagic fever." J Virol (2009); 83:6404-15.

* cited by examiner

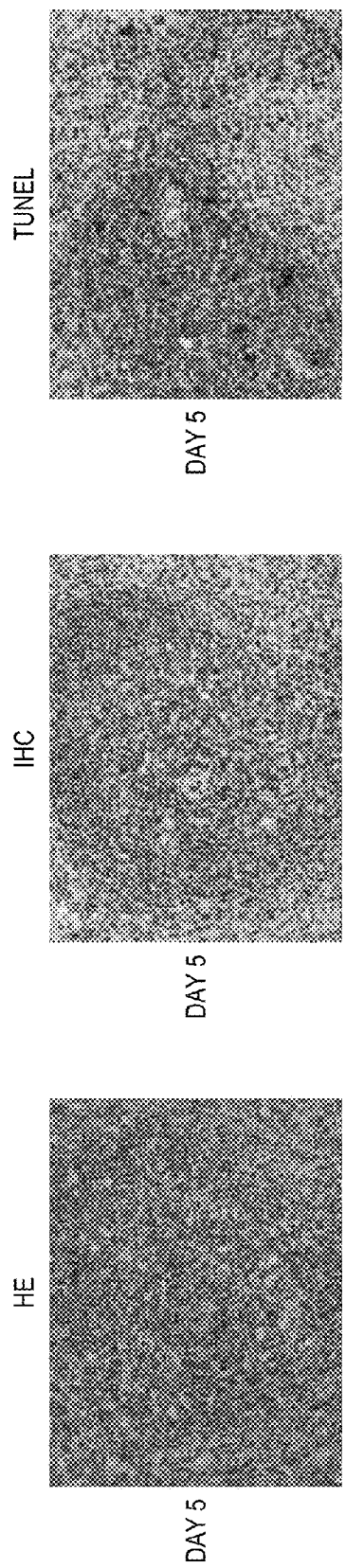
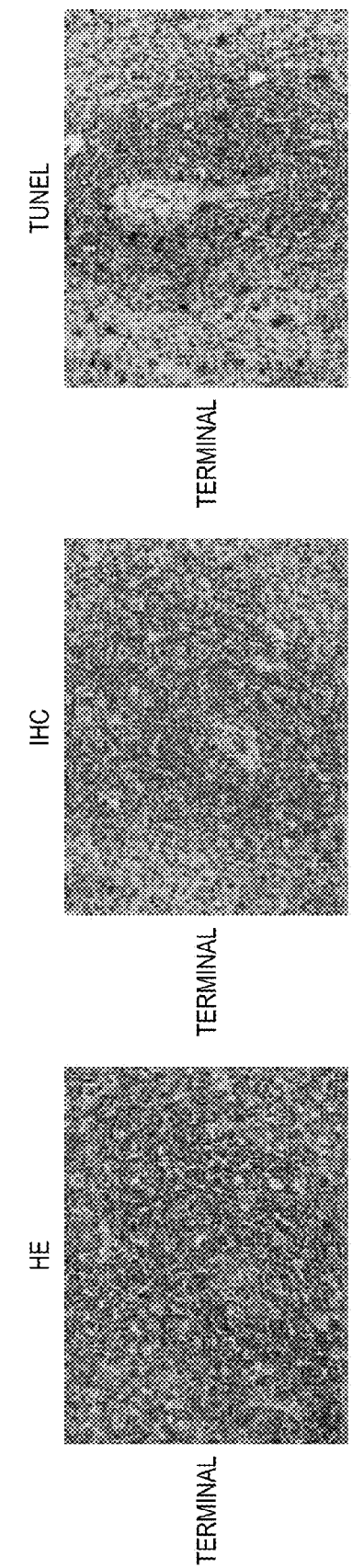
FIG. 3G  FIG. 3H  FIG. 3I
FIG. 3J  FIG. 3K  FIG. 3L

| | DAY 3 | DAY 4 | | DAY 5 | | DAY 6 | | DAY 7 | | DAY 8 | |
|---|---|---|---|---|---|---|---|---|---|---|---|
| | SD | MEAN | SD | MEAN | SD | MEAN | SD | MEAN | SD | MEAN | SD |
| | 14.9 | 51.9 | 11.5 | 46.7 | 8.0 | 51.4 | 6.2 | 63.7 | 4.5 | 59.5 | 8.1 |
| | 7.2 | 28.1 | 9.0 | 26.8 | 4.9 | 25.0 | 6.0 | 44.2 | 8.8 | 56.5 | 42.2 |
| | 5.3 | 22.8 | 8.4 | 25.4 | 12.1 | 23.6 | 4.8 | 23.3 | 5.6 | 37.3 | 12.2 |
| | 52.8 | 253.1 | 67.6 | 238.5 | 75.0 | 234.4 | 44.7 | 238.1 | 45.1 | 159.1 | 41.2 |
| | 12.7 | 89.0 | 17.5 | 79.5 | 2.0 | 86.7 | 10.5 | 77.2 | 22.4 | 73.1 | 9.7 |
| | 2.5 | 18.7 | 6.8 | 27.6 | 9.1 | 39.4 | 12.6 | 59.9 | 13.3 | 52.3 | 10.3 |
| | 239.1 | 241.5 | 328.2 | 1167.9 | 1313.9 | 0.0 | 0.0 | 137.3 | 274.6 | 0.0 | 0.0 |
| | 0.0 | 0.0 | 0.0 | 0.0 | 0.0 | 2.1 | 1.4 | 13.5 | 10.5 | 6.9 | 5.1 |
| | 83.0 | 45.4 | 63.3 | 0.0 | 0.0 | 0.0 | 0.0 | 22.0 | 25.4 | 36.4 | 37.8 |
| | 5.2 | 31.8 | 1.0 | 46.4 | 9.9 | 39.1 | 16.2 | 58.4 | 16.9 | 68.4 | 25.9 |
| | 60.3 | 60.4 | 29.7 | 195.1 | 59.4 | 112.8 | 107.9 | 162.9 | 103.5 | 145.7 | 77.8 |
| | 128.5 | 246.1 | 120.8 | 397.6 | 192.7 | 510.6 | 275.5 | 555.2 | 503.0 | 430.7 | 143.7 |
| | 100.7 | 208.4 | 76.1 | 242.5 | 153.6 | 49.9 | 30.1 | 477.3 | 435.9 | 377.3 | 141.0 |
| | 9.9 | 12.7 | 16.8 | 58.5 | 65.7 | 0.0 | 0.0 | 7.1 | 14.2 | 0.0 | 0.0 |
| | 83.0 | 522.0 | 162.0 | 692.0 | 297.0 | 741.0 | 113.0 | 1743.0 | 323.0 | 1014.0 | 154.0 |
| | 8.1 | 0.0 | 0.0 | 44.1 | 9.1 | 0.0 | 0.0 | 48.9 | 6.4 | 0.0 | 0.0 |
| | 28.7 | 16.1 | 24.5 | 19.1 | 24.9 | 40.5 | 28.0 | 81.6 | 34.9 | 89.6 | 47.6 |
| | 18.6 | 49.7 | 32.4 | 69.1 | 37.7 | 79.7 | 35.9 | 43.7 | 18.1 | 29.9 | 9.6 |

FIG. 4A-2

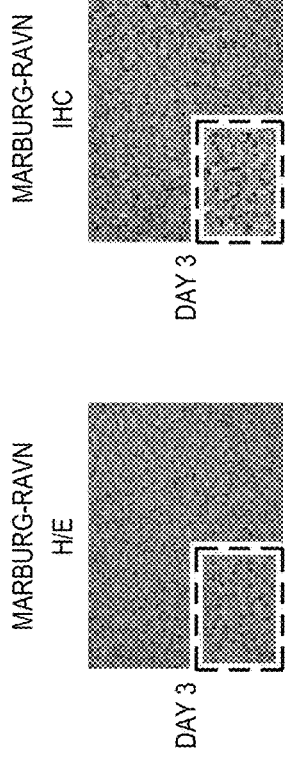
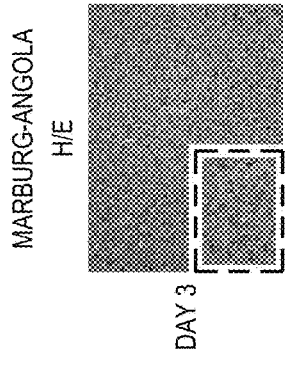
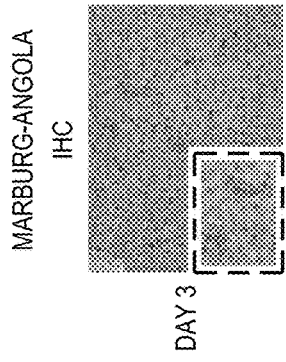
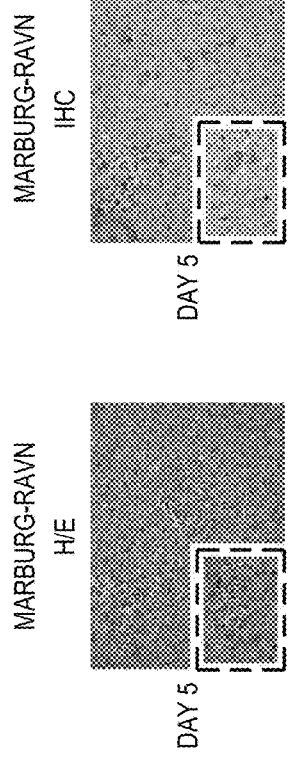
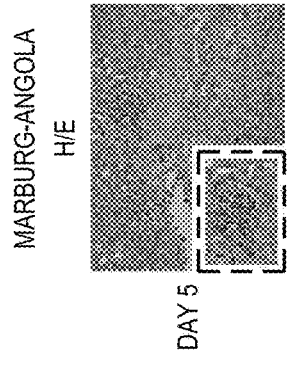
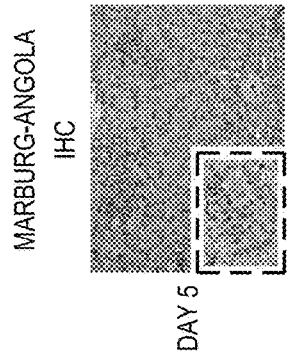
FIG. 6A  FIG. 6B  FIG. 6C  FIG. 6D
FIG. 6E  FIG. 6F  FIG. 6G  FIG. 6H

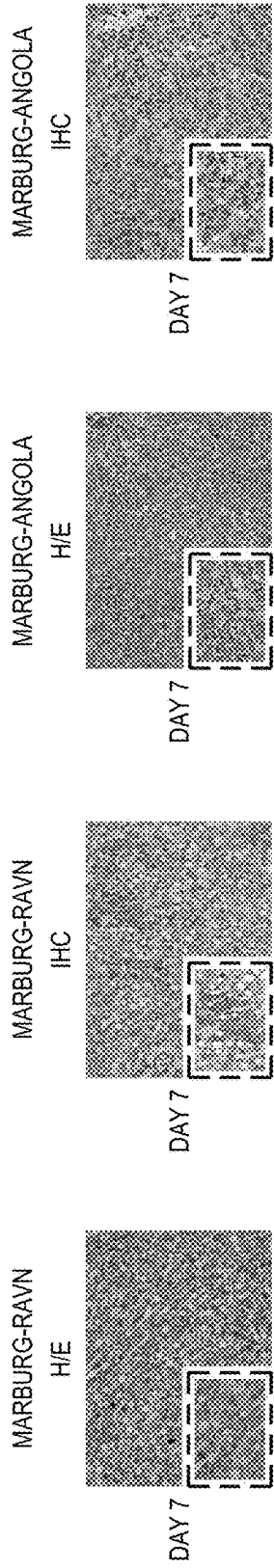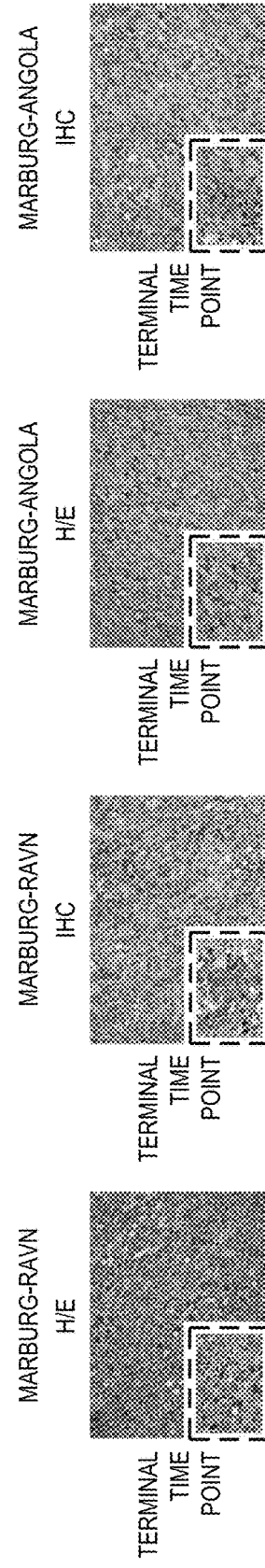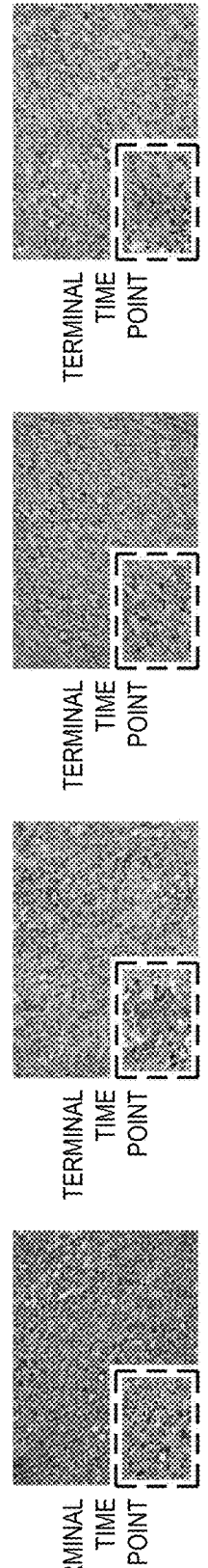
FIG. 6I  FIG. 6J  FIG. 6K  FIG. 6L
FIG. 6M  FIG. 6N  FIG. 6O  FIG. 6P

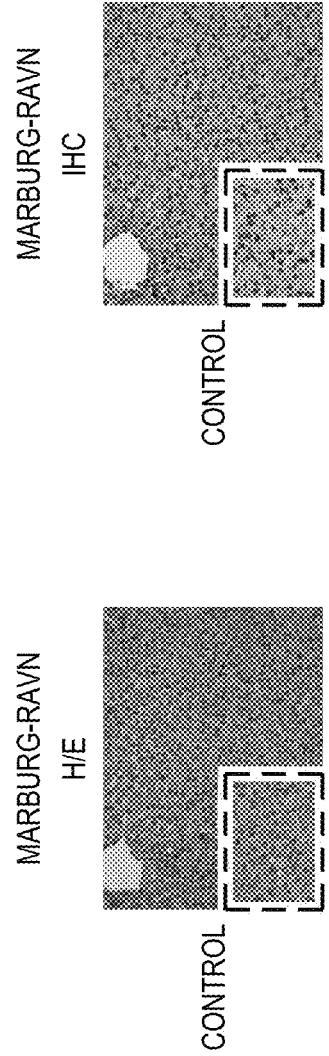

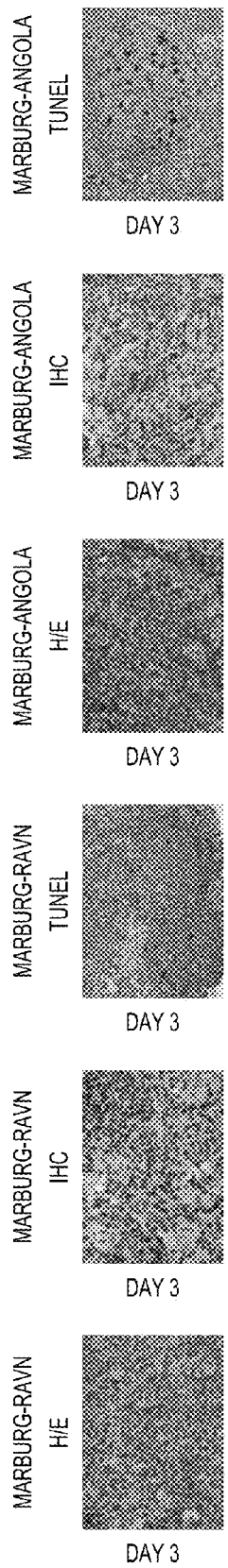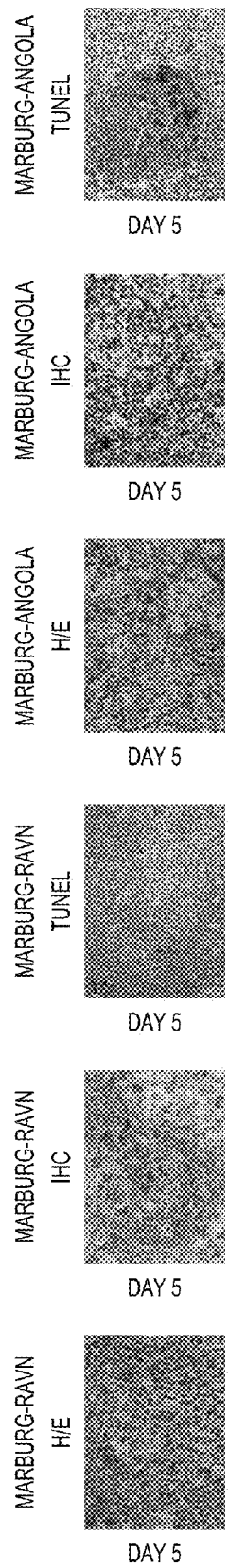

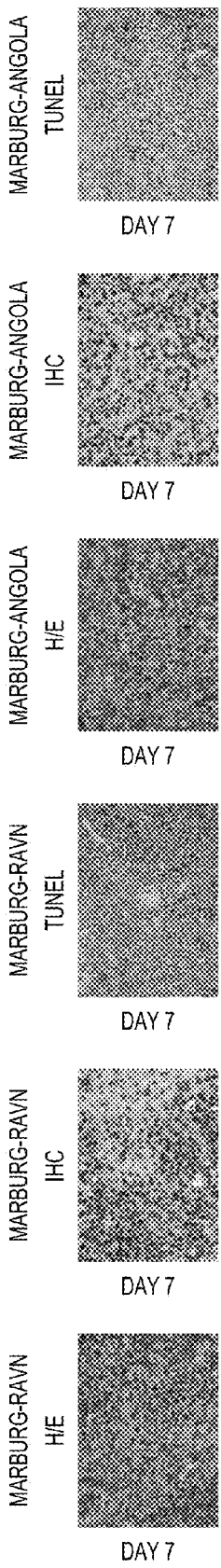
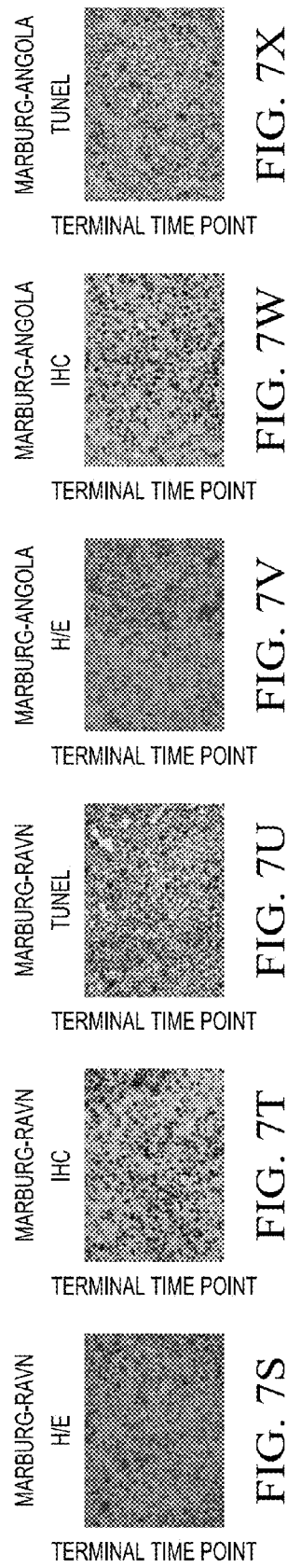

| COAGULATION PARAMETERS | PARAMETER | CONTROL | | DAY 1 | | DAY 3 | | DAY 5 | | DAY 7 | | TERMINAL TIME POINT | | VIRUS |
|---|---|---|---|---|---|---|---|---|---|---|---|---|---|---|
| | | MEAN | SD | MEAN | SD | MEAN | SD | MEAN | SD | MEAN | SD | MEAN | SD | |
| | PT, s | 3.8E+01 | 4.8E-01 | 3.0E-01 | 1.2E+00 | 4.3E+01 | 7.5E+00 | 6.3E+01 | 6.4E+00 | >70 | >70 | >70 | | RAVN |
| | | | | 3.7E-01 | 5.6E-01 | 4.2E+01 | 3.4E+00 | 5.5E+01 | 7.8E+00 | >70 | >70 | >70 | | ANGOLA |
| | APTT, s | 2.8E+01 | 4.

FIG. 8E-2

FROM FIG. 8E-1 / TO FIG. 8E-3

| Category | Analyte | | | | | | | | | | | | | | | Sample |
|---|---|---|---|---|---|---|---|---|---|---|---|---|---|---|---|---|
| COAGULATION PARAMETERS | PREKALIKREIN, pg/mL | 1.9E+01 | | 9.8E+00 | 1.1E+01 | 0.0E+00 | 0.0E+00 | 5.0E+00 | 6.4E+00 | 1.3E+01 | 1.5E+01 | 2.0E-01 | 1.7E+01 | RAVN |
| | | | 1.4E+01 | 0.0E+00 | 0.0E+00 | 5.6E+00 | 1.1E+01 | 1.0E+01 | 1.2E+01 | 3.8E+01 | 4.6E+00 | 2.6E-01 | 9.3E+00 | ANGOLA |
| | PAI-1, ng/mL | 2.2E+01 | | 1.7E+01 | 2.0E+01 | 1.5E+01 | 2.9E+01 | 6.3E+01 | 2.1E+01 | 1.2E+02 | 2.6E+01 | 1.3E+02 | 2.0E+01 | RAVN |
| | | | 1.5E+01 | 2.0E+01 | 1.5E+01 | 2.9E+01 | 2.6E+01 | 3.2E+01 | 1.4E+01 | 3.8E+01 | 2.9E+01 | 9.9E+01 | 2.7E+01 | ANGOLA |
| | TAFI, ng/mL | 0.0E+00 | | 2.0E+01 | 0.0E+00 | 2.5E+01 | 2.9E+00 | 5.0E+01 | 3.4E+01 | 2.3E+01 | 1.3E+01 | 6.2E+01 | 4.3E+01 | RAVN |
| | | | 0.0E+00 | 0.0E+00 | 0.0E+00 | 2.9E+00 | 5.7E+00 | 3.5E+00 | 7.1E+00 | 5.9E+01 | 4.4E+01 | 5.8E+01 | 3.0E+01 | ANGOLA |
| | TISSUE FACTOR, pg/mL | 5.9E+01 | | 4.9E+01 | 2.9E+00 | 5.4E+01 | 1.7E+00 | 4.9E+01 | 6.7E+00 | 3.9E+01 | 4.3E+00 | 2.5E-01 | 2.0E+01 | RAVN |
| | | | 2.9E+00 | 5.3E+01 | 2.2E+00 | 5.2E+01 | 4.5E+00 | 4.7E+02 | 1.1E+01 | 3.9E+01 | 1.7E+01 | 2.0E-01 | 3.8E+00 | ANGOLA |
| | VWF, ng/mL | 1.5E+02 | | 1.3E+02 | 3.9E+01 | 1.2E+02 | 3.0E+01 | 1.4E+02 | 6.2E+01 | 1.8E+02 | 8.7E+01 | 2.6E+02 | 5.4E+01 | RAVN |
| | | | 2.3E+01 | 1.4E+02 | 3.4E+01 | 1.4E+02 | 1.0E+01 | 7.3E+01 | 1.8E+01 | 2.9E+02 | 5.8E+01 | 2.3E+02 | 5.6E+01 | ANGOLA |
| INFLAMMATORY MARKERS | PROSTAGLANDIN E2, pg/mL | 2.1E+01 | | 1.8E+01 | 1.4E+01 | 1.5E+01 | 7.6E+00 | 4.7E+01 | 1.1E+01 | 8.8E+01 | 2.0E+01 | 6.4E+01 | 5.0E+00 | RAVN |
| | | | 1.3E+01 | 1.3E+01 | 8.7E+00 | 6.8E+00 | 3.3E+00 | 2.1E+01 | 1.2E+01 | 6.5E+01 | 6.4E+00 | 6.7E+01 | 4.8E+00 | ANGOLA |
| | LEUKOTRIENE B4, pg/mL | 1.8E+02 | | 1.9E+02 | 2.0E+01 | 3.9E+02 | 9.9E+01 | 1.4E+02 | 41.40 | 3.3E+02 | 1.0E+02 | 5.2E+02 | 1.9E+02 | RAVN |
| | | | 9.0E+01 | 3.7E+02 | 1.2E+02 | 2.6E+02 | 4.8E+01 | 4.7E+02 | 2.4E+02 | 5.1E+02 | 2.9E+02 | 8.7E+02 | 3.3E+02 | ANGOLA |
| | CYSTEINAL LEUKOTRIENES, pg/mL | 3.8E+01 | | 5.1E+01 | 1.1E+00 | 8.2E+01 | 2.2E+01 | 4.9E+01 | 2.8E+01 | 2.1E+02 | 5.2E+01 | 3.6E+02 | 4.2E+01 | RAVN |
| | | | 1.8E+01 | 6.3E+01 | 1.5E+01 | 4.2E+01 | 1.0E+02 | 7.2E+01 | 1.7E+02 | 5.4E+01 | 3.4E+02 | 7.2E+01 | | ANGOLA |

FROM FIG. 8E-2

| INFLAMMATORY MARKERS | | | | | | | | | | | | | |
|---|---|---|---|---|---|---|---|---|---|---|---|---|---|
| THROMBOXANE B2, pg/mL | 3.4E+02 | 1.1E+02 | 3.5E+02 | 1.1E+02 | 7.4E+02 | 1.2E+02 | 7.8E+02 | 1.5E+02 | 6.7E+02 | 1.4E+02 | 1.2E+03 | 1.8E+02 | RAVN |
| | | | 4.0E+02 | 7.1E+01 | 4.9E+02 | 1.1E+02 | 5.4E+02 | 8.8E+01 | 4.6E+02 | 5.9E+01 | 4.5E+02 | 7.1E+01 | ANGOLA |
| 6-KETO PROSTAGLANDIN F1α, pg/mL | 9.3E+00 | 3.3E+00 | 9.1E+00 | 1.4E+00 | 3.7E+01 | 1.4E+01 | 4.1E+01 | 1.5E+01 | 9.9E+01 | 4.0E+01 | 3.0E+02 | 1.9E+02 | RAVN |
| | | | 1.3E+01 | 3.5E+00 | 1.4E+01 | 3.3E+00 | 9.2E+01 | 8.3E+01 | 9.4E+01 | 6.5E+01 | 2.9E+02 | 2.9E+02 | ANGOLA |
| TGF-ß, pg/mL | 2.1E+00 | 4.2E+00 | 2.0E+00 | 4.0E+00 | 1.2E+00 | 1.3E+00 | 6.8E+00 | 7.4E+00 | 1.3E+01 | 8.0E+00 | 1.8E+01 | 5.2E+00 | RAVN |
| | | | 0.0E+00 | 0.0E+00 | 0.0E+00 | 0.0E+00 | 1.2E+00 | 1.8E+00 | 1.7E+01 | 5.1E+00 | 1.9E+01 | 6.6E+00 | ANGOLA |
| HMGB-1, pg/mL | 2.0E+02 | 1.4E+02 | 2.3E+03 | 1.6E+03 | 3.0E+03 | 6.2E+02 | 2.5E+03 | 7.1E+02 | 1.5E+03 | 4.5E+02 | 1.1E+03 | 1.4E+03 | RAVN |
| | | | 1.1E+03 | 4.5E+02 | 4.7E+02 | 3.1E+02 | 1.9E+03 | 5.6E+02 | 3.3E+02 | 6.5E+02 | 4.2E+02 | 4.3E+02 | ANGOLA |
| TNF-α, pg/mL | 1.1E+02 | 4.6E+01 | 2.1E+01 | 2.8E+01 | 0.0E+00 | 0.0E+00 | 2.2E+02 | 2.6E+02 | 1.7E+02 | 4.2E+01 | 4.1E+02 | 1.0E+02 | RAVN |
| | | | 3.8E+01 | 3.8E+01 | 5.6E+01 | 6.6E+01 | 1.0E+02 | 9.2E+01 | 3.8E+02 | 8.3E+01 | 4.7E+02 | 9.5E+01 | ANGOLA |
| IL-6, pg/mL | 1.4E+01 | 2.8E+01 | 6.3E+01 | 9.1E+01 | 2.7E+01 | 5.3E+01 | 1.4E+02 | 9.7E+01 | 4.1E+02 | 1.1E+02 | 3.2E+02 | 1.7E+02 | RAVN |
| | | | 0.0E+00 | 0.0E+00 | 5.9E+00 | 1.2E+01 | 2.1E+01 | 5.2E+01 | 3.7E+02 | 2.4E+02 | 5.8E+02 | 1.8E+02 | ANGOLA |
| NO, μM NITRITE | 2.1E-01 | 4.3E-01 | 0.0E+00 | 0.0E+00 | 0.0E+00 | 0.0E+00 | 1.5E+01 | 1.2E+01 | 3.0E+01 | 1.8E+01 | 6.9E+01 | 6.9E+01 | RAVN |
| | | | 0.0E+00 | 0.0E+00 | 0.0E+00 | 0.0E+00 | 8.1E+00 | 1.4E+01 | 9.4E+01 | 4.5E+01 | 1.3E+02 | 8.6E+01 | ANGOLA |

FIG. 8E-3

VARIANT ANGOLA MARBURG VIRUS

CROSS-REFERENCE TO RELATED APPLICATIONS

None.

TECHNICAL FIELD OF THE INVENTION

The present invention relates in general to the field of model systems for studying highly virulent viruses, and more particularly, to mammalian model systems for the systematic evaluation of filoviruses.

STATEMENT OF FEDERALLY FUNDED RESEARCH

None.

BACKGROUND OF THE INVENTION

Without limiting the scope of the invention, its background is described in connection with Filovirus infection of small mammals.

Volchkov, et al., in an article entitled "Molecular Characterization of Guinea Pig-Adapted Variants of Ebola Virus," Virology 277, 147±155 (2000), 147-155, teach that serial passage of initially nonlethal Ebola virus (EBOV) in outbred guinea pigs resulted in the selection of variants with high pathogenicity. It was further found by nucleotide sequence analysis of the complete genome of the guinea pig-adapted variant 8mc, that the guinea pig-adapted variant differed from wild-type virus by eight mutations, however, no mutations were identified in nontranscribed regions, including leader, trailer, and intragenic sequences.

Mateo, et al., in an article entitled "VP24 Is a Molecular Determinant of Ebola Virus Virulence in Guinea Pigs," J. Inf. Dis. 2011:204 (Suppl. 3), S1011-S1020, show that serial passaging of EBOV in guinea pigs results in a selection of variants with high pathogenicity. They teach, using a reverse genetics approach, that the increase in EBOV pathogenicity is associated with amino acid substitutions in the structural protein VP24, however, replication of recombinant EBOV carrying wild-type VP24 was impaired in primary peritoneal guinea pig macrophages and in the liver of infected animals. The substitutions in VP24 allowed EBOV to replicate in guinea pig macrophages and spread in the liver of infected animals.

Subbotina, et al., in an article entitled "Genetic factors of Ebola virus virulence in guinea pigs," Virus Research 153 (2010) 121-133, teach that selective passages of Ebola virus in guinea pigs resulted in a guinea pig-adapted strain (GPA-P7) strain. By the 7th passage, the infection with the adapted EBOV induced a lethal disease in animals accompanied by the characteristic hematological changes, viz., leukocytosis (primarily due to neutrophilia), a pronounced deficiencies in platelets, lymphocytes, monocytes and a significant decrease of blood neutrophil's phagocytic capacity. The increased virulence is said to correlate with appearance of several nucleotide substitutions: in the genes NP, A2166G (N566S), VP24, U10784C (L147P), G10557A (M711), G10805U (R154L), and L, G12286A (V2361). It was theoretically calculated that the mutations associated with an increase in EBOV virulence alter the secondary structure of the proteins NP (C-terminal region) and full-sized VP24.

SUMMARY OF THE INVENTION

In one embodiment, the present invention includes a uniformly lethal ZEBOV-Mayinga filovirus strain adapted for virulence in a small mammal, wherein the strain comprises one or more of the following mutations when compared to Accession No. AF086833.2:

| Nucleotide | Base Change | Result | Gene |
|---|---|---|---|
| 652 | A > G | Silent | NP |
| 2192 | G > A | A575T | NP |
| 2409 | C > A | S647Y | NP |
| 5219 | U > C | Silent | VP40 |
| 7668 | U > C | I544T | GP |
| 10258 | G > A | | Non-coding |
| 10768 | A > G | K142E | VP24. |

Another embodiment of the present invention includes uniformly lethal SEBOV-Boniface filovirus strain adapted for virulence in a small mammal, wherein the strain comprises one or more of the following mutations when compared to Accession No. FJ968794.1:

| Nucleotide | Base Change | Result | Gene |
|---|---|---|---|
| 2640 | A > G | Q728R | NP |
| 6286 | U > G | F97V | GP |
| 8150 | C > A | | Non-coding |
| 10363 | U > C | V22A | VP24 |
| 12751 | C > U | S406F | L |
| 15364 | A > G | H1277R | L |
| 18303 | A > G | | Non-coding. |

Another embodiment of the present invention includes uniformly lethal MARV-Angola filovirus strain adapted for virulence in a small mammal, wherein the strain comprises one or more of the following mutations when compared to Accession No. DQ447653:

| Nucleotide | Base Change | Result | Gene |
|---|---|---|---|
| 2931 | U > A | | Non-coding |
| 4735 | U > A | N56K | VP40 |
| 10402 | G > A | V66I | YP24 |
| 10853 | U > C | L216S | VP24 |
| 13115 | U > C | Silent | L |
| 17249 | U > A | Silent | L |
| 18713 | C > A | | Non-coding |
| 19105 | A > U | | Non-coding. |

Another embodiment of the present invention includes a uniformly lethal MARV-Ci67 filovirus strain adapted for virulence in a small mammal, wherein the strain comprises one or more of the following mutations when compared to Accession No. EF446132.1:

| Nucleotide | Base Change | Result | Gene |
|---|---|---|---|
| 8811 | ->U | | Non-coding |
| 10629 | G > A | G141E | VP24 |
| 10631 | A > U | I142S | VP24 |
| 10632 | U > C | I142S | VP24 |
| 10633 | C > U | I142S | VP24 |
| 10634 | U > A | Y143I | VP24 |
| 10635 | A > U | Y143I | VP24. |

Yet another embodiment of the present invention includes a uniformly lethal MARV-Ravn filovirus strain adapted for virulence in a small mammal, wherein the strain comprises one or more of the following mutations when compared to Accession No. DQ447649.1:

| Nucleotide | Base Change | Result | Gene |
|---|---|---|---|
| 143 | A > U | T14S | NP |
| 4647 | U > C | L27S | VP40 |
| 4665 | U > C | L33P | VP40 |
| 4725 | U > C | F53S | VP40 |
| 4726 | U > C | F53S | VP40 |
| 7118 | G > C | G435A | GP |
| 13787 | U > C | Silent | L. |

Another embodiment of the present invention includes a method of determining the effectiveness of a candidate drug that impacts a filovirus infection or virulence, the method comprising: (a) injecting a mutated filovirus adapted to lethally infect an outbred small mammal; (b) administering the candidate drug to a first subset of the outbred small mammal, and a placebo to a second subset of the outbred small mammal; (c) determining the effect of the candidate drug on the first and second subset of outbred small mammals infected with the mutated filovirus; (d) determining if the candidate drug modifies one or more symptoms selected from at least one of the infectious dose, a lethal dose, fever, weight loss, and infection of mononuclear/dendritiform cells, splenic and hepatic pathology, lymphocyte apoptosis, neutrophilia, thrombocytopenia, marked granulocytosis, coagulopathies, vascular leakage, or macular rashes, of the mutated filovirus in the first versus the second subset of outbred small mammals, wherein a decrease in one or more of the symptoms over the course of the treatment with the candidate drug is indicative of effectiveness against the filovirus virus.

Yet another embodiment of the present invention includes a method of making a uniformly lethal mutated filovirus for outbred small mammals by mutation of the viral genome through serial passages in a small mammal, the method comprising the steps of: obtaining a filovirus strain from a human subject; passing the filovirus strain one or more times by intramuscular injection of an inbred small mammal until uniform lethality is obtained; passing the filovirus strain in one or more human cell lines; passing the filovirus strain one or more times by intraperitoneal injection of an outbred small mammal until uniform lethality is obtained; and isolating the uniformly lethal mutated filovirus obtained thereby. In one aspect, the filovirus is selected from at least one of an Ebola virus or a Marburg virus. In another aspect, the human cells are Vero E6 cells (ATCC1587), or Vero 76 cells (ATCC1586). In another aspect, the uniformly lethal mutated filovirus comprises mutations in at least one of the non-coding regions, nucleoprotein (NP), viral protein 40 (VP40), glycoprotein, viral protein 24 (VP24), or RNA-directed RNA polymerase (L protein). In another aspect, the small mammal is selected from at least one of a guinea pig, Hartley guinea pig, mouse, rat, hamster, or Syrian golden hamster. In another aspect, the filovirus is a Marburg virus selected from at least one of Angola, Ci67, Musoke, Ozolin, or Ravn strain. In another aspect, the inbred small mammal is a Strain 13 guinea pig. In another aspect, the mutated virus is passed at least three times through an infection cycle in the inbred small mammal. In another aspect, the mutated virus is passed at least three times through an infection cycle in the outbred small mammal. In another aspect, the method further comprises the step of sequencing at least part of the genome of the mutated filovirus strain after adaptation into the outbred small mammal. In another aspect, the mutated filovirus is passed through a human cell line between each passage of the inbred, the outbred animal, or both the inbred and outbred animal. In another aspect, the filovirus is an ebola virus selected from at least one of Zaire ebolavirus (ZEBOV), Sudan ebolavirus (SEBOV), Bundibugyo ebolavirus (BEBOV), Ivory Coast ebolavirus (also known as Tai Forest ebolavirus), and Reston ebolavirus. In another aspect, the mutated filovirus obtained by the method is a ZEBOV-Mayinga Guinea Pig Adapted Strain comprises one or more of the following mutations when compared to Accession No. AF086833.2:

| Nucleotide | Base Change | Result | Gene |
|---|---|---|---|
| 652 | A > G | Silent | NP |
| 2192 | G > A | A575T | NP |
| 2409 | C > A | S647Y | NP |
| 5219 | U > C | Silent | VP40 |
| 7668 | U > C | I544T | GP |
| 10258 | G > A |  | Non-coding |
| 10768 | A > G | K142E | VP24. |

In another aspect, the mutated filovirus obtained by the method is a SEBOV-Boniface Guinea Pig Adapted Strain comprises one or more of the following mutations when compared to Accession No. FJ968794.1:

| Nucleotide | Base Change | Result | Gene |
|---|---|---|---|
| 2640 | A > G | Q728R | NP |
| 6286 | U > G | F97V | GP |
| 8150 | C > A |  | Non-coding |
| 10363 | U > C | V22A | VP24 |
| 12751 | C > U | S406F | L |
| 15364 | A > G | H1277R | L |
| 18303 | A > G |  | Non-coding. |

In another aspect, the mutated filovirus obtained by the method is a MARV-Angola Guinea Pig Adapted Strain comprises one or more of the following mutations when compared to Accession No. DQ447653:

| Nucleotide | Base Change | Result | Gene |
|---|---|---|---|
| 2931 | U > A |  | Non-coding |
| 4735 | U > A | N56K | VP40 |
| 10402 | G > A | V66I | VP24 |
| 10853 | U > C | L216S | VP24 |
| 13115 | U > C | Silent | L |
| 17249 | U > A | Silent | L |
| 18713 | C > A |  | Non-coding |
| 19105 | A > U |  | Non-coding. |

In another aspect, the wherein the mutated filovirus obtained by the method is a MARV-Ci67 Guinea Pig Adapted Strain comprises one or more of the following mutations when compared to Accession No. EF446132.1:

| Nucleotide | Base Change | Result | Gene |
|---|---|---|---|
| 8811 | ->U |  | Non-coding |
| 10629 | G > A | G141E | VP24 |
| 10631 | A > U | I142S | VP24 |
| 10632 | U > C | I142S | VP24 |
| 10633 | C > U | I142S | VP24 |
| 10634 | U > A | Y143I | VP24 |
| 10635 | A > U | Y143I | VP24. |

In another aspect, the mutated filovirus obtained by the method MARV-Ravn Guinea Pig Adapted Strain comprises one or more of the following mutations when compared to Accession No. DQ447649.1:

| Nucleotide | Base Change | Result | Gene |
|---|---|---|---|
| 143 | A > U | T14S | NP |
| 4647 | U > C | L27S | VP40 |
| 4665 | U > C | L33P | VP40 |
| 4725 | U > C | F53S | VP40 |
| 4726 | U > C | F53S | VP40 |
| 7118 | G > C | G435A | GP |
| 13787 | U > C | Silent | L |

In another aspect, the guinea pig adapted Angola strain of Marburg triggers is capable of triggering macular rashes in the outbred small mammal. In another aspect, the small mammal is not a primate.

Yet another embodiment of the present invention includes a method of making a uniformly lethal mutant filovirus for outbred small mammals comprising: adapting a mutant filovirus by mutation of the viral genome through serial passages in a small mammal the method comprising the steps of: isolating a filovirus strain from a human subject and injecting an outbred small mammal; passing the filovirus strain one or more times by infection with a liver and spleen homogenate obtained from lethally infected outbred guinea pigs until uniform lethality is obtained; passing the filovirus strain in one or more human cell lines and infecting the outbred small mammal; passing the filovirus strain one or more times by infection of the filovirus into the outbred small mammal until uniform lethality is obtained; and isolating the uniformly lethal mutated filovirus obtained thereby, wherein the uniformly lethal mutant filovirus is capable of uniformly infecting outbred small mammals.

BRIEF DESCRIPTION OF THE DRAWINGS

For a more complete understanding of the features and advantages of the present invention, reference is now made to the detailed description of the invention along with the accompanying FIG.s and in which:

FIG. 1B, Gross lesions were noted in the following organs of ZEBOV-infected guinea pigs: liver (asterisk), diffuse pallor (hepatocellular degeneration/necrosis); lung (white arrow), petechiae, rib impressions, and failure to collapse (interstitial pneumonia); intestines (white arrow), flaccid with liquid contents; and colon and uterus (white arrow), multifocal serosal congestion. FIG. 1C, Gross lesions were noted in the stomach of ZEBOV-infected guinea pigs: serosal hemorrhage (white arrow) and mucosal ulceration (inset). FIG. 1D, Gross lesions were noted in and near the distal limb of ZEBOV-infected guinea pigs, as follows: subcutaneous tissues of the distal limb, locally extensive hemorrhage (#); and inguinal lymph node, hemorrhage (white arrow). FIG. 1E, Weight loss and temperature over the course of the study in ZEBOV-infected guinea pigs (solid red line and dotted red line, respectively) and control guinea pigs (solid black line and dotted black line, respectively).

FIG. 2A-FIG. 2E) and corresponding anti-Ebola virus immunohistochemical staining (FIG. 2F-FIG. 2J) of Zaire Ebola virus (ZEBOV)-infected guinea pig liver, by day after infection, and control guinea pig liver. All images are 20 times the original magnification, with inserts showing 60 times the original magnification. Infected liver, day 2: no significant lesions (NSLs; FIG. 2A) and diffuse cytoplasmic immunolabeling of rare Kupffer cells (FIG. 2F). Infected liver, day 3: multifocal hepatocellular degeneration/necrosis and sinusoidal leukocytosis (FIG. 2B) and diffuse cytoplasmic immunolabeling of Kupffer cells, associated inflammatory nodules, and small clusters of hepatocytes (FIG. 2G). Infected liver, day 5: multifocal hepatocellular degeneration/ necrosis, sinusoidal leukocytosis, councilman body, and eosinophilic cytoplasmic inclusion bodies (FIG. 2C) and diffuse cytoplasmic immunolabeling of Kupffer cells and small clusters of hepatocytes (H). Infected liver, terminal time point: hepatocellular vacuolation, degeneration/necrosis, sinusoidal leukocytosis, and eosinophilic cytoplasmic inclusion bodies (FIG. 2D) diffuse cytoplasmic immunolabeling of Kupffer cells and medium clusters of hepatocytes (FIG. 2I). Control liver: NSL (FIG. 2E) and no significant immunolabeling (FIG. 2J).

FIG. 3A), diffuse cytoplasmic immunolabeling of rare mononuclear cells in the red pulp (FIG. 3B), and minimal immunolabeling within the white pulp (FIG. 3C). Infected spleen, day 3: NSL (FIG. 3D), diffuse cytoplasmic immunolabeling of small clusters of mononuclear cells in the red and white pulp (FIG. 3E), and moderate immunolabeling within the white pulp (FIG. 3C). Infected spleen, day 5: lymphoid depletion with tingible body macrophages within the white pulp (FIG. 3G), diffuse cytoplasmic immunolabeling of mononuclear cells in the red and white pulp (FIG. 3H), and marked immunolabeling within the white pulp (FIG. 3I). Infected spleen, terminal time point: lymphoid depletion with tingible body macrophages within the white pulp (FIG. 3J), diffuse cytoplasmic immunolabeling of mononuclear cells in the red and white pulp (FIG. 3K), and marked immunolabeling within the white pulp (FIG. 3L). Control guinea pig spleen: NSL (FIG. 3M), no significant immunolabeling (FIG. 3N), and minimal immunolabeling within the white pulp (FIG. 3O).

FIGS. 4A-1, 4A-2 to 4C show: FIGS. 4A-1, 4A-2 are a heat map of coagulation parameters and proinflammatory markers. FIG. 4C shows anti-fibrin immunohistochemical staining of Ebolavirus-infected guinea pig spleen on day 8 after infection (original magnification ×20). Immunolabeling was scattered throughout the red pulp and clustered within the marginal zone of the germinal centers. Abbreviations: APTT, activated partial prothrombin time; HMGB-1, high mobility group box-1; IL-6, interleukin 6; PAI-1, plasminogen activator inhibitor-1; PT, prothrombin time; SD, standard deviation; TAFI, thrombin activatable fibrinolysis inhibitor; TGF-β, transforming growth factor β; TNF-α, tumor necrosis factor α; TT, thrombin time; VWF, Von Willebrand factor.

FIG. 5A, Survival curve of guinea pigs (GPs) infected with Marburg virus Ravn (MARV-Rav; blue line) and MARV-Angola (MARV-Ang; red line). FIG. 5B, Percentage weight loss and temperature during the study. MARV-Rav-infected GPs are represented by blue solid lines (weight) and dotted lines (temperature), Marv-Ang-infected GPs are represented by red solid lines (weight) and dotted lines (temperature), and control GPs are represented by black solid lines (weight) and dotted lines (temperature) lines. FIG. 5C-FIG. 5F, Comparison of the gross pathology of mock-infected control GPs (FIG. 5C), MARV-Rav-infected GPs (FIG. 5E), and MARV-Ang-infected GPs (FIG. 5D and FIG. 5F) at terminal time points. Gross lesions were noted in the MARV-Rav GPs (FIG. 5E) and MARV-Ang GPs (FIG. 5D and FIG. 5F), liver (black asterisk) moderate multifocal to diffuse pallor (hepatocellular degeneration/necrosis) (FIG. 5E), severe multifocal to diffuse pallor (hepatocellular degeneration/necrosis) (FIG. 5F insets), gastric congestion (black arrow), gastric ulceration (FIG. 5D inset), prominent lymphoid tissues (white arrowhead) (FIG. 5F), flaccid/fluid filled intestines (#) (FIG. 5D, FIG. 5F and FIG. 5E).

FIGS. 6A to 6R show the histopathology of liver: Panels include Hemotoxylin & Eosin (H&E) MARV-Rav (FIG. 6A, FIG. 6E, FIG. 6I, and FIG. 6M) with corresponding anti-Marburg immunohistochemistry (IHC) (FIG. 6B, FIG. 6F, FIG. 6J, and FIG. 6N), H&E MARV Ang (FIG. 6C, FIG. 6G, FIG. 6K, and FIG. 6O) with corresponding anti-Marburg IHC (FIG. 6D, FIG. 6H, FIG. 6L, and FIG. 6P), and H&E control (FIG. 6Q) which has no significant lesions (NSL), nor any significant immunolabeling in corresponding anti-Marburg IHC (FIG. 6R). All images are 20× with 60× inserts. MARV-Rav-infected GP liver at day 3 (FIG. 6A) had NSL detected but had diffuse cytoplasmic immunolabeling of kupffer cells present (FIG. 6B). H&E of MARV-Rav-infected GP liver on day 5 (FIG. 6E) presented evidence of multifocal hepatocellular degeneration/necrosis and sinusoidal leukocytosis with diffuse cytoplasmic immunolabeling of Kupffer cells and small clusters of hepatocytes (FIG. 6F). Day 7 MARV-Rav-infected GP demonstrated progressive multifocal hepatocellular vacuolar degeneration/necrosis and sinusoidal leukocytosis on H&E (FIG. 6I), which was accompanied by diffuse cytoplasmic immunolabeling of Kupffer cells and clusters of hepatocytes (FIG. 6J). Terminal MARV-Rav-infected GP had advanced multifocal hepatocellular vacuolar degeneration/necrosis and sinusoidal leukocytosis (FIG. 6M) accompanied by diffuse cytoplasmic immunolabeling of Kupffer cells and sheets of hepatocytes (FIG. 6N). Day 3 MARV-Ang-infected GP had NSL on H&E (FIG. 6C) yet diffuse cytoplasmic immunolabeling of Kupffer cells and small clusters of hepatocytes was present (FIG. 6D). Day 5 MARV-Ang-infected GP had multifocal hepatocellular degeneration/necrosis and sinusoidal leukocytosis on H&E (FIG. 6G), which was associated with diffuse cytoplasmic immunolabeling of Kupffer cells and clusters of hepatocytes (FIG. 6H). Day 7 MARV-Ang-infected GP had marked multifocal hepatocellular vacuolar degeneration/necrosis and sinusoidal leukocytosis on H&E (FIG. 6K) with diffuse cytoplasmic immunolabeling of Kupffer cells and clusters of hepatocytes (FIG. 6L). Terminal MARV-Ang-infected GP had severe, multifocal hepatocellular vacuolar degeneration/necrosis and sinusoidal leukocytosis on H&E (FIG. 6O) associated with diffuse cytoplasmic immunolabeling of Kupffer cells and sheets of hepatocytes (FIG. 6P). Abbreviations: GP, guinea pig; MARV, Marburg virus.

FIGS. 8A to 8E-1 to 8E-3 show fibrin specific immunohistochemistry of GP spleens: Control GP had no significant immunolabeling (FIG. 8A). Day 7 MARV-Rav-infected GP had minimal anti-fibrin immunolabeling scattered throughout the red pulp and clustered in the white pulp (FIG. 8B). Day 7 MARV-Ang-infected GP with anti-fibrin immunolabeling scattered throughout the red pulp and clustered in the white pulp (FIG. 8C). Inset depicts representative immunolabeling of fibrin strands and aggregates surrounding red and white blood cells within the vessel, along the endothelium, and clusters that disperse into the adjacent red and white pulp (FIG. 8D). All 20× with 60× insert in (FIG. 8D). Heat map and expression levels of coagulation factors and inflammatory molecules detected through the course of infection (FIGS. 8E-1 to 8E-3). Abbreviations: APTT, activated partial thromboplastin times; GP, guinea pig; HMGB-1, high-mobility group B1; IL-6, interleukin 6; MARV, Marburg virus; NO, nitric oxide; PAI-1, plasminogen activator inhibitor 1; PT, partial thrombin; SD, standard deviation; TAFI, thrombin-activated fibrinolysis inhibitor; TGF, transforming growth factor; TNF, tumor necrosis factor; TT, thrombin time; VWF, Von Willebrand factor.

DETAILED DESCRIPTION OF THE INVENTION

Figure 1A:
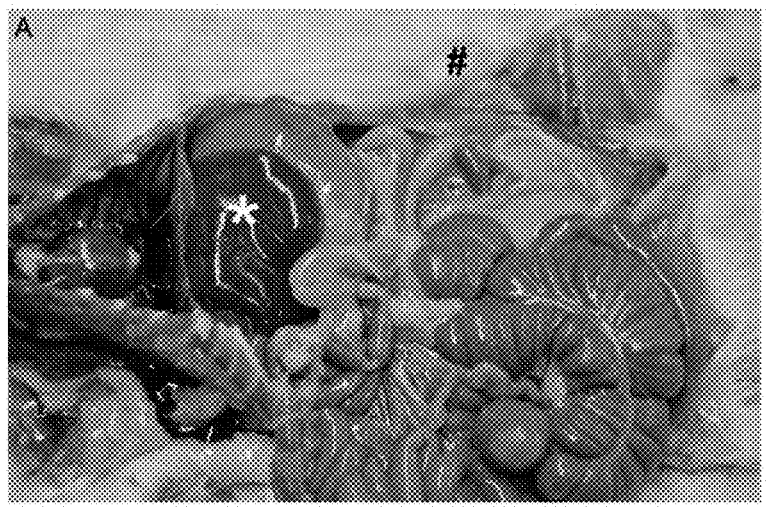
FIGS. 1A to 1E shows the gross pathology comparison of control guinea pigs (FIG. 1A) and Zaire Ebola virus (ZEBOV)-infected guinea pigs at terminus (FIG. 1B-1D).

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "Filoviruses" refers to viruses that generally cause acute hemorrhagic fever and high mortality. Filoviruses are single-stranded negative-sense RNA viruses, with a genome that includes seven proteins: four virion structural proteins (VP24, VP30, VP35, and VP40), a membrane-anchored glycoprotein (GP), a nucleoprotein (NP), and an RNA-dependent RNA polymerase (L). Currently, the Filoviridae family includes the three virus genera Ebolavirus, Marburgvirus, and Cuevavirus, which are the subject of the present invention.

Example 1

Ebola Viruses

Ebola viruses and the genomically related Marburg viruses are single-stranded, negative-sense, filamentous viruses in the family Filoviridae [1]. The genomes of these viruses contain 7 genes encoding a number of proteins, including nucleoprotein (NP), viral protein 35 (VP35), VP40, glycoprotein, VP30, VP24, and an RNA-dependent RNA polymerase. Filoviruses have been the cause of many sporadic outbreaks of severe hemorrhagic disease in humans and nonhuman primates (NHPs) throughout much of the area of endemicity in Central Africa, from which exportations have also led to outbreaks in more-developed regions. The current outbreak of Ebola hemorrhagic fever (EHF) occurring in West Africa is the largest documented filovirus outbreak in history. At the time of this writing, this outbreak has resulted in >50 times more human infections than any known past outbreak, with >21,000 cases and an estimated mortality of 50% [2]. Historically, filovirus outbreaks have remained relatively isolated to remote areas of Central Africa, which has likely contributed to the relatively rapid success in controlling spread. Conversely, the most recent outbreak was in a geographically connected, more-densely populated, and highly transient population, making this outbreak more of a global concern than ever before [3].

Development of countermeasures against filovirus infections has depended on the use of mice [4, 5], hamsters [6], and various strains of guinea pigs [7-9] as rodent models for screening prior to preclinical evaluation in the gold standard NHP models of filovirus infection [10, 11]. All filovirus rodent models have required adaptation prior to reaching uniformly lethality, whereas NHP models do not. Few of these small-animal models have recapitulated hallmark features of the disease course seen in humans or NHP, specifically the induction of coagulopathies and vascular leak syndromes. Importantly, few have demonstrated a consistent predictive value for any potential countermeasures against lethal filovirus challenge in NHPs.

The guinea pig and hamster are the only rodent models that currently use outbred animals presenting with coagulopathies more reflective of those seen in NHPs and humans. The hamster model is a relatively new model, and its predictive value has yet to be determined. Conversely, the guinea pig model has shown some success in predicting the efficacy of therapies, including small interfering RNA [12, 13] and antibody-based therapies [14, 15], in NHPs. Although some countermeasures have shown efficacy in mice, they unfortunately do not all correlate to efficacy in NHPs [16]. The reason for differences in the predictive value between rodent models of filovirus disease is unclear.

Detailed descriptions of EHF progression in guinea pigs to date have primarily used strain 13 guinea pigs [7]. While useful as an early model of EHF, this inbred guinea pig strain has demonstrated altered immune responsiveness and thus may not be representative of the heterogeneous immune responses of outbred hosts such as NHPs and humans [17, 18]. Further, the availability of this variety of guinea pig is limited, as very few breeding colonies exist. To address this problem, the inventors developed a uniformly lethal model of EHF in outbred guinea pigs. The inventors performed a temporal study to detail the events leading to death in ZEBOV-infected outbred guinea pigs and show that many of the hallmark features of EHF in humans and NHP are represented. To date, all filovirus rodent models have required genetic changes that ultimately have resulted in changes of 1 or more viral proteins. The inventors also show a comparative sequence analysis that with novel mutations that resulted from serial passage in guinea pigs and/or cell culture.

Virus Adaptation. Briefly, the starting material for adaptation was serum from Mayinga N'Seka, a nurse who died during the original outbreak of ZEBOV in 1976 in the country formerly known as Zaire [19]. The serum was amplified by 1 passage in Vero 76 cells (ATCC CRL-1587, ATCC). A group of inbred strain 13 guinea pigs was then challenged by intramuscular injection with approximately 6000 plaque-forming units (PFU) of the Vero culture fluid containing ZEBOV. Spleens from 2 animals were collected at day 7 after infection. Another group of inbred strain 13 guinea pigs was then challenged by intramuscular injection with approximately 6000 PFU of the pooled clarified 10% spleen homogenates from these 2 animals. This process was repeated for a total of 4 passages until uniform lethality was achieved in the inbred strain 13 guinea pigs. This Vero p1, inbred strain 13 guinea pig spleen p4 material was then amplified by 1 passage in Vero 76 cells. A group of outbred Hartley strain guinea pigs were then challenged by intraperitoneal injection with approximately 100 PFU of the Vero culture fluid containing the inbred strain 13 guinea pig adapted ZEBOV. Liver and spleen from one of these animals was harvested at day 7 after infection. Another group of inbred strain 13 guinea pigs was then challenged by intraperitoneal injection with approximately 50 PFU of the pooled clarified 10% liver and spleen homogenate from this animal. This process was repeated for a total of 3 passages until uniform lethality was achieved in the outbred Hartley strain guinea pigs. This Vero p1, inbred strain 13 guinea pig spleen p4, Vero p1, outbred guinea pig liver plus spleen p3 material was then amplified by 1 passage in Vero 76 cells to produce a seed stock. This seed stock produced uniform lethality in 18 of 18 outbred Hartley strain guinea pigs when animals were challenged by intraperitoneal injection with approximately 5000 PFU of the virus stock.

Detailed Zaire ebolavirus (ZEBOV) strain Mayinga guinea pig adapted virus methods and results.

Step 1. Starting material: Serum from Mayinga N'Seka, a nurse who died during the original outbreak of ZEBOV in 1976 in the former Zaire. The sample identification number was 057931. Methods and results: The serum was diluted 1:10 in Eagle's Minimum Essential Medium (EMEM) and inoculated on flasks of Vero 76 cells (ATCC CRL-1587) maintained in EMEM plus 10% FBS supplemented with glutamine and gentamicin. Culture fluid was collected from these flasks approximately 1 week later and titrated following conventional methods. This culture fluid is referred to as a Vero p1 seed stock.

Step 2. Starting material: Vero p1 seed stock produced from Step 1. Methods and results: A group of 7 inbred strain 13 guinea pigs were inoculated by intramuscular (i.m.) injection with approximately 6,000 plaque forming units (pfu) of the Vero p1 seed stock from step 1 above in a volume of approximately 0.2 ml. At the $7^{th}$ day after inoculation 2 of the 7 guinea pigs were euthanized and their spleens were harvested and homogenized in EMEM plus 10% FBS at a 10% weight to volume ratio. The clarified spleen homogenates were titrated to quantify infectious ZEBOV and these homogenates then served as the inoculum for additional inbred strain 13 guinea pigs in Step 3 below as uniform lethality was not achieved in the remaining 5 animals. This clarified 10% inbred strain 13 guinea pig pooled spleen homogenate is referred to as an inbred guinea pig p1 spleen homogenate (Vero p1, inbred strain 13 guinea pig spleen p1).

Step 3. Starting material: Clarified 10% inbred strain 13 guinea pig pooled p1 spleen homogenate from Step 2 (Vero p1, inbred strain 13 guinea pig spleen p1). Methods and results: A group of 7 inbred strain 13 guinea pigs were inoculated by i.m. injection with approximately 6,000 pfu of the clarified 10% spleen homogenates in a volume of approximately 0.2 ml. At the $7^{th}$ day after inoculation 2 of the 7 guinea pigs were euthanized and their spleens were harvested and homogenized in EMEM plus 10% FBS at a 10% weight to volume ratio. The clarified spleen homogenates were titrated to quantify infectious ZEBOV and these homogenates then served as the inoculum for additional inbred strain 13 guinea pigs in Step 4 below as uniform lethality was not achieved in the remaining 5 animals. This clarified 10% inbred strain 13 guinea pig pooled spleen homogenate is referred to as an inbred guinea pig p2 spleen homogenate (Vero p1, inbred strain 13 guinea pig spleen p2).

Step 4. Starting material: Clarified 10% inbred strain 13 guinea pig pooled p2 spleen homogenate from Step 3 (Vero p1, inbred strain 13 guinea pig spleen p2). Methods and results: A group of 7 inbred strain 13 guinea pigs were inoculated by i.m. injection with approximately 6,000 pfu of the clarified 10% spleen homogenates in a volume of approximately 0.2 ml. At the $7^{th}$ day after inoculation 2 of the 7 guinea pigs were euthanized and their spleens were harvested and homogenized in EMEM plus 10% FBS at a 10% weight to volume ratio. The clarified spleen homogenates were titrated to quantify infectious ZEBOV and these homogenates then served as the inoculum for additional inbred strain 13 guinea pigs in Step 5 below as uniform lethality was not achieved in the remaining 5 animals. This clarified 10% inbred strain 13 guinea pig pooled spleen homogenate is referred to as an inbred guinea pig p3 spleen homogenate (Vero p1, inbred strain 13 guinea pig spleen p3).

Step 5. Starting material: Clarified 10% inbred strain 13 guinea pig pooled p3 spleen homogenate from Step 4 (Vero p1, inbred strain 13 guinea pig spleen p3). Methods and results: A group of 7 inbred strain 13 guinea pigs were inoculated by i.m. injection with approximately 6,000 pfu of the clarified 10% spleen homogenates in a volume of approximately 0.2 ml. At the $7^{th}$ day after inoculation 2 of the 7 guinea pigs were euthanized and their spleens were harvested and homogenized in EMEM plus 10% FBS at a 10% weight to volume ratio for potential future use. This clarified 10% inbred strain 13 guinea pig pooled spleen homogenate is referred to as an inbred guinea pig p4 spleen homogenate (Vero p1, inbred strain 13 guinea pig spleen p4). As uniform lethality was achieved in the remaining 5 inbred strain 13 guinea pigs further passaging was stopped at this point.

Step 6. Starting material: Clarified 10% inbred strain 13 guinea pig pooled p4 spleen homogenate from Step 5 (Vero p1, inbred strain 13 guinea pig spleen p4.) Methods and results: The p4 inbred strain 13 guinea pig spleen homogenate from Step 5 was diluted 1:10 in EMEM and inoculated on flasks of Vero 76 cells (ATCC CRL-1587) maintained in EMEM plus 10% FBS supplemented with glutamine and gentamicin. Culture fluid was collected from these flasks approximately 8 days later and titrated following conventional methods. This culture fluid is referred to as a Vero p1, inbred guinea pig spleen p4, Vero p1 seed stock.

Step 7. Starting material: Vero p1, inbred guinea pig spleen p4, Vero p1 seed stock from Step 6. Methods and results: A group of 6 outbred Hartley guinea pigs were inoculated by intraperitoneal (i.p.) injection with approximately 100 pfu of the Vero p1, inbred guinea pig spleen p4, Vero p1 seed stock from Step 6 in a volume of approximately 0.5 ml. At the $7^{th}$ day after inoculation 2 of the 6 outbred Hartley guinea pigs were euthanized and their livers and spleens were harvested and homogenized in EMEM plus 10% FBS at a 10% weight to volume ratio. The liver and spleen homogenates were titrated to quantify infectious ZEBOV and an equal pool of liver and spleen homogenates from one of these two animals then served as the inoculum for additional outbred Hartley guinea pigs in Step 8 below as uniform lethality was not achieved in the remaining 4 animals. This clarified 10% outbred Hartley guinea pig pooled liver and spleen homogenate is referred to as an outbred guinea pig p1 liver+spleen homogenate (Vero p1, inbred guinea pig spleen p4, Vero p1, outbred guinea pig liver+spleen p1).

Step 8. Starting material: Clarified 10% outbred Hartley guinea pig p1 liver and spleen homogenate from Step 7 (Vero p1, inbred guinea pig spleen p4, Vero p1, outbred guinea pig liver+spleen p1). Methods and results: A group of 6 outbred Hartley guinea pigs was inoculated by i.p. injection with approximately 50 pfu in approximately 0.5 ml of the clarified and pooled 10% liver and spleen homogenate from Step 7. At the $7^{th}$ day after inoculation 2 of the 6 outbred Hartley guinea pigs were euthanized and their livers and spleens were harvested and homogenized in EMEM plus 10% FBS at a 10% weight to volume ratio. The liver and spleen homogenates were titrated to quantify infectious ZEBOV and an equal pool of liver and spleen homogenates from both of these two animals then served as the inoculum for additional outbred Hartley guinea pigs in Step 9 below as uniform lethality was not achieved in the remaining 4 animals. This clarified 10% outbred Hartley guinea pig pooled liver and spleen homogenate is referred to as an outbred guinea pig p2 liver+spleen homogenate (Vero p1, inbred guinea pig spleen p4, Vero p1, outbred guinea pig liver+spleen p2).

Step 9. Starting material: Clarified 10% outbred Hartley guinea pig p2 liver and spleen homogenate from Step 8 (Vero p1, inbred guinea pig spleen p4, Vero p1, outbred guinea pig liver+spleen p2). Methods and results: A group of 6 outbred Hartley guinea pigs was inoculated by i.p. injection with approximately 250 pfu in approximately 0.5 ml of the clarified and pooled 10% liver and spleen homogenate from Step 8. At the $7^{th}$ day after inoculation 2 of the 6 outbred Hartley guinea pigs were euthanized and their livers and spleens were harvested and homogenized in EMEM plus 10% FBS at a 10% weight to volume ratio for potential future passage. This clarified 10% outbred Hartley guinea pig pooled liver and spleen homogenate is referred to as an outbred guinea pig p3 liver+spleen homogenate (Vero p1, inbred guinea pig spleen p4, Vero p1, outbred guinea pig liver+spleen p3). As uniform lethality was achieved in the remaining 4 outbred Hartley guinea pigs further passaging was stopped at this point.

Step 10. Starting material: Clarified 10% outbred Hartley guinea pig p2 liver and spleen homogenate from Step 10 (Vero p1, inbred guinea pig spleen p4, Vero p1, outbred guinea pig liver+spleen p3). Methods and results: The p3 outbred guinea pig liver+spleen homogenate from Step 9 was diluted 1:10 in EMEM and inoculated on flasks of Vero 76 cells (ATCC CRL-1587) maintained in EMEM plus 10% FBS supplemented with glutamine and gentamicin. Culture fluid was collected from these flasks approximately 8 days later and titrated following conventional methods. This culture fluid is referred to as a Vero p1, inbred guinea pig spleen p4, Vero p1, outbred guinea pig liver+spleen p3, Vero p1 seed stock. The titer of this seed stock is approximately 2.95×10^5 pfu/ml.

Step 11. Starting material: Vero p1, inbred guinea pig spleen p4, Vero p1, outbred guinea pig liver+spleen p3, Vero p1 from Step 10. Methods and results: Virulence of the seed stock from Step 10 was confirmed in a group of several different studies as follows: 1) a total of 5 outbred Hartley guinea pigs were inoculated by i.p. injection with a target does of approximately 10,000 pfu of the Vero p1, inbred guinea pig spleen p4, Vero p1, outbred guinea pig liver+spleen p3, Vero p1 from Step 10 in a volume of approximately 0.5 ml; 2) a total of 8 outbred Hartley guinea pigs were inoculated by i.p. injection with a target does of approximately 2,000 pfu of the Vero p1, inbred guinea pig spleen p4, Vero p1, outbred guinea pig liver+spleen p3, Vero p1 from Step 10 in a volume of approximately 0.5 ml; 3) a group of 5 outbred Hartley guinea pigs were given a whole body aerosol exposure to a target does of approximately 1,000 pfu of the Vero p1, inbred guinea pig spleen p4, Vero p1, outbred guinea pig liver+spleen p3, Vero p1 from Step 10. All 18 animals succumbed between days 8 and 9 after exposure to this seed stock regardless of challenge dose or route confirming the uniform lethality in outbred Hartley guinea pigs caused by this seed stock.

Step 12. Starting material: Vero p1, inbred guinea pig spleen p4, Vero p1, outbred guinea pig liver+spleen p3, Vero p1 from Step 10. Methods and results: Approximately 1 ml of the Vero p1, inbred guinea pig spleen p4, Vero p1, outbred guinea pig liver+spleen p3, Vero p1 from Step 10 was removed from the seed vial and placed in ~5 ml of Trizol LS and vortexed 3 times and allowed to sit for 10 minutes. The 6 ml were then placed into 2 separate 3 ml Nunc cryo-vials for removal from the BSL-4. RNA was isolated from the Trizol LS/sample mixture using Zymo Research Direct-zol RNA mini-prep per manufacturer's instructions. Approximately 150 ng of purified RNA were used to make cDNA using the NuGen Ovation RNA-seq 2.0 kit ultimately for the preparation of the double stranded DNA library using Encore Ion Torrent library prep kit. Sequencing was performed by the UTMB Molecular Core on the Ion Torrent using 318-v2 deep sequencing chips. Sequence analysis was performed using DNA Star Seqman NGen software based on paired-end analysis of 100 bp overlaps. Sequencing results were compared to GenBank sequences for the starting material and are shown below.

UTMB Geisbert ZEBOV-Mayinga Guinea Pig Adapted Strain (compared to Accession No. AF086833.2)

| Nucleotide | Base Change | Result | Gene |
|---|---|---|---|
| 652 | A > G | Silent | NP |
| 2192 | G > A | A575T | NP |
| 2409 | C > A | S647Y | NP |
| 5219 | U > C | Silent | VP40 |
| 7668 | U > C | I544T | GP |
| 10258 | G > A |  | Non-coding |
| 10420 | C > U | L26F | VP24 |
| 10768 | A > G | K142E | VP24 |

Sudan ebolavirus (SEBOV) strain Boniface guinea pig adapted virus methods and results.

Step 1. Starting material: Culture fluid from Vero E6 cells containing the Boniface strain of SEBOV provided by Dr. Thomas Ksiazek (UTMB). The passage history of the virus seed stock provided is as follows: Serum from a patient named Boniface collected during the original outbreak of SEBOV in 1976 in Sudan. The sample identification number was 811112. The patient serum was passed four times on monolayers of Vero 76 cells and three times on monolayers of Vero E6 cells. This virus stock is referred to as Vero p4, Vero E6 p3.

Methods and Results:

A group of 6 outbred Hartley guinea pigs were inoculated by intraperitoneal (i.p.) injection with a target dose of approximately 10,000 pfu of the Vero p4, Vero E6 seed stock in a volume of approximately 0.5 ml. At the $7^{th}$ day after inoculation 2 of the 6 outbred Hartley guinea pigs were euthanized and their livers and spleens were harvested and homogenized in EMEM plus 10% FBS at a 10% weight to volume ratio. The liver and spleen homogenates were titrated to quantify infectious SEBOV and an equal pool of liver and spleen homogenates from both of these animals then served as the inoculum for additional outbred Hartley guinea pigs in Step 2 below as uniform lethality was not achieved in the remaining 4 animals. This clarified 10% outbred Hartley guinea pig pooled liver and spleen homogenate is referred to as an outbred guinea pig p1 liver+spleen homogenate (Vero p4, Vero E6p3, outbred guinea pig liver+spleen p1).

Step 2. Starting material: Clarified 10% outbred Hartley guinea pig pooled p1 spleen homogenate from Step 1 (Vero p4, Vero E6p3, outbred guinea pig liver+spleen p1).

Methods and results: A group of 6 outbred Hartley guinea pigs was inoculated by i.p. injection with a target dose of approximately 50 pfu in approximately 0.5 ml of the clarified and pooled 10% liver and spleen homogenate from Step 1. At the $5^{th}$ day after inoculation 2 of the 6 guinea pigs were euthanized and their livers and spleens were harvested and homogenized in EMEM plus 10% FBS at a 10% weight to volume ratio. The clarified liver and spleen homogenates were titrated to quantify infectious SEBOV and these homogenates then served as the inoculum for additional outbred Hartley guinea pigs in Step 3 below as uniform lethality was not achieved in the remaining 4 animals. This clarified 10% outbred Hartley guinea pig pooled liver and spleen homogenate is referred to as an outbred guinea pig p2 liver+spleen homogenate (Vero p4, Vero E6p3, outbred guinea pig liver+spleen p2).

Step 3. Starting material: Clarified 10% outbred Hartley guinea pig pooled p2 spleen homogenate from Step 1 (Vero p4, Vero E6p3, outbred guinea pig liver+spleen p2). Methods and results: A group of 6 outbred Hartley guinea pigs was inoculated by i.p. injection with a target dose of approximately 10,000 pfu in approximately 0.5 ml of the clarified and pooled 10% liver and spleen homogenate from Step 2. At the 5$^{th}$ day after inoculation 2 of the 6 guinea pigs were euthanized and their livers and spleens were harvested and homogenized in EMEM plus 10% FBS at a 10% weight to volume ratio. An additional animal from another study with animals inoculated by the same methods succumbed on day 11 after virus exposure and the liver and spleen from this animal was also harvested and homogenized in EMEM plus 10% FBS at a 10% weight to volume ratio. The clarified liver and spleen homogenates from all three animals were titrated to quantify infectious SEBOV and these equally pooled homogenates then served as the starting material for a virus seed stock. This clarified 10% outbred Hartley guinea pig pooled liver and spleen homogenate is referred to as an outbred guinea pig p3 liver+spleen homogenate (Vero p4, Vero E6p3, outbred guinea pig liver+spleen p3).

Step 4. Starting material: Clarified 10% outbred Hartley guinea pig pooled p3 liver and spleen homogenate from Step 3 (Vero p4, Vero E6p3, outbred guinea pig liver+spleen p3). Methods and results: The p3 outbred Hartley guinea pig liver and spleen homogenate from Step 4 was diluted 1:10 in EMEM and inoculated on flasks of Vero 76 cells (ATCC CRL-1587) maintained in EMEM plus 10% FBS supplemented with glutamine and gentamicin. Culture fluid was collected from these flasks approximately 8 days later and titrated following conventional methods. This culture fluid is referred to as a Vero p4, Vero E6p3, outbred guinea pig liver+spleen p3, Vero p1 seed stock. The titer of this seed stock is approximately $1.175 \times 10^7$ pfu/ml.

Step 5. Starting material: Vero p4, Vero E6p3, outbred guinea pig liver+spleen p3, Vero p1 seed stock from Step 4. Methods and results: Virulence of the seed stock from Step 4 was assessed in a group of outbred Hartley guinea pigs and a group of inbred strain 13 guinea pigs as follows: 1) a total of 6 outbred Hartley guinea pigs were inoculated by i.p. injection with a target dose of approximately 10,000 pfu of the Vero p4, Vero E6p3, outbred guinea pig liver+spleen p3, Vero p1 seed stock from Step 4 in a volume of approximately 0.5 ml; 2) a total of 5 inbred strain 13 guinea pigs were inoculated by i.p. injection with a target dose of approximately 10,000 pfu of the Vero p4, Vero E6p3, outbred guinea pig liver+spleen p3, Vero p1 seed stock from Step 4 in a volume of approximately 0.5 ml. Half of the outbred Hartely guinea pigs succumbed to challenge with this seed stock while the seed stock cause uniform lethality in the inbred strain 13 guinea pigs with all of the inbred strain 13 guinea pigs succumbing between days 10 and 14 after exposure. These results demonstrate a uniformly lethal model of SEBOV infection in inbred strain 13 guinea pigs and a partially lethal model of SEBOV infection in outbred Hartley guinea pigs.

Step 6. Starting material: Vero p4, Vero E6p3, outbred guinea pig liver+spleen p3, Vero p1 seed stock from Step 4. Methods and results: Approximately 1 ml of Vero p4, Vero E6p3, outbred guinea pig liver+spleen p3, Vero p1 seed stock from Step 4 was removed from the seed vial and placed in ~5 ml of Trizol LS and vortexed 3 times and allowed to sit for 10 minutes. The 6 ml were then placed into 2 separate 3 ml Nunc cryo-vials for removal from the BSL-4. RNA was isolated from the Trizol LS/sample mixture using Zymo Research Direct-zol RNA mini-prep per manufacturer's instructions. Approximately 150 ng of purified RNA were used to make cDNA using the NuGen Ovation RNA-seq 2.0 kit ultimately for the preparation of the double stranded DNA library using Encore Ion Torrent library prep kit. Sequencing was performed by the UTMB Molecular Core on the Ion Torrent using 318-v2 deep sequencing chips. Sequence analysis was performed using DNA Star Seqman NGen software based on paired-end analysis of 100 bp overlaps. Sequencing results were compared to GenBank sequences for the starting material and are shown below.

UTMB Geisbert SEBOV-Boniface Guinea Pig Adapted Strain (compared to Accession No. FJ968794.1)

| Nucleotide | Base Change | Result | Gene |
|---|---|---|---|
| 2640 | A > G | Q728R | NP |
| 6286 | U > G | F97V | GP |
| 8150 | C > A | | Non-coding |
| 10363 | U > C | V22A | VP24 |
| 12751 | C > U | S406F | L |
| 15364 | A > G | H1277R | L |
| 18303 | A > G | | Non-coding |

Animal Inoculation. Animal studies were completed under biosafety level 4 (BSL-4) biocontainment at the Galveston National Laboratory and were approved by the University of Texas Medical Branch Institutional Laboratory Animal Care and Use Committee, in accordance with state and federal statutes and regulations relating to experiments involving animals, and the University of Texas Medical Branch Institutional Biosafety Committee. Female outbred Hartley strain guinea pigs (weight, approximately 351-400 g; age, approximately 5-6 weeks) were acclimatized for approximately 1 week prior to ZEBOV challenge. Thirty-six animals were divided into 9 groups of 4 animals per group (8 experimental groups and 1 control group). Individual animals were infected with approximately 5000 PFU in 0.5 mL of guinea pig-adapted ZEBOV-Mayinga or mock infected (using Hank's balanced salt solution with 2% fetal bovine serum) by intraperitoneal injection.

Necropsy. Guinea pigs from each ZEBOV-infected experimental group of animals was euthanized daily for 8 days after infection or when indicated by protocol euthanasia criteria (n=4/group/day). This terminal time point shall hereafter be referred to as terminus. Clinical signs, weights, and transponder-mediated temperatures were recorded daily up to the point of euthanasia. Prior to necropsy, whole-blood specimens, plasma specimens (collected in tubes containing ethylenediaminetetraacetic acid (EDTA)), and citrated plasma samples were collected by cardiac puncture for hematologic analysis, a serum/plasma biochemical assay, and viremia determination. Gross pathology findings were documented, and portions of select tissues were aseptically removed and frozen at −70° C. for virus infectivity assays. The following tissues were collected on all animals for histologic and immunohistochemical analyses: liver, spleen, kidney, adrenal gland, lung, brain, lymph nodes (axillary, inguinal, mesenteric, and mandibular), salivary gland, trachea, esophagus, stomach, duodenum, ileocecal junction, colon, urinary bladder, reproductive tract, pancreas, haired skin, and heart.

Histologic and Immunohistochemical Analyses. Selected tissues were fixed in formalin for at least 21 days in the BSL-4 facility. Specimens were then removed from the BSL-4 facility, processed in a BSL-2 facility by using conventional procedures, and embedded in paraffin for sectioning for histopathologic analysis.

Hematologic Analysis, Serum Biochemistry Analysis. Measurement of Proinflammatory Markers, and Determination of Coagulation Parameters. Complete blood counts, coagulation dynamics, and serum analysis of blood chemistry were performed on blood, serum, or plasma specimens collected from each experimental animal. Analyses of select cytokines, coagulation factors, eicanosoids, and nitric oxide measured in serum or plasma specimens were also performed.

Virus Isolation. Determination of infectious virus in plasma, spleen, liver, kidney, adrenal gland, pancreas, lung, and brain was performed using standard plaque assays.

Statistics Statement. Conducting animal studies in a BSL-4 facility severely restricts the number of animal subjects, the volume of biological samples and the ability to repeat assays independently and thus limits the power of statistical analyses. Consequently, data are presented as the mean values calculated from replicate samples, not replicate assays, and error bars represent the standard deviation across replicates.

Virus Adaptation and Sequence Analysis. Sequence comparison of guinea pig-adapted ZEBOV-Mayinga with the prototype sequence (accession number AF086833.2) revealed nucleotide substitutions that resulted in 2 amino acid changes in NP and single changes in VP40 and glycoprotein. Two amino acid changes in VP24 were also identified, of which the L26F mutation has previously been identified as sufficient to confer virulence in guinea pigs [20] (Table 1). One nucleotide substitution was discovered in the noncoding region, and 1 silent mutation was identified in the gene encoding NP. The resulting mutations may have been acquired during the consecutive passages in guinea pigs and/or 2 passages in Vero 76 cells during seed production.

TABLE 1

Genetic Mutations Detected in Guinea Pig-Adapted Zaire Ebola virus (ZEBOV) Strain Mayinga

| Nucleotide | Base Change | Result | Gene |
| --- | --- | --- | --- |
| 652 | A > G | Silent | Nucleoprotein |
| 2192 | G > A | A575T | Nucleoprotein |
| 2409 | C > A | S647Y | Nucleoprotein |
| 5219 | U > C | Silent | Viral protein 40 |
| 7668 | U > C | I544T | Glycoprotein |
| 10258 | G > A | . . . | Noncoding |
| 10420 | C > U | L26F | Viral protein 24 |
| 10768 | A > G | K142E | Viral protein 24 |

Genomic sequence of ZEBOV-Mayinga guinea pig-adapted strain was compared to reference sequence for wild type ZEBOV-Mayinga (Accession number: AF086833.2).

Virus Titers in Blood and Tissue Specimens. Plasma viremia was first detected on day 2 at 3.0 log 10 PFU/mL. Mean peak viremia of 5.3 log 10 PFU/mL was recorded on day 3 and maintained at elevated levels through the remaining time points. Infectious virus was recovered beginning on day 2 from all tissues except brain; recovery was negative for all time points at which brains were collected. Early in infection, spleens contained higher mean titers than other tissues, suggesting that spleen is likely an early site of infection, as previously reported [7, 21]. Mean infectivity titers in all organs steadily increased to peak levels on postinfection days 7 and 8 (Table 2).

TABLE 2

Virus Burden in Plasma and Tissues

| Tissue | Day 1 | Day 2 | Day 3 | Day 4 | Day 5 | Day 6 | Day 7 | Day 8 |
| --- | --- | --- | --- | --- | --- | --- | --- | --- |
| Brain | . . . | . . . | . . . | . . . | . . . | . . . | . . . | . . . |
| Spleen | . . . | 3.5 ± 0.2 | 3.7 ± 0.2 | 3.2 ± 0.5 | 3.5 ± 0.4 | 3.3 ± 0.6 | 3.5 ± 0.6 | 3.2 ± 0.6 |
| Pancreas | . . . | 2.3 ± 0.2 | 2.3 ± 0.0 | 2.9 ± 0.0 | 2.8 ± 0.1 | 3.3 ± 0.4 | 3.2 ± 0.5 | 3.4 ± 1.0 |
| Lung | . . . | 2.3 ± 0.5 | 2.8 ± 0.3 | 3.3 ± 0.5 | 3.8 ± 1.0 | 4.1 ± 0.9 | 3.7 ± 1.4 | 4.6 ± 0.8 |
| Kidney | . . . | 2.2 ± 0.2 | 3.4 ± 1.3 | 2.6 ± 0.4 | 3.1 ± 0.3 | 2.8 ± 0.3 | 2.9 ± 0.5 | 2.6 ± 0.7 |
| Liver | . . . | 2.5 ± 0.0 | 4.2 ± 0.4 | 3.3 ± 0.1 | 3.1 ± 0.9 | 3.3 ± 0.7 | 4.2 ± 1.1 | 4.3 ± 0.9 |
| Adrenal | . . . | 2.7 ± 0.7 | 4.0 ± 0.2 | 3.5 ± 0.2 | 3.2 ± 0.3 | 3.5 ± 0.1 | 4.2 ± 0.4 | 4.4 ± 0.6 |
| Plasma | . . . | 3.0 ± 0.4 | 5.3 ± 0.5 | 4.1 ± 1.4 | 3.6 ± 0.7 | 2.8 ± 0.0 | 3.9 ± 2.1 | 1.9 ± 0.0 |

Data are mean log 10 plaque-forming units/mL±SD measured from guinea pig tissue homogenates (10% wt/vol) from Guinea pigs inoculated with GPA EBOV-ZAIRE: MAYINGA.

Figure 1B:
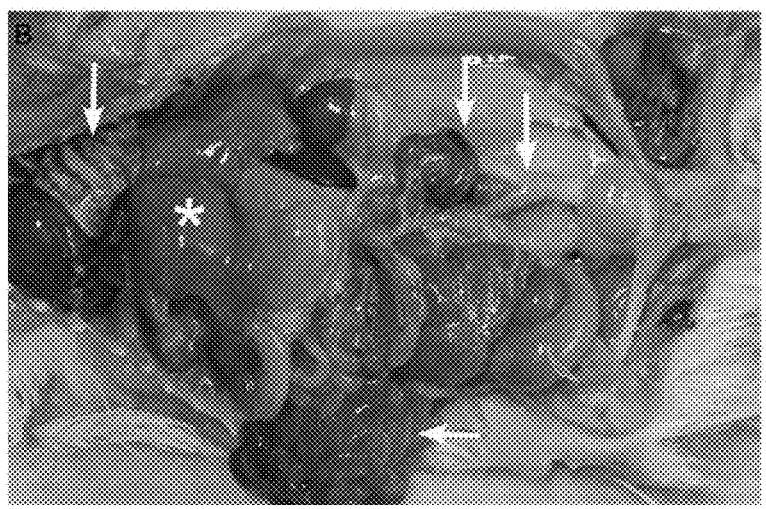
Figure 1C:
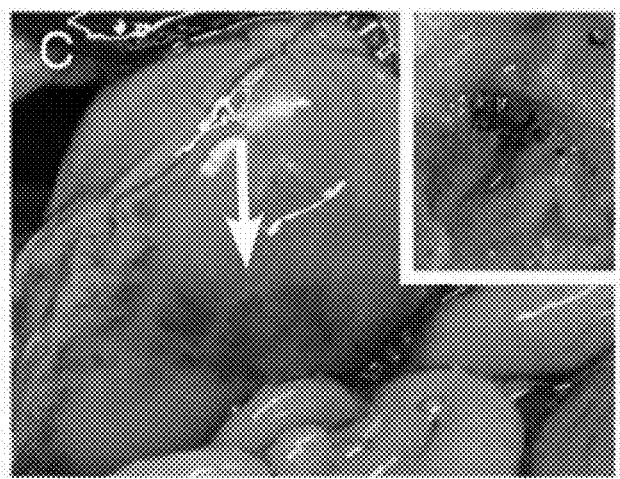
Figure 1D:
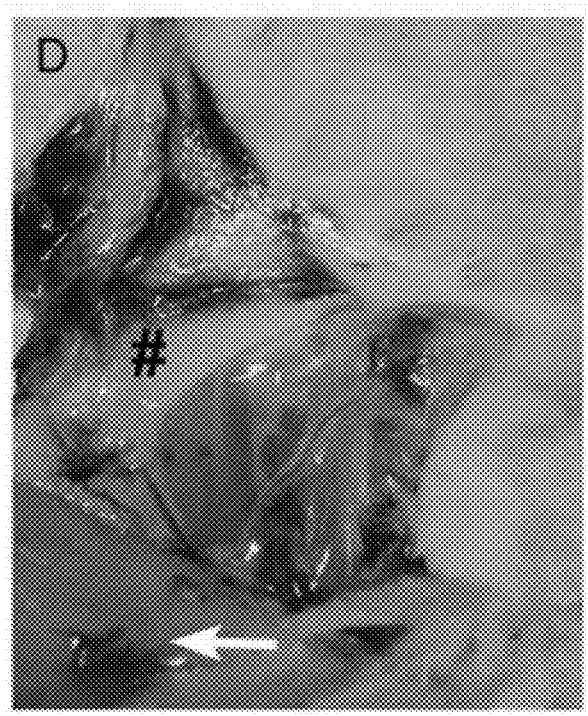
Figure 1E:
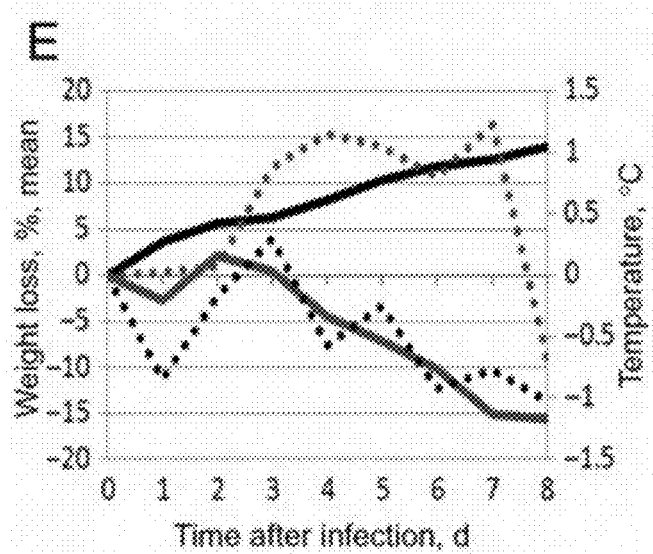

Gross Pathology. No significant gross lesions were present in the mock-infected control guinea pigs (FIG. 1A). Gross lesions present at necropsy of ZEBOV-infected guinea pigs began on day 3 and progressed in severity over the course of the study. The most significant gross lesions included splenic mottling with enlargement, hepatic reticulation with progressive pallor, lymphadenomegaly, interstitial pneumonia, multiorgan serosal and mucosal congestion and/or hemorrhage, and gastric ulceration (FIG. 1B-D). Mean changes in weight and temperature were collected for control and terminal guinea pigs. Beginning on day 3, ZEBOV infected guinea pigs had progressive weight loss (mean loss, up to 16% of body mass) and increases in body temperature (maintaining an average of 1° C. greater than normal, followed rapidly by hypothermia). Control animals did not experience weight loss or changes in body temperature over the course of the study (FIG. 1E).

Histopathologic and Immunohistochemical Findings. Histopathologic lesions and immunoreactivity for Ebola VP40 antigen among infected guinea pigs were most apparent by day 3, with the severity of lesions increasing over the duration of the study. No significant histopathologic lesions or immunoreactivity for Ebola antigen or fibrin was observed in any of the examined negative control guinea pig tissues.

Figure 2A:
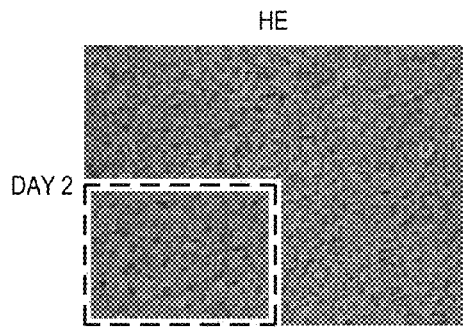
FIGS. 2A to 2J show: Hematoxylin-eosin staining (HE.
Figure 2F:
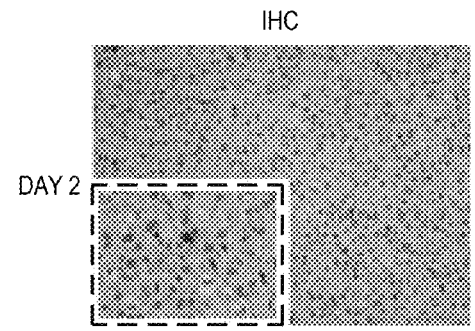
Figure 2B:
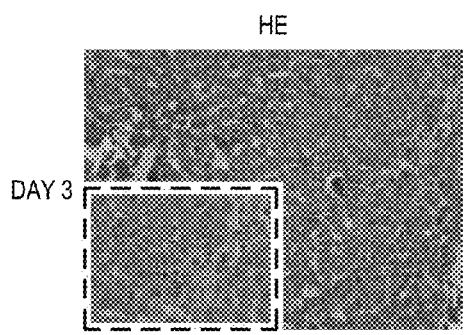
Figure 2G:
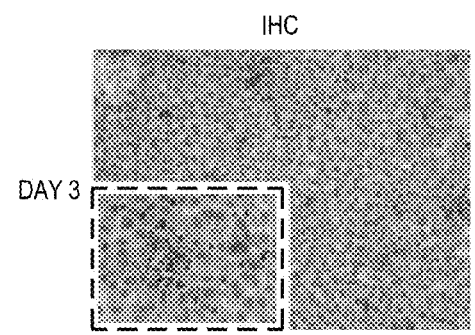
Figure 2C:
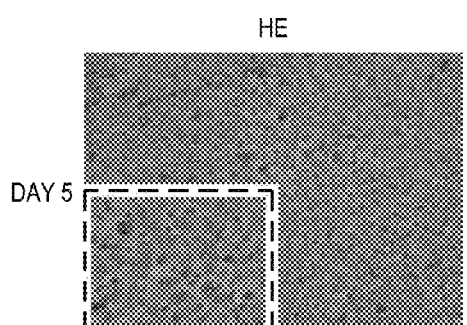
Figure 2H:
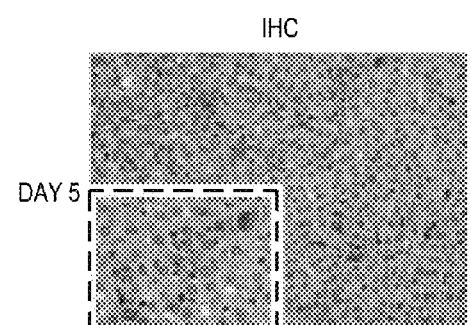
Figure 2D:
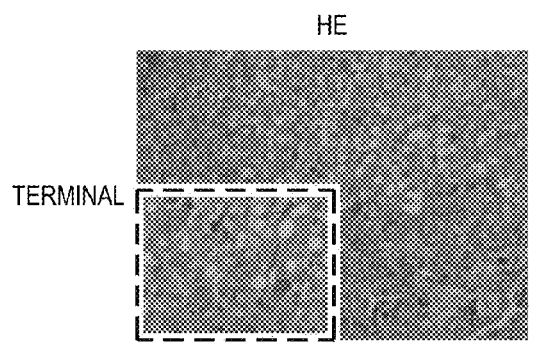
Figure 2I:
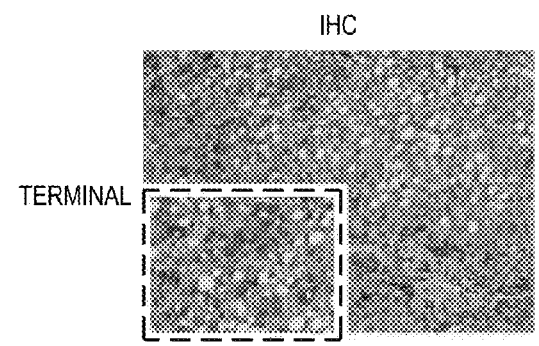
Figure 2E:
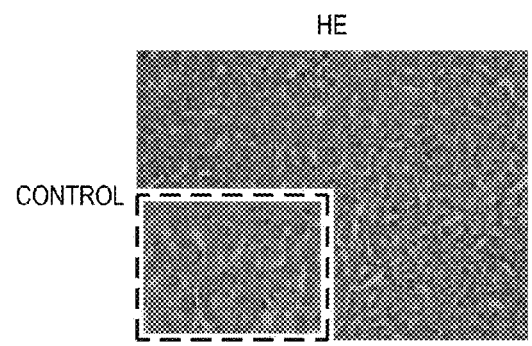
Figure 2J:
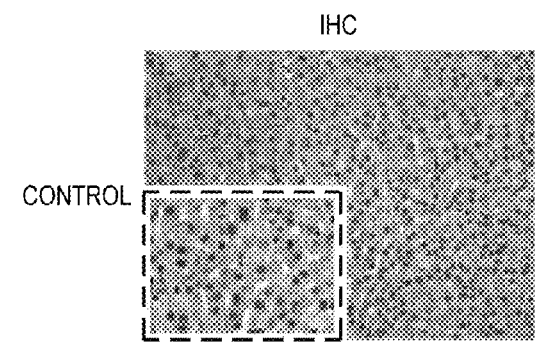
Figure 3A:
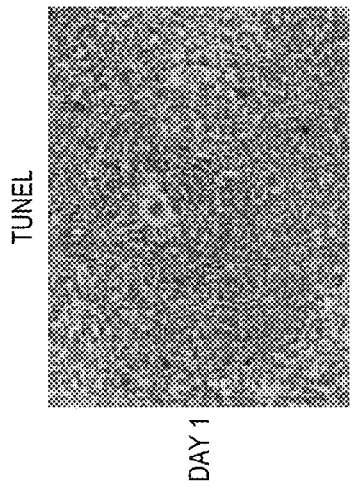
FIGS. 3A to 3O show: Hematoxylin-eosin staining (HE) (FIG. 3A, FIG. 3D, FIG. 3G, FIG. 3J, and FIG. 3M) and corresponding anti-Ebola virus immunohistochemical staining (FIG. 3B, FIG. 3E, FIG. 3H, FIG. 3K, and FIG. 3N) and TUNEL immunohistochemical staining (FIG. 3C, FIG. 3F, FIG. 3I, FIG. 3L, and FIG. 3O) of Zaire Ebola virus (ZEBOV)-infected guinea pig spleen, by day after infection, and control guinea pig spleen. All images are 20 times the original magnification. Infected spleen, day 1: no significant lesions (NSL.
Figure 3B:
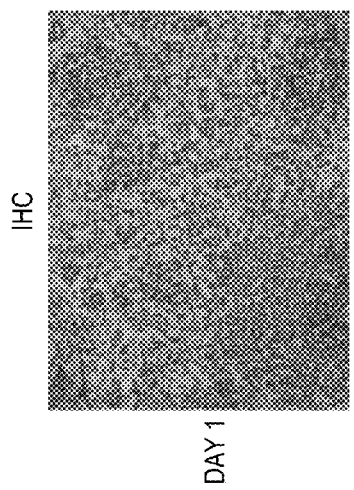
Figure 3C:
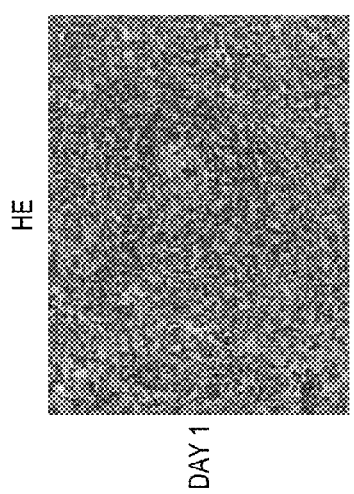
Figure 3D:
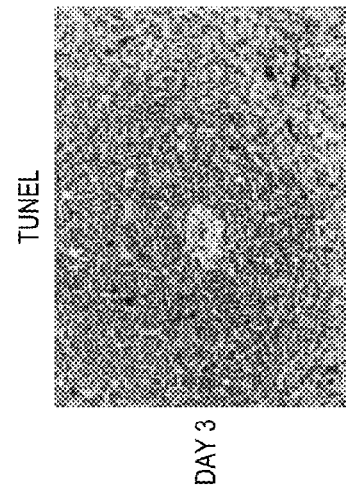
Figure 3E:
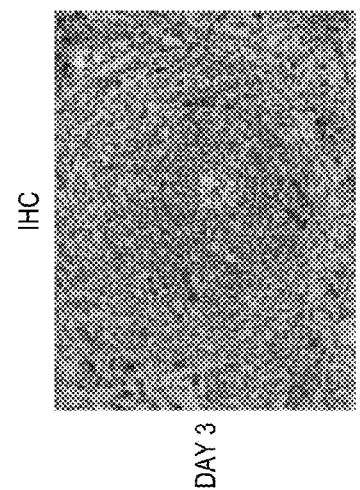
Figure 3F:
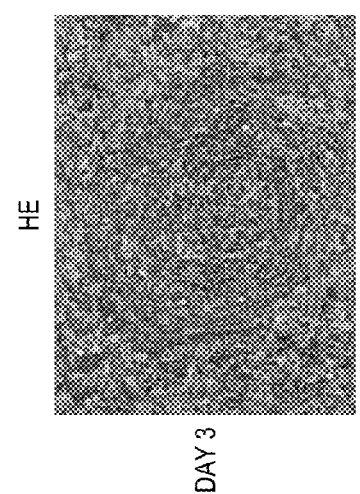
Figures 3M, 3N, 3O:
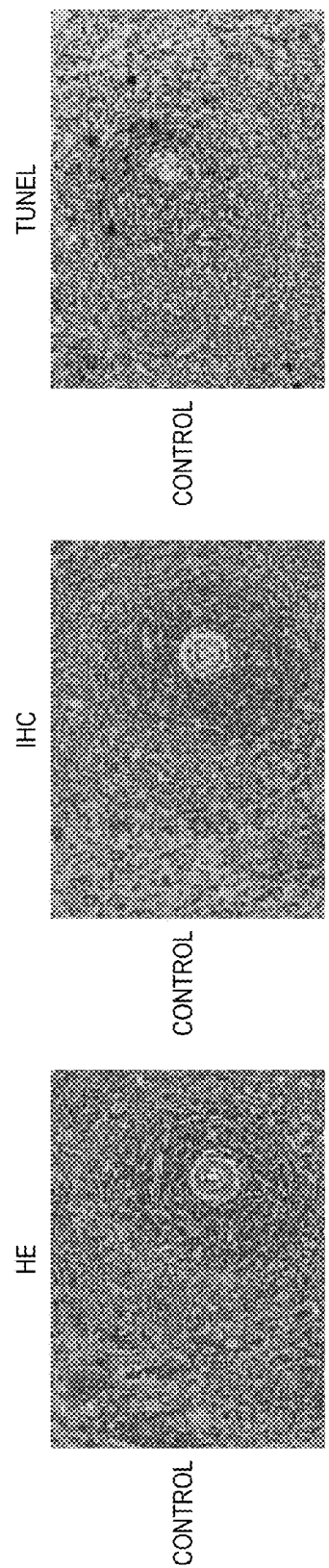

Liver. Ebola VP40 antigen-positive Kupffer cells were present on day 1 (2 of 4 animals) and 2 (4 of 4; FIG. 2F), yet no significant hepatocellular lesions were observed on hematoxylin-eosin (HE)-stained sections. Progressive hepatocellular vacuolation, degeneration/necrosis, and sinusoidal leukocytosis were observed on HE-stained sections in all animals (24 of 24) on days 3, 4, 5, 6, and 7 and at terminus (FIG. 2B-D). Additionally, Councilman bodies and eosinophilic, intracytoplasmic viral inclusion bodies were present on day 4 through terminus (20 of 20 animals). Hepatocellular mineralization associated with regions of degeneration and necrosis was increasingly evident starting on day 5 through terminus (12 of 16 animals). All infected animals (24 of 24), starting at day 3 through terminus, had Ebola antigen in Kupffer cells and individualized hepatocytes with progressive coalescing clusters of positive hepatocytes (FIG. 2G-I).

Spleen. Rare Ebola VP40 antigen-positive mononuclear cells within the red pulp were present on day 1 (4 of 4 animals; FIG. 3B), yet no significant lesions were observed on HE-stained sections. On day 2, increased numbers of EBOV-positive mononuclear cells were present in the red pulp, accompanied by hypercellularity and congestion (4 of 4 animals). At day 3, EBOV immunoreactivity peaked, with clusters of mononuclear cells present within the red and white pulp (4 of 4 animals; FIG. 3E). All animals (20 of 20), beginning on day 4 and continuing through day 8, had progressive lymphocyte depletion with tingible body macrophages within the white pulp and immunoreactive mononuclear cells that plateaued at day 4.

TUNEL staining of apoptotic populations within the splenic germinal centers increased over time, with peak intensity at day 5 (FIG. 3I). Positive immunoreactivity for fibrin was scattered throughout the red pulp and clustered within the marginal zone of the germinal centers in ZEBOV-infected guinea pigs (FIG. 4C).

Lymphoid Tissues. Mononuclear cells positive for Ebola VP40 antigen were rare within the subcapsular and medullary sinuses of the mandibular lymph node and appeared on day 2 (2 of 4 animals), yet no significant lesions were observed on HE-stained sections. On day 3, immunoreactive mononuclear cells within the subcapsular and medullary sinuses of the mandibular, axillary, and inguinal lymph nodes (4 of 4, 1 of 4, and 4 of 4 animals, respectively) were present, with increased numbers of immunoreactive cells at day 4 through terminus in all animals (20 of 20). Hemorrhage in the subcapsular and medullary sinuses was observed in inguinal lymph nodes on days 4 and 6 (2 of 4 and 2 of 4 animals, respectively). Lymphocyte degeneration and necrosis was observed in the mandibular lymph node on days 5, 6, and 7 and terminus (1 of 4, 1 of 4, 4 of 4, and 1 of 4 animals, respectively) and in the inguinal lymph node on day 7 and terminus (4 of 4 and 2 of 4, respectively). Ebola antigen-positive mononuclear cells within the medulla of the thymus were present starting on day 4 through terminus (17 of 20 animals). Beginning on day 6 and continuing through the study, clusters of immunoreactive interstitial cells of the salivary gland were present (1 of 2, 3 of 4, and 3 of 4 animals, respectively). No significant lesions were observed on HE-stained sections of axillary lymph node, thymus, and salivary gland.

Adrenal Gland. Ebola VP40 antigen-positive stellate interstitial cells were first present within the medullary region, starting on day 3 (1 of 4 animals), and, by day 4 through terminus, were present within stellate interstitial cells of all regions of the adrenal gland and cortical cells (18 of 20). This corresponded with cortical medullary hemorrhage, starting on day 3 through terminus (21 of 24 animals), and with cortical necrosis at terminus (4/4).

Gastrointestinal Tract. Ebola VP40 antigen in scattered mononuclear interstitial cells within the pancreas, often surrounding small vessels, was present on day 3 through terminus (19 of 24), yet no significant lesions were observed on HE-stained sections. Scattered mononuclear cells within the lamina propria of the stomach, duodenum, and ileocecal junction were present starting on day 4 through terminus (19 of 20, 19 of 20, and 20 of 20 animals, respectively), which corresponded to granulocyte infiltration into the lamina propria of the ileocecal junction (20 of 20) and gastric ulceration (6 of 20) (data now shown).

Lung. Alveolar macrophages and alveolar septae mononuclear cells containing Ebola VP40 antigen appeared on day 3 through 8 (23 of 24 animals), which corresponded with interstitial pneumonia, starting on day 4 and continuing through terminus (19 of 20; data now shown).

Urogenital Tract. Ebola VP40 antigen-positive mononuclear interstitial cells within the uterus, often surrounding small vessels, were present on day 3, with dispersion throughout the uterine stroma and, rarely, the glandular epithelium by terminus (21 of 24 animals; data now shown). No significant lesions were observed on HE-stained sections of uterus. This cell type was also found within the ovary in close proximity to surrounding small vessels, starting on day 3, and began progressively concentrating within follicular thecal cells by terminus (21 of 24 animals). This corresponded to progressive degeneration and necrosis of thecal cells, starting at day 5 through terminus (20 of 20).

Ebola antigen was also noted in scattered mononuclear interstitial cells within the renal pelvic subepithelial stroma on day 5 and began progressively concentrating on the pelvic transitional epithelium by terminus (19 of 20 animals; data not shown). This corresponded to minimal mixed inflammation infiltrates, starting at day 7 through terminus (8 of 8 animals). Similar inflammatory infiltrates and immunoreactivity was noted in mononuclear interstitial cells of the urinary bladder submucosa and transitional epithelium, starting at day 5 through terminus (19 of 20 animals; data not shown).

Brain. Positive immunoreactivity for Ebola VP40 antigen was noted in the endothelium lining the vessels of the choroid plexus, starting on day 5 through terminus (6 of 20 animals), yet no significant lesions were observed on HE-stained sections (data not shown).

Hematologic Findings. Total and differential white blood cell counts of ZEBOV-infected guinea pigs revealed strong evidence of neutrophilia-mediated leukocytosis. Markedly elevated levels of circulating neutrophils were noted beginning 1 day after infection and remained at high levels through the course of infection. A concurrent marked lymphopenia was observed, as evidenced by declining mean lymphocyte counts. Striking thrombocytopenia, evidenced by reduced circulating platelets, compared with control values, was marked beginning at day 4 and continuing through to terminal collection. Increases in mean platelet volume were also noted beginning on day 4 through terminal time points for both strains. Finally, increases in basophilic and eosinophilic granulocyte counts were observed beginning on day 4, and counts remained elevated through to terminal collection (Table 3).

TABLE 3

Hematologic and Serum Biochemistry Findings

| Day After Infection | Guinea Pig | WBC Count, x10³ cells/mL | Leukocyte Finding | | | | | Platelet Finding | | Clinical Chemistry Finding | | | | | | | |
|---|---|---|---|---|---|---|---|---|---|---|---|---|---|---|---|---|---|
| | | | NE, % | LY, % | MO, % | EO, % | BA % | Count, x10³/mL Platelets/mL | Volume Mean, fL | BUN Level, mg/dL | CRE Level, mg/dL | ALP Level, U/L | ALT Level, U/L | AST Level, U/L | TBIL Level, mg/dL | ALB Level, g/dL | TP Level, g/dL |
| Mock | A-1 | 3.5 | 25.2 | 73.7 | 1.0 | 0.1 | 0.0 | 391.0 | 5.3 | 21.0 | 0.3 | 163.0 | 57.0 | 218.0 | 0.3 | 2.7 | 4.7 |
| Mock | A-2 | 1.6 | 52.4 | 42.4 | 3.8 | 1.4 | 0.0 | 407.0 | 6.0 | 17.0 | 0.3 | 141.0 | 39.0 | 130.0 | 0.3 | 2.8 | 4.9 |
| Mock | A-3 | 1.8 | 35.1 | 63.3 | 1.2 | 0.3 | 0.0 | 425.0 | 6.1 | 16.0 | 0.3 | 217.0 | 42.0 | 95.0 | 0.3 | 2.7 | 4.9 |
| Mock | A-4 | 1.8 | 37.9 | 69.8 | 2.2 | 0.0 | 0.0 | 542.0 | 6.0 | 16.0 | 0.5 | 194.0 | 32.0 | 85.0 | 0.3 | 2.8 | 4.5 |
| 1 | B-1 | 2.2 | 69.9 | 28.6 | 1.3 | 0.2 | 0.0 | 202.0 | 6.9 | 20.0 | 0.2 | 196.0 | 30.0 | 76.0 | 0.3 | 3.0 | 5.1 |
| 1 | B-2 | 2.4 | 57.6 | 39.3 | 2.5 | 0.7 | 0.1 | 291.0 | 5.8 | 20.0 | 0.3 | 292.0 | 38.0 | 119.0 | 0.3 | 2.9 | 4.9 |
| 1 | B-3 | 4.0 | 80.0 | 35.9 | 1.6 | 2.5 | 0.0 | 331.0 | 6.2 | 21.0 | 0.3 | 201.0 | 38.0 | 68.0 | 0.3 | 3.2 | 5.4 |
| 1 | B-4 | 2.8 | 66.2 | 31.5 | 1.9 | 0.4 | 0.1 | 467.0 | 6.5 | 18.0 | 0.3 | 242.0 | 37.0 | 95.0 | 0.3 | 2.9 | 5.2 |
| 2 | C-1 | 1.5 | 65.7 | 31.7 | 0.5 | 1.9 | 0.2 | 219.0 | 5.7 | 16.0 | 0.3 | 206.0 | 33.0 | 85.0 | 0.3 | 2.5 | 4.5 |
| 2 | C-2 | 3.4 | 68.5 | 28.7 | 1.4 | 1.4 | 0.1 | 304.0 | 5.5 | 15.0 | 0.3 | 199.0 | 36.0 | 55.0 | 0.3 | 2.9 | 4.5 |
| 2 | C-3 | 2.5 | 69.7 | 27.7 | 2.0 | 0.6 | 0.0 | 347.0 | 5.4 | 18.0 | 0.3 | 249.0 | 27.0 | 115.0 | 0.2 | 2.7 | 4.9 |
| 2 | C-4 | 2.2 | 72.4 | 24.2 | 1.0 | 2.4 | 0.0 | 451.0 | 5.5 | 17.0 | 0.3 | 221.0 | 30.0 | 78.0 | 0.3 | 3.1 | 5.3 |
| 3 | D-1 | 2.0 | 69.2 | 29.1 | 0.1 | 1.6 | 0.0 | 234.0 | 6.8 | 16.0 | 0.4 | 234.0 | 41.0 | 79.0 | 0.3 | 3.0 | 5.3 |
| 3 | D-2 | 1.4 | 80.0 | 13.6 | 0.7 | 5.5 | 0.2 | 147.0 | 6.6 | 14.0 | 0.4 | 193.0 | 37.0 | 170.0 | 0.3 | 2.4 | 4.8 |
| 3 | D-3 | 4.6 | 82.5 | 14.8 | 1.3 | 1.3 | 0.1 | 399.0 | 6.6 | 17.0 | 0.3 | 132.0 | 39.0 | 105.0 | 0.3 | 2.8 | 5.2 |
| 3 | D-4 | 3.8 | 76.2 | 19.6 | 0.6 | 3.7 | 0.0 | 333.0 | 6.3 | 18.0 | 0.3 | 238.0 | 24.0 | 61.0 | 0.3 | 2.9 | 5.3 |
| 4 | E-1 | 1.1 | 70.1 | 23.0 | 0.3 | 6.4 | 0.0 | 143.0 | 6.3 | 17.0 | 0.4 | 177.0 | 43.0 | 257.0 | 0.3 | 2.3 | 4.4 |
| 4 | E-2 | 1.5 | 54.0 | 22.8 | 2.5 | 18.0 | 2.8 | 118.0 | 6.4 | 17.0 | 0.4 | 248.0 | 50.0 | 358.0 | 0.3 | 1.9 | 4.3 |
| 4 | E-3 | 4.1 | 63.3 | 34.4 | 2.0 | 0.3 | 0.0 | 430.0 | 6.9 | 17.0 | 0.2 | 174.0 | 29.0 | 55.0 | 0.2 | 2.5 | 4.8 |
| 4 | E-4 | 1.2 | 75.5 | 18.9 | 0.0 | 5.0 | 0.7 | 101.0 | 9.7 | 21.0 | 0.4 | 168.0 | 45.0 | 365.0 | 0.3 | 2.1 | 4.5 |
| 5 | F-1 | 0.6 | 58.8 | 26.9 | 0.9 | 11.1 | 3.3 | 27.0 | 6.4 | 22.0 | 0.4 | 76.0 | 36.0 | 244.0 | 0.4 | 1.8 | 3.8 |
| 5 | F-2 | 0.6 | 75.2 | 12.6 | 0.5 | 10.5 | 1.2 | 147.0 | 10.5 | 22.0 | 0.5 | 167.0 | 47.0 | 278.0 | 0.3 | 2.2 | 4.6 |
| 5 | F-3 | 0.7 | 69.0 | 20.0 | 1.7 | 6.0 | 1.3 | 118.0 | 9.8 | 21.0 | 0.2 | 229.0 | 31.0 | 181.0 | 0.2 | 2.0 | 4.4 |
| 5 | F-4 | 2.3 | 74.7 | 16.4 | 1.1 | 6.8 | 1.1 | 137.0 | 10.5 | 19.0 | 0.4 | 243.0 | 88.0 | 189.0 | 0.4 | 1.8 | 4.0 |
| 6 | G-1 | 1.0 | 52.7 | 24.8 | 1.1 | 20.9 | 0.6 | 50.0 | 9.5 | 18.0 | 0.2 | 196.0 | 74.0 | 712.0 | 0.4 | 1.8 | 3.8 |

TABLE 3-continued

Hematologic and Serum Biochemistry Findings

| Day After Infection | Guinea Pig | Leukocyte Finding | | | | | | Platelet Finding | | Clinical Chemistry Finding | | | | | | |
|---|---|---|---|---|---|---|---|---|---|---|---|---|---|---|---|---|
| | | WBC Count, x10³ cells/mL | NE, % | LY, % | MO, % | EO, % | BA % | Count, x10³/ Platelets/mL | Volume Mean, fL | BUN Level, mg/dL | CRE Level, mg/dL | ALP Level, U/L | ALT Level, U/L | AST Level, U/L | TBIL Level, mg/dL | ALB Level, g/dL | TP Level, g/dL |
| 6 | G-2 | 0.6 | 56.6 | 29.2 | 4.4 | 8.8 | 1.1 | 111.0 | 7.8 | 14.0 | 0.2 | 228.0 | 46.0 | 170.0 | 0.6 | 2.2 | 4.8 |
| 6 | G-3 | 0.6 | 69.7 | 22.4 | 1.4 | 5.4 | 0.1 | 64.0 | 9.2 | 22.0 | 0.4 | 134.0 | 32.0 | 208.0 | 0.6 | 1.8 | 3.8 |
| 6 | G-4 | 6.2 | 81.2 | 14.4 | 2.8 | 1.6 | 0.0 | 206.0 | 7.0 | 14.0 | 0.6 | 162.0 | 34.0 | 126.0 | 0.6 | 2.4 | 4.8 |
| 6 | I-4 | 1.3 | 78.7 | 9.3 | 1.9 | 9.0 | 1.1 | 96.0 | 11.7 | 16.0 | 0.4 | 190.0 | 32.0 | 300.0 | 0.6 | 1.8 | 4.0 |
| 7 | H-1 | 1.3 | 65.7 | 13.3 | 1.3 | 17.0 | 2.7 | 38.0 | 9.0 | 28.0 | 0.2 | 378.0 | 64.0 | 588.0 | 0.6 | 1.8 | 4.4 |
| 7 | H-2 | 1.6 | 56.6 | 15.3 | 0.8 | 22.4 | 4.9 | 176.0 | 12.4 | 42.0 | 0.2 | 666.0 | 100.0 | 586.0 | 1.4 | 1.8 | 4.0 |
| 7 | H-3 | 3.2 | 45.9 | 44.1 | 3.3 | 5.4 | 1.3 | 134.0 | 17.9 | 54.0 | 0.2 | 256.0 | 78.0 | 506.0 | 0.4 | 1.8 | 3.8 |
| 7 | H-4 | 1.1 | 69.3 | 14.9 | 0.8 | 11.9 | 3.1 | 43.0 | 9.6 | 24.0 | 0.2 | 158.0 | 54.0 | 388.0 | 0.6 | 1.8 | 3.8 |
| 8 | I-1 | 1.9 | 58.9 | 23.2 | 1.2 | 14.0 | 2.7 | 105.0 | 13.8 | 90.0 | 1.8 | 269.0 | 104.0 | 1212.0 | 0.6 | 1.8 | 3.8 |
| 8 | I-2 | 3.2 | 77.7 | 7.2 | 1.6 | 11.8 | 1.7 | 199.0 | 13.7 | 28.0 | 0.2 | 234.0 | 98.0 | 796.0 | 0.4 | 1.8 | 3.8 |
| 8 | I-3 | 2.8 | 73.1 | 20.6 | 2.3 | 3.3 | 0.7 | 54.0 | 9.7 | 24.0 | 0.6 | 268.0 | 56.0 | 672.0 | 0.4 | 1.8 | 3.8 |

Abbreviations:
ALB, albumin;
ALP, alkaline phosphatase;
ALT, alanine aminotransferase;
AST, aspartate aminotransferase;
BA, basophils;
BUN, blood urea nitrogen;
CRE, creatinine;
EO, eosinophils;
LY, lymphocytes;
MO, monocytes;
NE, neutrophils;
TBIL, total bilirubin;
TP, total protein;
WBC, white blood cell Serum Biochemistry Findings. No remarkable changes were noted in early serum liver-associated enzyme levels; but most all were elevated at late stage of disease (Table 3). Beginning on day 4 and continuing to terminal time points, marked increases (by 2-5-fold) in aspartate aminotransferase levels were observed. No remarkable changes in alkaline phosphatase levels were detected until late in disease in which peak levels of alanine aminotransferase were also recorded. Total bilirubin levels were within normal limits up to day 6, when levels doubled and remained elevated to terminal collection. Blood urea nitrogen levels remained consistent until late in the disease course, when mean increases began at day 7. Levels of serum albumin and total protein, markers of vascular leakage, were markedly decreased beginning on day 4 and remained at these levels through the course of infection.

Figures 1, 4A:
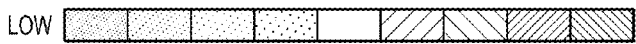
Figure 4B:
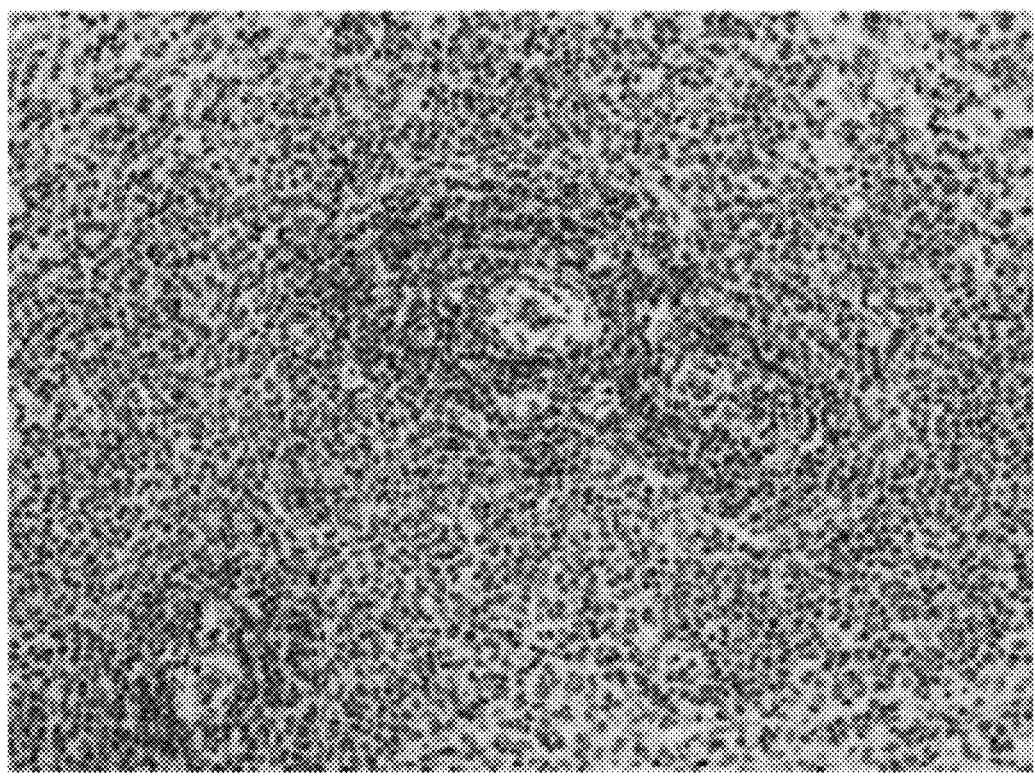
FIG. 4B shows anti-fibrin immunohistochemical staining of control guinea pig spleen (original magnification ×20). No significant immunolabeling was observed.
Figure 4C:
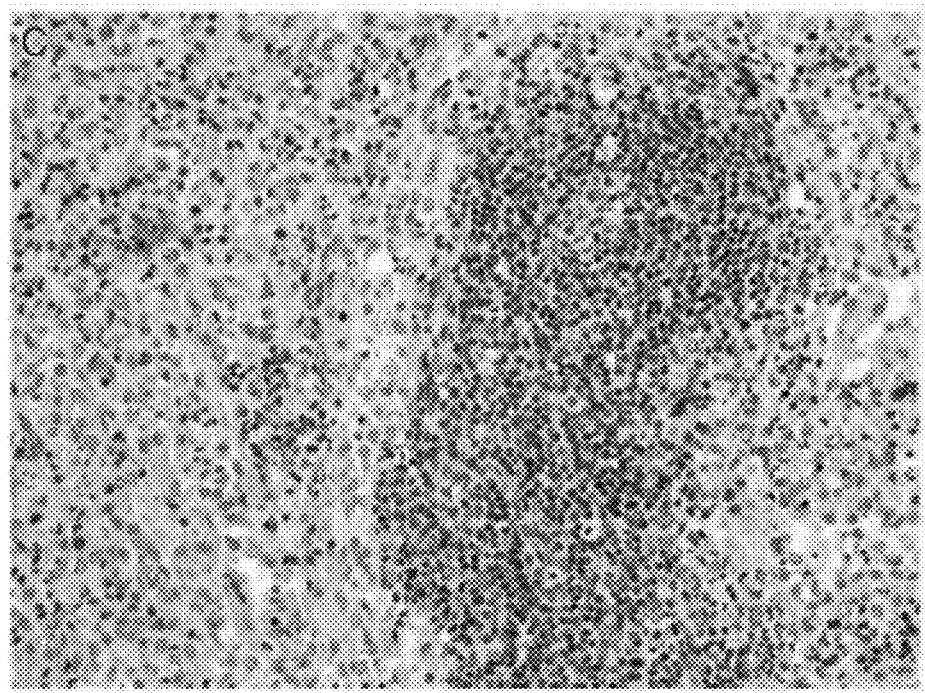

Coagulation Parameters. Prothrombin times (PTs) began to increase beginning on day 3 and continued to increase throughout the course of disease, whereas activated partial thromboplastin times (APTTs) did not increase until late in the disease course, on day 7. Beginning on day 2, gradual decreases in thrombin times (TTs) paralleled increases in fibrinogen content until terminal collection, when a sharp decrease was noted. Circulating protein C activity, as well as tissue factor levels, were decreased; however, plasminogen activator inhibitor-1, von Willebrand factor, and thrombin activatable fibrinolysis inhibitor levels were markedly increased, beginning on days 3, 5, and 6, respectively. Levels of bradykinin gradually increased to concentrations approximately 7-fold higher than those in controls late in disease (FIGS. 4A-1 to 4A-2). No remarkable changes in circulating levels of T-TM, tPA, uPA, TFPI, or prekallikrein were detected.

Circulating Eicosanoid Content, Cytokine Levels, and Nitric Oxide Production.

Circulating eicosanoid content of cysteinyl leukotrienes and thromboxane B2 gradually increased by 2 and 5-fold, respectively, whereas prostacyclin production peaked on day 4, at levels 14 fold higher than those for controls, and then remained elevated until death. Levels of hallmark markers of EHF-associated inflammation (i.e., transforming growth factor β, tumor necrosis factor α, interleukin 6, and nitric oxide) were increased beginning on day 5 of disease [22-25]. The level of HMGB-1, a marker associated with severe sepsis and disseminated intravascular coagulation, was also elevated late in disease (data not shown) [26, 27].

With no licensed filovirus countermeasures currently available, the severity of the current ZEBOV outbreak in West Africa has revealed a dire need to rapidly screen candidate vaccines and therapeutics prior to their use in humans. The development of rodent models that closely reproduce EHF processes (i.e., fever, diarrhea, weight loss, coagulopathies, vascular leak, pathologic lesions, and marked immune derangement similar to sepsis) while conferring predictive value for subsequent testing of these medical countermeasures in NHPs and humans offers an ethical alternative to screening for these materials in primates. An outbred rodent model has several advantages over inbred systems, the most important of which negates the altered immune responsiveness of inbred alternatives, which may provide increased testing stringency by inducing responses to infections more reflective of those in NHP and humans. Unique to the guinea pig is its larger size and circulating blood volume, relative to most other rodent models, which may be better accommodate the increased biological sampling and dosing necessary for optimizing therapeutic and vaccine development, an issue often problematic in smaller rodents.

Here, the inventors demonstrate novel filovirus strains with the hallmark features of EHF in outbred guinea pigs, including fever, weight loss, and infection of mononuclear/dendritiform cells early in the disease course, followed by striking splenic and hepatic pathology, lymphocyte apoptosis, neutrophilia, thrombocytopenia, and marked granulocytosis. Alterations from normal serum biochemistry characteristics also mirrored those in NHP and human disease, specifically with respect to marked increases in liver-associated enzyme levels and marked hypoalbuminemia. Evidence is provided to demonstrate severe coagulopathy in this outbred, small-animal model, including increased PT and APTT, decreased TT, decreased protein C activity, marked fibrinogen deregulation, increased circulating prostacyclin, thromboxane, vWF, and PAI-1 levels, and deposition of fibrin in tissues, all of which parallel that of NHPs and humans [28-34]. The model was also used to explore EHF-associated pathology and provide evidence for abrogation of proinflammatory lipid production, kinin-kallikrein, and fibrinolytic systems, as supported by increased levels of circulating leukotrienes, bradykinin, and TAFI, respectively.

Multiple changes in the genetic sequence were detected, which resulted in subsequent amino acid changes. Only one previously reported mutation was found to be a virulence determinant in VP24 [20]. The changes in the gene encoding glycoprotein are of great interest, as this gene is not only relevant to receptor specificity and immune detection, it is also responsible for producing soluble forms previously identified as possible virulence determinants [35-40]. With the availability of a reverse genetics systems for ZEBOV, these and related questions are now within reach and are targeted for future studies [20, 37, 41, 42].

Despite the few differences from disease severity in humans and NHPs, the outbred Hartley strain guinea pig model presented here represents a robust, accessible, and broadly reflective rodent model of EHF for the study of comparative pathogenesis and development and initial screening of biomedical countermeasures against ZEBOV.

Example 2

Marburg Viruses

Since the discovery of Marburg virus (MARV) during the original outbreak in 1967, it has caused sporadic outbreaks of severe hemorrhagic fever in Central Africa, with case-fatality rates (CFRs) ranging from 23% to 90% [1-3]. Research has focused on a handful of strains obtained from these outbreaks, with an emphasis on the Musoke, Ravn (MARV-Rav), and Angola (MARVAng) strains. The Musoke strain was first isolated in 1980 from a physician who survived nosocomial transmission from a patient infected in Nzoia, Kenya [4]. MARV-Rav was first isolated in 1987 from a case originating in southeastern Kenya but has been associated with large outbreaks of Marburg hemorrhagic fever (MHF) in the Democratic Republic of the Congo during 1998-2000, where strain-specific CFR metrics were impossible to enumerate because of concurrent circulation of multiple strains [1, 3]. MARV-Ang was responsible for the largest documented outbreak (252 cases) of MHF, in which a 90% CFR was reported, a rate very similar to that of the most virulent strains of Ebola virus [2].

Phylogenetic comparisons across MARV strains reveal 2 distinct genetic lineages: Ravn and the Lake Victoria Marburg complex (e.g., Musoke, Ci67, Popp, and Angola strains), wherein nucleotide variances of >20% between Ravn and other MARV genomes exist [2]. The level of genetic divergence and variation in CFR between strains suggest that these changes may contribute to variation in virulence. Many studies to characterize the pathogenesis of MARV infection have occurred since the original outbreak; however, some variability exists between these reports, depending on which strain of MARV was used [5-8]. This presents challenges for medical countermeasure development, such that inherent genetic differences may contribute to altered disease outcome across MARV strains, and thus any countermeasure or diagnostic assay may need evaluation across MARV strains.

Until recently, most MARV-specific countermeasures were tested in vivo, using mice or inbred strain 13 guinea pigs (GPs) [9-11]. Limitations in interpretation are necessary because delayed immunoresponsiveness and incomplete recapitulation of hallmark features of MHF (fever, diarrhea, weight loss, coagulopathies, vascular leak, and marked immune derangement similar to sepsis) may factor into the limited predictive value that these models have had to date [12]. The present inventors have developed uniformly lethal outbred GP models for several strains of MARV by serial adaptation. These GP-adapted (GPA) MARV strains have demonstrated predictive efficacy in postexposure treatment in nonhuman primates (NHPs) [5, 13]. Here, a temporal comparison of the events leading to death in outbred GPs infected with GPA MARV-Ang and MARV-Rav was performed. Using the invention several remarkable similarities were found between MHF in NHPs and MHF in humans but also MARV strain-specific differences in virulence.

Virus Adaptation. MARV-Ang and MARV-Rav strains were adapted to uniform lethality in outbred Hartley strain GPs by serial passage of virus isolated from infected livers and/or spleens and sequenced as outlined herein.

Marburg virus strain Angola guinea pig adapted virus methods and results and hamster studies Step 1. Starting material: Serum from a patient from the 2005 outbreak of MARV-Angola in Angola. Methods and results: A group outbred Hartley guinea pigs were inoculated by intraperitoneal (i.p.) injection with a dilution of serum from a patient from the 2005 outbreak of MARV-Angola in Angola. Approximately one week after inoculation guinea pigs were euthanized and their livers and spleens were harvested and homogenized in EMEM plus 10% FBS at a 10% weight to volume ratio. This clarified 10% outbred guinea pig pooled liver and spleen homogenate is referred to as guinea pig p1 liver and spleen homogenate (Outbred guinea pig liver/spleen p1).

Step 2. Starting material: Clarified 10% outbred guinea pig pooled liver and spleen homogenate from Step 1 (Outbred guinea pig liver/spleen p1). Methods and results: A group outbred Hartley guinea pigs were inoculated by i.p. injection with a dilution of the clarified 10% outbred guinea pig pooled liver and spleen homogenate from Step 1. Approximately one week after inoculation guinea pigs were euthanized and their livers and spleens were harvested and homogenized in EMEM plus 10% FBS at a 10% weight to volume ratio. This clarified 10% outbred guinea pig pooled liver and spleen homogenate is referred to as guinea pig p2 liver and spleen homogenate (Outbred guinea pig liver/spleen p2).

Step 3. Starting material: Clarified 10% outbred guinea pig pooled liver and spleen homogenate from step 1 (Outbred guinea pig liver/spleen p2). Methods and results: The outbred guinea pig pooled liver and spleen homogenate from Step 2 was diluted 1:10 in EMEM and inoculated on flasks of Vero E6 cells (ATCC CRL-1586) maintained in EMEM plus 10% FBS supplemented with glutamine and gentamicin. Culture fluid was collected from these flasks approximately one week later. This culture fluid is referred to as outbred guinea pig liver/spleen p2, Vero E6 p1 seed stock.

Step 4. Starting material: Outbred guinea pig liver/spleen p2, Vero E6 p1 seed stock from Step 3. Methods and results: A group of 6 outbred Hartley guinea pigs were inoculated by i.p. injection with a dilution of the outbred guinea pig liver/spleen p2, Vero E6 p1 seed stock from Step 3. Approximately one week after inoculation 2 of the 6 guinea pigs were euthanized and their livers and spleens were harvested and homogenized in EMEM plus 10% FBS at a 10% weight to volume ratio. The clarified liver and spleen homogenates then served as the inoculum for additional outbred Hartley guinea pigs in Step 5 below as uniform lethality was not achieved in the remaining 4 animals. This clarified 10% outbred Hartley guinea pig pooled liver and spleen homogenate is referred to as an outbred guinea pig p2, p1 liver and spleen homogenate (Outbred guinea pig liver/spleen p2, Vero E6p1, Outbred guinea pig liver/spleen p1).

Step 5. Starting material: Clarified 10% outbred Hartley guinea pig pooled p2, p1 liver and spleen homogenate from Step 4 (Outbred guinea pig liver/spleen p2, Vero E6p1, Outbred guinea pig liver/spleen p1). Methods and results: A group of 6 outbred Hartley guinea pigs were inoculated by i.p. injection with a dilution of the outbred guinea pig liver/spleen p2, Vero E6 p1, outbred guinea pig clarified liver/spleen homogenate from Step 4. Approximately one week after inoculation 2 of the 6 guinea pigs were euthanized and the liver and spleen from one of these animals was harvested and homogenized in EMEM plus 10% FBS at a 10% weight to volume ratio. This clarified 10% outbred guinea pig pooled spleen homogenate is referred to as an outbred guinea pig p2, p2 liver and spleen homogenate (Outbred guinea pig liver/spleen p2, Vero E6p1, Outbred guinea pig liver/spleen p2).

Step 6. Starting material: Clarified 10% outbred guinea pig pooled liver and spleen homogenate is referred to as an outbred guinea pig p2, p2 liver and spleen homogenate from Step 5 (Outbred guinea pig liver/spleen p2, Vero E6p1, Outbred guinea pig liver/spleen p2). Methods and results: The clarified 10% outbred guinea pig p2, p2 liver and spleen homogenate (Outbred guinea pig liver/spleen p2, Vero E6p1, Outbred guinea pig liver/spleen p2) from Step 5 was diluted 1:10 in EMEM and inoculated on flasks of Vero 76 cells (ATCC CRL-1587) maintained in EMEM plus 10% FBS supplemented with glutamine and gentamicin. Culture fluid was collected from these flasks approximately 7 days later and titrated following conventional methods. This culture fluid is referred to as an Outbred guinea pig liver/spleen p2, Vero E6p1, Outbred guinea pig liver/spleen p2, Vero p1 seed stock. The titer of this seed stock is approximately 2.12× 10^7 pfu·ml.

Step 7. Starting material: Outbred guinea pig liver/spleen p2, Vero E6p1, Outbred guinea pig liver/spleen p2, Vero p1 seed stock from Step 6. Methods and results: Virulence of the seed stock from Step 6 was confirmed in a group of several different studies as follows: 1) a total of 4 outbred Hartley guinea pigs were inoculated by i.p. injection with a target does of approximately 5,000 pfu of the Outbred guinea pig liver/spleen p2, Vero E6p1, Outbred guinea pig liver/spleen p2, Vero p1 seed stock from Step 6 in a volume of approximately 0.5 ml; 2) a total of 5 outbred Hartley guinea pigs were inoculated by i.p. injection with a target does of approximately 5,000 pfu of the Outbred guinea pig liver/spleen p2, Vero E6p1, Outbred guinea pig liver/spleen p2, Vero p1 seed stock from Step 6 in a volume of approximately 0.5 ml. All 9 animals succumbed between days 8 and 13 after exposure to this seed stock confirming the uniform lethality in outbred Hartley guinea pigs caused by this seed stock.

Step 8. Starting material: Outbred guinea pig liver/spleen p2, Vero E6p1, Outbred guinea pig liver/spleen p2, Vero p1 from Step 6. Methods and results: Approximately 1 ml of the Outbred guinea pig liver/spleen p2, Vero E6p1, Outbred guinea pig liver/spleen p2, Vero p1 from Step 6 was removed from the seed vial and placed in ~5 ml of Trizol LS and vortexed 3 times and allowed to sit for 10 minutes. The 6 ml were then placed into 2 separate 3 ml Nunc cryo-vials for removal from the BSL-4. RNA was isolated from the Trizol LS/sample mixture using Zymo Research Direct-zol RNA mini-prep per manufacturer's instructions. Approximately 150 ng of purified RNA were used to make cDNA using the NuGen Ovation RNA-seq 2.0 kit ultimately for the preparation of the double stranded DNA library using Encore Ion Torrent library prep kit. Sequencing was performed by the UTMB Molecular Core on the Ion Torrent using 318-v2 deep sequencing chips. Sequence analysis was performed using DNA Star Seqman NGen software based on paired-end analysis of 100 bp overlaps. Sequencing results were compared to GenBank sequences for the starting material and are shown below.

UTMB Geisbert MARV-Angola Guinea Pig Adapted Strain (compared to Accession No. DQ447653)

| Nucleotide | Base Change | Result | Gene |
| --- | --- | --- | --- |
| 2931 | U > A | | Non-coding |
| 4735 | U > A | N56K | VP40 |
| 10402 | G > A | V66I | VP24 |
| 10853 | U > C | L216S | VP24 |
| 13115 | U > C | Silent | L |
| 17249 | U > A | Silent | L |
| 18713 | C > A | | Non-coding |
| 19105 | A > U | | Non-coding |

Step 9. Starting material: Outbred guinea pig liver/spleen p2, Vero E6p1, Outbred guinea pig liver/spleen p2, Vero p1 seed stock from Step 6. Methods and results: Virulence of the seed stock from Step 6 was assessed in Syrian golden hamsters. A total of 6 Syrian golden hamsters were inoculated by i.p. injection with a target does of approximately 5,000 pfu of the Outbred guinea pig liver/spleen p2, Vero E6p1, Outbred guinea pig liver/spleen p2, Vero p1 seed stock from Step 6 in a volume of approximately 0.5 ml. All 6 animals succumbed on day 8 after exposure to this seed stock confirming the uniform lethality in Golden Syrian hamsters caused by this seed stock. All 6 animals developed prominent macular rashes consistent with rashes reported in primates. This is the first rodent species of any kind to develop rashes in response to Marburg virus infection.

Marburg Virus Strain Ci67 Guinea Pig Adapted Virus Methods and Results

Step 1. Starting material: Serum from a patient from the original 1967 outbreak of Marburg virus in Germany that had been passed twice in Vero E6 cells. Methods and results: A group inbred Strain 13 guinea pigs were inoculated by intramuscular (i.m.) injection with a dilution of Vero p2 culture fluid derived from patient serum. Approximately one week after inoculation guinea pigs were euthanized and their spleens were harvested and homogenized in EMEM plus 10% FBS at a 10% weight to volume ratio. This clarified 10% guinea pig pooled spleen homogenate is referred to as an inbred Strain 13 guinea pig p1 spleen homogenate (Inbred Strain 13 guinea spleen p1).

Step 2. Starting material: Clarified 10% inbred Strain 13 guinea pig pooled spleen homogenate from Step 1 (Inbred Strain 13 guinea pig spleen p1). Methods and results: A group of inbred Strain 13 guinea pigs were inoculated by i.m. injection with a dilution of the clarified 10% guinea pig pooled spleen homogenate from Step 1. Approximately one week after inoculation guinea pigs were euthanized and their spleens were harvested and homogenized in EMEM plus 10% FBS at a 10% weight to volume ratio. This clarified guinea pig pooled spleen homogenate is referred to as an inbred Strain guinea pig p2 spleen homogenate (Inbred Strain 13 guinea pig spleen p2).

Step 3. Starting material: Clarified 10% inbred Strain13 guinea pig pooled spleen homogenate from Step 2 (Inbred Strain 13 guinea pig spleen p2). Methods and results: A group of outbred Hartley guinea pigs were inoculated by intraperitoneal (i.p.) injection with a dilution of the clarified 10% guinea pig pooled p2 spleen homogenate from Step 2. Approximately one week after inoculation guinea pigs were euthanized and their livers and spleens were harvested and homogenized in EMEM plus 10% FBS at a 10% weight to volume ratio. This clarified outbred Hartley guinea pig pooled liver and spleen homogenate is referred to as guinea pig p3 liver and spleen homogenate (Inbred guinea pig spleen p2, outbred guinea pig liver/spleen p1).

Step 4. Starting material: Clarified 10% outbred Hartley guinea pig pooled spleen homogenate from Step 3 (Inbred guinea pig spleen p2, outbred guinea pig liver/spleen p1). Methods and results: A group of outbred Hartley guinea pigs were inoculated by i.p. injection with a dilution of the clarified 10% guinea pig pooled p3 liver and spleen homogenate from Step 3. Approximately one week after inoculation guinea pigs were euthanized and their livers and spleens were harvested and homogenized in EMEM plus 10% FBS at a 10% weight to volume ratio. This clarified outbred Hartley guinea pig pooled liver and spleen homogenate is referred to as guinea pig p4 liver and spleen homogenate (Inbred Strain 13 guinea pig spleen p2, outbred guinea pig liver/spleen p2).

Step 5. Starting material: Clarified 10% outbred guinea pig pooled liver and spleen homogenate is referred to as a guinea pig p4 liver and spleen homogenate from Step 4 (Inbred guinea pig spleen p2, outbred guinea pig liver/spleen p2). Methods and results: The clarified 10% guinea pig liver and spleen p4 homogenate (Inbred guinea pig spleen p2, outbred guinea pig liver/spleen p2) from Step 4 was diluted 1:10 in EMEM and inoculated on flasks of Vero 76 cells (ATCC CRL-1587) maintained in EMEM plus 10% FBS supplemented with glutamine and gentamicin. Culture fluid was collected from these flasks approximately 8 days later and titrated following conventional methods. This culture fluid is referred to as a Vero E6 p2, inbred Strain 13 guinea pig spleen p2, outbred guinea pig liver/spleen p2, Vero p1 seed stock. The titer of this seed stock is approximately $1.02 \times 10^{7}$ pfu·ml.

Step 6. Starting material: Vero E6 p2, inbred Strain 13 guinea pig spleen p2, outbred guinea pig liver/spleen p2, Vero p1 seed stock from Step 5 (Vero E6 p2, inbred Strain 13 guinea pig spleen p2, outbred guinea pig liver/spleen p2, Vero p1 seed stock). Methods and results: Virulence of the seed stock from Step 5 was confirmed in as follows: a total of 5 outbred Hartley guinea pigs were inoculated by i.p. injection with a target does of approximately 5,000 pfu of the Vero E6 p2, inbred Strain 13 guinea pig spleen p2, outbred guinea pig liver/spleen p2, Vero p1 seed stock from Step 5 in a volume of approximately 0.5 ml. All 5 animals succumbed between days 8 and 11 after exposure to this seed stock confirming the uniform lethality in outbred Hartley guinea pigs caused by this seed stock.

Step 7. Starting material: Vero E6 p2, inbred Strain 13 guinea pig spleen p2, outbred guinea pig liver/spleen p2, Vero p1 seed stock from Step 5 (Vero E6 p2, inbred Strain 13 guinea pig spleen p2, outbred guinea pig liver/spleen p2, Vero p1 seed stock). Methods and results: Approximately 1 ml of the Vero E6 p2, inbred Strain 13 guinea pig spleen p2, outbred guinea pig liver/spleen p2, Vero p1 seed stock from Step 5 was removed from the seed vial and placed in ~5 ml of Trizol LS and vortexed 3 times and allowed to sit for 10 minutes. The 6 ml were then placed into 2 separate 3 ml Nunc cryo-vials for removal from the BSL-4. RNA was isolated from the Trizol LS/sample mixture using Zymo Research Direct-zol RNA mini-prep per manufacturer's instructions. Approximately 150 ng of purified RNA were used to make cDNA using the NuGen Ovation RNA-seq 2.0 kit ultimately for the preparation of the double stranded DNA library using Encore Ion Torrent library prep kit. Sequencing was performed by the UTMB Molecular Core on the Ion Torrent using 318-v2 deep sequencing chips. Sequence analysis was performed using DNA Star Seqman NGen software based on paired-end analysis of 100 bp overlaps. Sequencing results were compared to GenBank sequences for the starting material and are shown below.

UTMB Geisbert MARV-Ci67 Guinea Pig Adapted Strain (compared to Accession No. EF446132.1)

| Nucleotide | Base Change | Result | Gene |
| --- | --- | --- | --- |
| 8811 | ->U | | Non-coding |
| 10629 | G > A | G141E | VP24 |
| 10631 | A > U | I142S | VP24 |
| 10632 | U > C | I142S | VP24 |
| 10633 | C > U | I142S | VP24 |
| 10634 | U > A | Y143I | VP24 |
| 10635 | A > U | Y143I | VP24 |

Marburg Virus Strain Ravn Guinea Pig Adapted Virus Methods and Results

Step 1. Starting material: Serum from a patient from the 1987 outbreak of MARV-Ravn in Kenya that had been passed once in Vero 76 cells and once in rhesus monkeys. Methods and results: A group inbred Strain 13 guinea pigs were inoculated by i.m. injection with a dilution of serum from a Marburg-Ravn virus rhesus monkey. Approximately one week after inoculation guinea pigs were euthanized and their spleens were harvested and homogenized in EMEM plus 10% FBS at a 10% weight to volume ratio. This clarified 10% guinea pig pooled spleen homogenate is referred to as guinea pig p1 spleen homogenate (Inbred Strain 13 guinea spleen p1).

Step 2. Starting material: Clarified 10% inbred Strain 13 guinea pig pooled spleen homogenate from Step 1 (Inbred Strain 14 guinea pig spleen p1). Methods and results: A group of inbred Strain 13 guinea pigs were inoculated by i.m. injection with a dilution of the clarified 10% guinea pig pooled spleen homogenate from Step 1. Approximately one week after inoculation guinea pigs were euthanized and their spleens were harvested and homogenized in EMEM plus 10% FBS at a 10% weight to volume ratio. This clarified guinea pig pooled spleen homogenate is referred to as guinea pig p2 spleen homogenate (Inbred Strain 13 guinea pig spleen p2).

Step 3. Starting material: Clarified 10% inbred Strain13 guinea pig pooled spleen homogenate from Step 2 (Inbred guinea pig spleen p2). Methods and results: A group of outbred Hartley guinea pigs were inoculated by i.p. injection with a dilution of the clarified 10% guinea pig pooled p2 spleen homogenate from Step 2 (Inbred guinea pig spleen p2). Approximately one week after inoculation guinea pigs were euthanized and their livers and spleens were harvested and homogenized in EMEM plus 10% FBS at a 10% weight to volume ratio. This clarified guinea pig pooled liver and spleen homogenate is referred to as guinea pig p3 liver and spleen homogenate (Inbred guinea pig spleen p2, outbred guinea pig liver/spleen p1).

Step 4. Starting material: Clarified 10% outbred guinea pig pooled spleen homogenate from Step 3 (Inbred guinea pig spleen p2, outbred guinea pig liver/spleen p1). Methods and results: The clarified 10% guinea pig liver and spleen p3 homogenate (Inbred guinea pig spleen p2, outbred guinea pig liver/spleen p1) from Step 3 was diluted 1:10 in EMEM and inoculated on flasks of Vero 76 cells (ATCC CRL-1587) maintained in EMEM plus 10% FBS supplemented with glutamine and gentamicin. Culture fluid was collected from these flasks approximately 8 days later and titrated following conventional methods. This culture fluid is referred to as a Vero p1, Monkey p1, inbred Strain 13 guinea pig spleen p2, outbred guinea pig liver/spleen p1, Vero p1 seed stock. The titer of this seed stock is approximately 3.67×10^7 pfu·ml.

Step 5. Starting material: Vero p1, Monkey p1, inbred Strain 13 guinea pig spleen p2, outbred guinea pig liver/spleen p1, Vero p1 seed stock from Step 4. Methods and results: Virulence of the seed stock from Step 4 was confirmed in a group of several different studies as follows: 1) a total of 5 outbred Hartley guinea pigs were inoculated by i.p. injection with a target does of approximately 5,000 pfu of the Vero p1, Monkey p1, inbred Strain 13 guinea pig spleen p2, outbred guinea pig liver/spleen p1, Vero p1 seed stock from Step 4 in a volume of approximately 0.5 ml; 2) a total of 5 outbred Hartley guinea pigs were inoculated by i.p. injection with a target does of approximately 5,000 pfu of the Vero p1, Monkey p1, inbred Strain 13 guinea pig spleen p2, outbred guinea pig liver/spleen p1, Vero p1 seed stock from Step 4 in a volume of approximately 0.5 ml. All 9 animals succumbed between days 8 and 11 after exposure to this seed stock confirming the uniform lethality in outbred Hartley guinea pigs caused by this seed stock.

Step 6. Starting material: Vero p1, Monkey p1, inbred Strain 13 guinea pig spleen p2, outbred guinea pig liver/spleen p1, Vero p1 seed stock from Step 4. Methods and results: Approximately 1 ml of the Vero p1, Monkey p1, inbred Strain 13 guinea pig spleen p2, outbred guinea pig liver/spleen p1, Vero p1 seed stock from Step 4 was removed from the seed vial and placed in ~5 ml of Trizol LS and vortexed 3 times and allowed to sit for 10 minutes. The 6 ml were then placed into 2 separate 3 ml Nunc cryo-vials for removal from the BSL-4. RNA was isolated from the Trizol LS/sample mixture using Zymo Research Direct-zol RNA mini-prep per manufacturer's instructions. Approximately 150 ng of purified RNA were used to make cDNA using the NuGen Ovation RNA-seq 2.0 kit ultimately for the preparation of the double stranded DNA library using Encore Ion Torrent library prep kit. Sequencing was performed by the UTMB Molecular Core on the Ion Torrent using 318-v2 deep sequencing chips. Sequence analysis was performed using DNA Star Seqman NGen software based on paired-end analysis of 100 bp overlaps. Sequencing results were compared to GenBank sequences for the starting material and are shown below.

UTMB Geisbert MARV-Ravn Guinea Pig Adapted Strain (compared to Accession No. DQ447649.1)

| Nucleotide | Base Change | Result | Gene |
|---|---|---|---|
| 143 | A > U | T14S | NP |
| 4647 | U > C | L27S | VP40 |
| 4665 | U > C | L33P | VP40 |
| 4725 | U > C | F53S | VP40 |
| 4726 | U > C | F53S | VP40 |
| 7118 | G > C | G435A | GP |
| 13787 | U > C | Silent | L |

Inoculation of GPs. Animal studies were conducted under biosafety level 4 (BSL4) containment at the Galveston National Laboratory and were approved by the University of Texas Medical Branch (UTMB) Institutional Laboratory Animal Care and Use Committee. Female outbred Hartley strain GPs (weight, approximately 351-400 g) from Charles River Laboratories were quarantined upon receipt and acclimatized for approximately 1 week prior to MARV challenge. Forty animals were divided into 11 groups of 4 animals per group, with 5 groups per virus strain and 1 uninfected control group. Individual animals were challenged with approximately 5000 plaque-forming units (PFU) of GPA MARV-Ang or GPA MARV-Rav or mock challenged with Hanks' balanced salt solution with 2% fetal bovine serum, by intraperitoneal injection.

Necropsy. Each group of MARV-infected GPs was euthanized on postinfection days 1, 3, 5, or 7 or at a terminal point, when euthanasia criteria was met (n=4/group/day). Clinical signs, weights, and transponder-mediated temperatures were recorded daily up to the time of euthanasia. Prior to necropsy, whole-blood, plasma (in ethylenediaminetetraacetic acid-lined tubes), and citrated plasma specimens were collected by cardiac puncture for hematologic analysis, serum/plasma biochemical assays, and viremia determination. Gross findings were documented, and select tissue specimens were aseptically removed and frozen at −70° C. until analysis. The following tissue specimens were collected from all animals for histologic and immunohistochemistry analyses: liver, spleen, kidney, adrenal gland, lung, brain, lymph nodes (axillary, inguinal, mesenteric, and mandibular), salivary gland, trachea, esophagus, stomach, duodenum, ileocecal junction, colon, urinary bladder, reproductive tract, pancreas, haired skin, and heart.

Histologic and Immunohistochemistry Analyses. Selected tissues were fixed in formalin for at least 21 days in a BSL-4 facility. Specimens were then removed from the BSL-4 facility and processed in a BSL-2 facility, using routine histopathologic procedures.

Hematologic Analysis, Serum Biochemistry Analysis, and Determination of Coagulation Parameters. Complete blood counts, analysis of coagulation dynamics, and analysis of blood chemistry parameters were performed on blood, serum, or plasma specimens. Analysis of select cytokines, coagulation factors, eicanosoids, and nitric oxide in serum or plasma specimens was also performed.

Virus Isolation. Determination of infectious virus in plasma, spleen, liver, kidney, adrenal, pancreas, lung, and brain tissue homogenates was made using standard plaque assays.

Statistics Statement. Conducting animal studies in a BSL-4 facility severely restricts the number of animal subjects, the volume of biological samples that can be obtained, and the ability to repeat assays independently, thus limiting the power of statistical analysis. Consequently, data are presented as the mean values calculated from replicate samples, not replicate assays, and error bars represent standard deviations across replicates.

Adapted Virus Sequence Analysis. Sequence comparison of GPA MARV-Ang with the prototype strain (accession number DQ447653.1) revealed nucleotide substitutions resulting in a single amino acid change in VP40 and 2 changes in VP24, both viral matrix proteins. Three nucleotide changes were discovered in noncoding regions, and 2 silent mutations were detected in the polymerase gene. Comparison of GPA MARV-Rav with prototype MARV-Rav (accession number DQ447649.1) revealed nucleotide substitutions resulting in a single amino acid change in both NP and glycoprotein and 4 changes in VP40. One silent mutation in the polymerase gene was also detected. The resulting mutations may have been acquired during the consecutive passages in GPs and/or passages in Vero 76 cells during seed stock production (Table 4).

TABLE 4

Genetic Changes in Guinea Pig-Adapted (GPA) Marburg Virus (MARV) Strains

| Strain, Nucleotide | Base Change | Result | Gene |
|---|---|---|---|
| MARV-Angola | | | |
| 2931 | U > A | . . . | Noncoding |
| 4735 | U > A | N56K | VP40 |
| 10402 | G > A | V66I | VP24 |
| 10853 | U > C | L216S | VP24 |
| 13115 | U > C | Silent | L |
| 17249 | U > A | Silent | L |
| 18713 | C > A | . . . | Noncoding |
| 19105 | A > U | . . . | Noncoding |
| MARV-Ravn | | | |
| 143 | A > U | T14S | NP |
| 4647 | U > C | L27S | VP40 |
| 4665 | U > C | L33P | VP40 |
| 4725 | U > C | F53S | VP40 |
| 4726 | U > C | F53S | VP40 |
| 7118 | G > C | G435A | Glycoprotein |
| 13787 | U > C | Silent | L |

The genome of GPA MARV-Ravn was compared with that of variant DQ447649.1, and the genome of MARV-Angola was compared with that of variant DQ447653.

Virus Titers in Blood and Tissues. Plasma viremia was first detected on day 3 for both MARV-Ang and MARV-Rav strains, with equivalent titers of approximately 2.7 log 10 PFU/mL. The peak MARV-Ang viremia level of approximately 7.9 log 10 PFU/mL on day 7 was maintained through terminal collections. The MARV-Rav viremia level peaked at approximately 6.4 log 10 PFU/mL at terminal collection. Virus was recovered from spleen, pancreas, lung, kidney, liver, adrenal gland, and plasma from both MARV-Ang and MARV-Rav groups beginning on day 3, with higher titers detected in spleen, lung, and liver homogenates from the MARV-Ang group. On day 7, higher mean titers were recorded in liver and plasma from Marv-Ang-infected animals, whereas higher mean titers were observed in spleen, lung, kidney, and adrenal glands from MARV-Rav-infected animals. The highest titers in lung, kidney, adrenal gland, and plasma were measured at terminal collection in MARV-Ang-infected animals (Table 5).

TABLE 5

Tissue and Plasma Marburg Virus (MARV) Burdens Over Time, by MARV Strain
MARV Load, Log10 PFU/mL, Mean ± SD

| Tissue, Strain | Day 1 | Day 3 | Day 5 | Day 7 | Terminal Time Point |
|---|---|---|---|---|---|
| Brain | | | | | |
| Ravn | ND | ND | 3.62 ± 0.46 | 4.71 ± 0.49 | 5.74 ± 0.49 |
| Angola | ND | ND | 3.37 ± 0.38 | 5.89 ± 0.42 | 5.01 ± 0.42 |
| Spleen | | | | | |
| Ravn | ND | 4.68 ± 0.44 | 6.35 ± 0.94 | 7.90 ± 0.60 | 7.19 ± 0.39 |
| Angola | ND | 5.27 ± 0.27 | 6.75 ± 0.38 | 6.95 ± 0.47 | 7.77 ± 0.51 |
| Pancreas | | | | | |
| Ravn | ND | 3.18 ± 0.62 | 5.03 ± 0.07 | 6.52 ± 0.64 | 6.14 ± 0.31 |
| Angola | ND | 2.65 ± 0.42 | 5.19 ± 0.49 | 6.34 ± 0.63 | 6.40 ± 0.36 |
| Lung | | | | | |
| Ravn | ND | 3.03 ± 0.33 | 5.32 ± 0.51 | 7.06 ± 0.46 | 6.08 ± 0.36 |
| Angola | ND | 4.00 ± 0.46 | 4.82 ± 0.28 | 6.25 ± 0.36 | 6.90 ± 0.43 |
| Kidney | | | | | |
| Ravn | ND | 2.75 ± 0.62 | 4.87 ± 0.51 | 6.80 ± 0.59 | 5.53 ± 0.41 |
| Angola | ND | 3.29 ± 0.37 | 4.72 ± 0.16 | 5.92 ± 0.51 | 7.71 ± 0.60 |
| Liver | | | | | |
| Ravn | ND | 4.21 ± 0.57 | 6.81 ± 0.36 | 7.84 ± 0.41 | 7.89 ± 0.50 |
| Angola | ND | 5.69 ± 0.45 | 5.79 ± 0.29 | 8.48 ± 1.08 | 8.01 ± 0.34 |
| Adrenal | | | | | |
| Ravn | ND | 3.30 ± 0.62 | 6.59 ± 0.61 | 7.88 ± 0.69 | 6.78 ± 0.63 |
| Angola | ND | 3.49 ± 0.39 | 5.51 ± 0.36 | 6.98 ± 0.50 | 7.64 ± 0.54 |
| Plasma | | | | | |
| Ravn | ND | 2.60 ± 0.48 | 5.96 ± 1.23 | 6.17 ± 0.43 | 6.36 ± 1.15 |
| Angola | ND | 2.88 ± 0.44 | 5.77 ± 0.52 | 7.97 ± 0.42 | 7.60 ± 0.40 |

Abbreviations:
ND, not detected;
PFU, plaque-forming units.

Figure 5A:
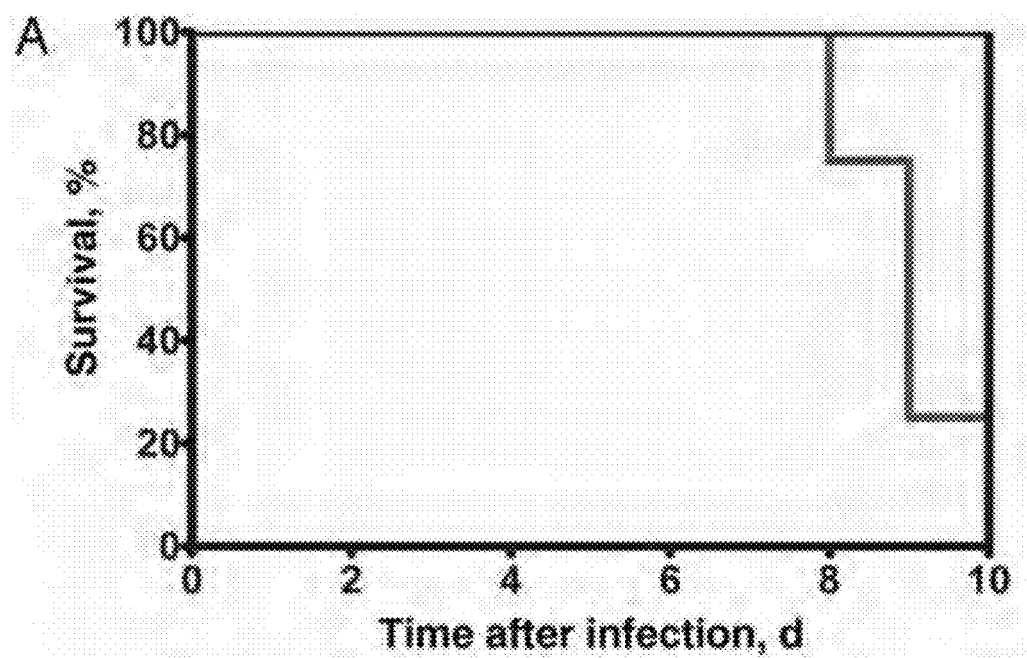
FIGS. 5A to 5F show.
Figure 5B:
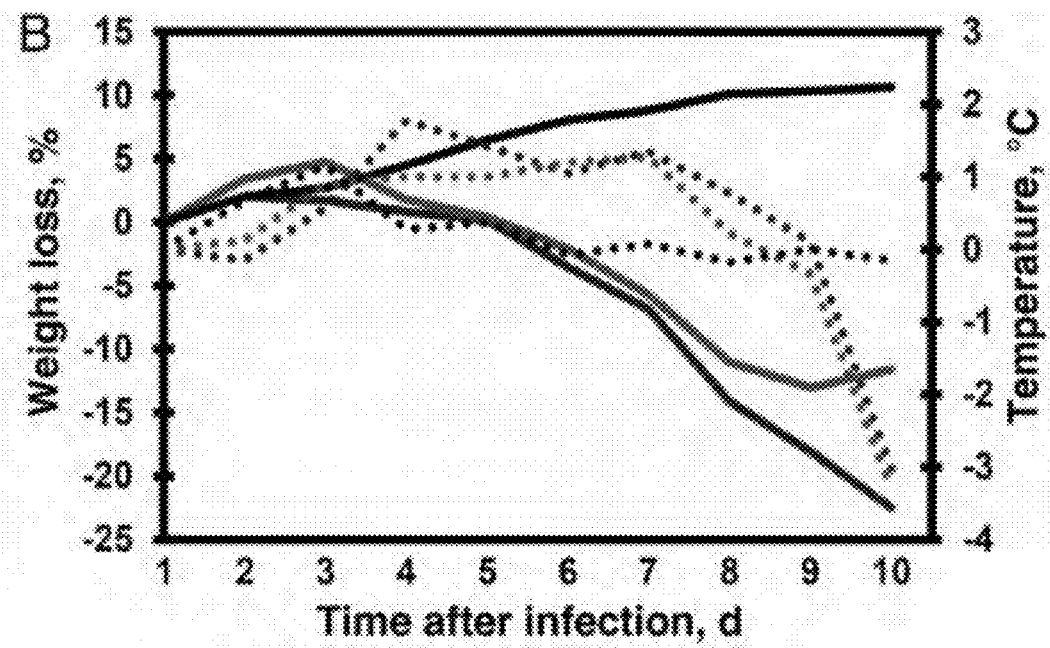

GPs from terminal groups were followed for mean changes in weights, temperature, and time to death. MARV-Ang-infected animals from this group met euthanasia criteria a mean of 1 day earlier than subjects from the MARV-Rav group (FIG. 5A). Mean body weights at the time of necropsy were compared with initial weights, with comparable progressive weight loss between virus strain cohorts noted. Mean percentages changes in weights for MARV-Rav-infected GPs were −1.8% on day 5, −8.4% on day 7, and −25% at the terminal time point. MARV-Ang-infected animals began losing weight on day 6 (mean percentage change, −1.3%), with mean percentages changes of −6% on day 7 and −12.5% at terminal time points. MARV-Rav-infected animals had higher mean temperatures beginning on day 3 and remained at +1° C. until day 7, when a peak of +1.5° C. was followed by progressive hypothermia until time of death. MARV-Ang-infected animals had slowly progressive fevers that peaked at +1° C. on day 6 and were also followed by hypothermia. Mock-infected control animals maintained stable weight and core temperature during the study (FIG. 5B).

Figure 5C:
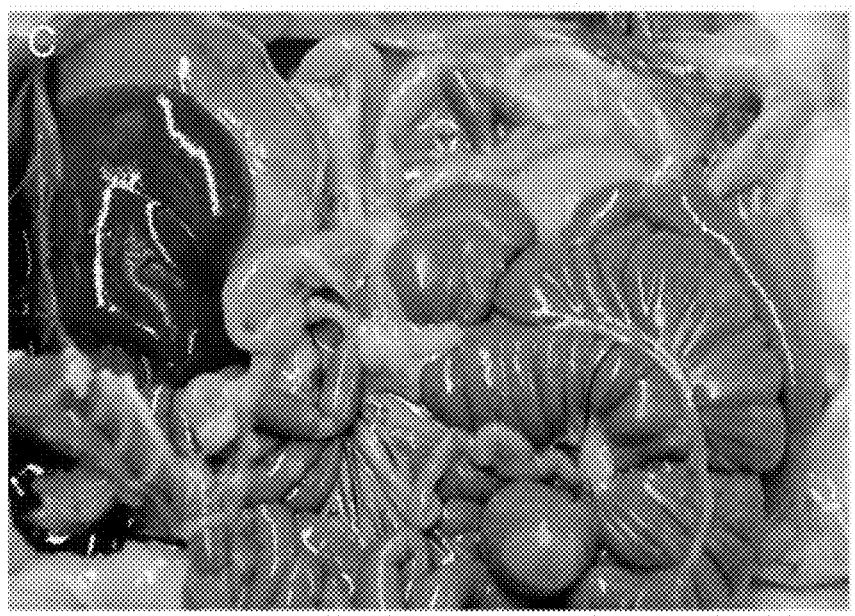
Figure 5D:
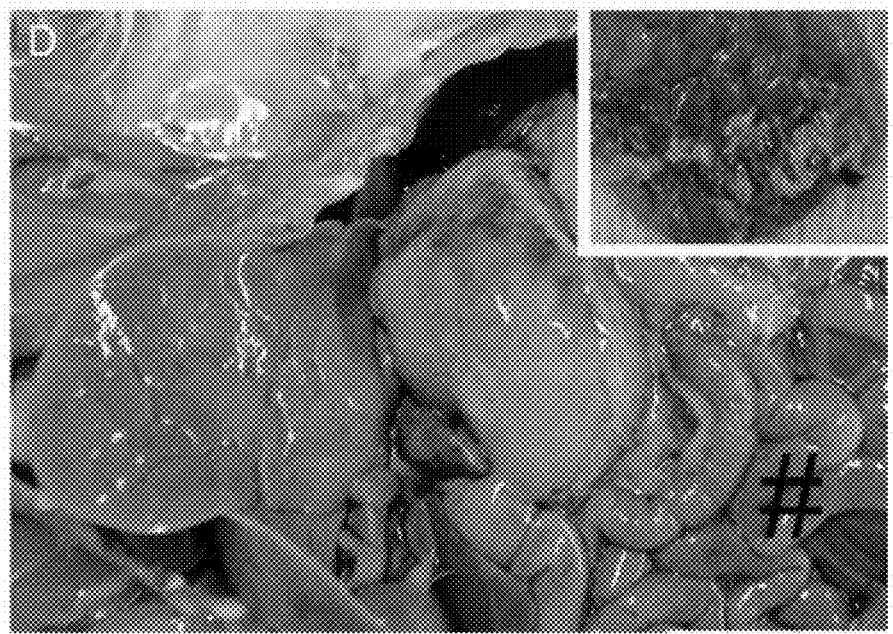
Figure 5E:
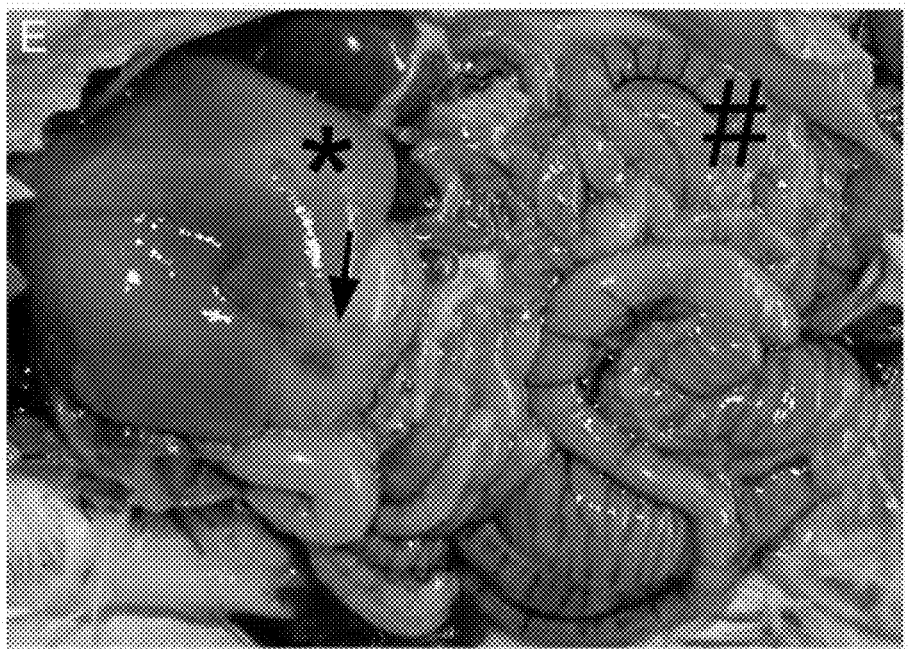
Figure 5F:
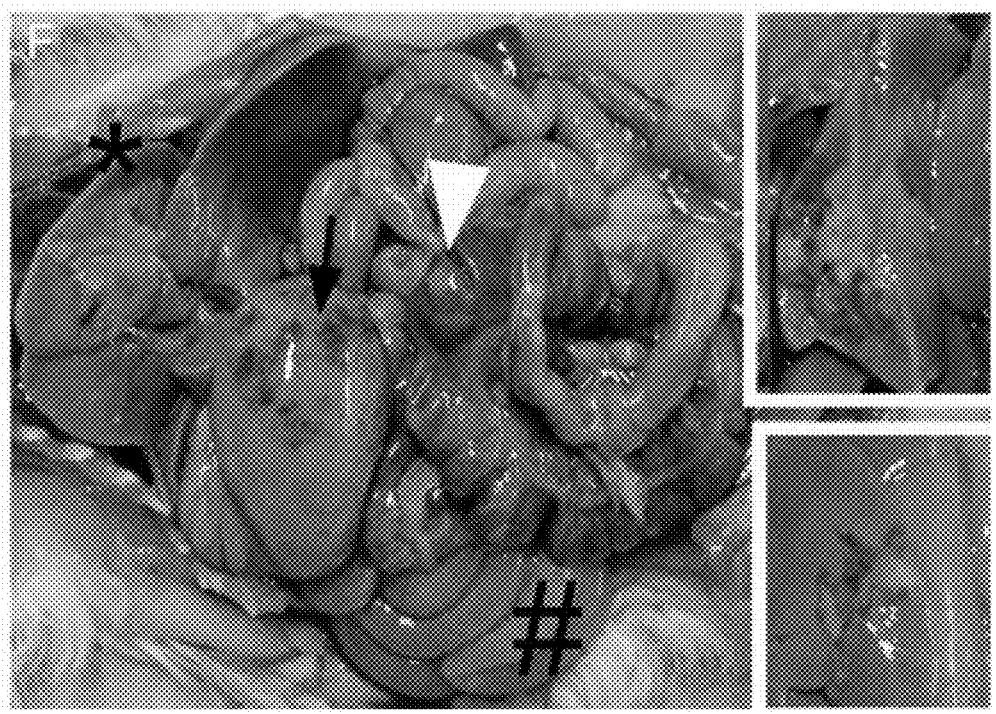
Figure 7A:
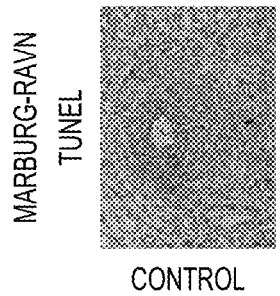
FIGS. 7A to 7A* shows the histopathology of spleen: MARV Rav Hemotoxylin & Eosin (H&E) (FIG. 7A, FIG. 7G, FIG. 7M, and FIG. 7S), corresponding anti-Marburg immunohistochemistry (IHC) (FIG. 7B, FIG. 7H, FIG. 7N, and FIG. 7T), and TUNEL staining (FIG. 7C, FIG. 7I, FIG. 7O, and FIG. 7U). MARV-Ang H&E, (FIG. 7D, FIG. 7J, FIG. 7P, and FIG. 7V), corresponding anti-Marburg IHC (FIG. 7E, FIG. 7K, FIG. 7Q, and FIG. 7W), and TUNEL staining (FIG. 7F, FIG. 7L, FIG. 7R, and FIG. 7X). Control GP H&E (FIG. 7Y) had no significant lesions (NSL), corresponding anti-Marburg IHC had no significant immunolabeling (FIG. 7Z), and TUNEL staining presented minimal immunolabeling in the white pulp (FIG. 7A*). All H&E and IHC spleen images are 40×. TUNEL staining images are 20×. Day 3 MARV-Rav-infected GP had NSL on H&E (FIG. 7A), diffuse cytoplasmic immunolabeling of mononuclear cells in the red pulp (FIG. 7B) with minimal TUNEL staining in the white pulp (FIG. 7C). Day 5 MARV-Rav-infected GP demonstrated evidence of lymphoid depletion with tingible body macrophages within the white pulp on H&E (FIG. 7G), diffuse cytoplasmic anti-Marburg immunolabeling of clustered mononuclear cells in the red and white pulp (FIG. 7H), accompanied by minimal TUNEL staining in the white pulp (FIG. 7I). Day 7 MARV-Rav-infected GP displayed evidence of marked lymphoid depletion, fibrin deposition, and tingible body macrophages within the white pulp on H&E (FIG. 7M), diffuse cytoplasmic anti-Marburg immunolabeling of mononuclear cells in the red and white pulp (FIG. 7N), and moderate TUNEL staining in the white pulp (FIG. 7O). Terminal MARV-Rav-infected GP lymphoid depletion, fibrin deposition, hemorrhage and tingible body macrophages within the white pulp on H&E (FIG. 7S), diffuse cytoplasmic anti-Marburg immunolabeling of scattered mononuclear cells in the red and white pulp (FIG. 7T), and marked TUNEL staining in the white pulp (FIG. 7U). Day 3 MARV-Ang-infected GP had NSL on H&E (FIG. 7D), diffuse cytoplasmic anti-Marburg immunolabeling of clustered mononuclear cells in the red and white pulp (FIG. 7E), and moderate TUNEL staining in the white pulp (FIG. 7F). Day 5 MARV-Ang-infected GP had evidence of lymphoid depletion with tingible body macrophages within the white pulp (FIG. 7J), diffuse cytoplasmic anti-Marburg immunolabeling of mononuclear cells in the red and white pulp (FIG. 7K), and moderate TUNEL staining in the white pulp (FIG. 7L). Day 7 MARV-Ang-infected GP lymphoid depletion, fibrin deposition, and tingible body macrophages within the white pulp on H&E (FIG. 7P), diffuse cytoplasmic anti-Marburg immunolabeling of mononuclear cells in the red and white pulp (FIG. 7Q), marked TUNEL staining in the white pulp (FIG. 7R). MARV-Ang-infected GP spleen, terminal (FIG. 7V) lymphoid depletion, fibrin deposition, hemorrhage, and tingible body macrophages within the white pulp, diffuse cytoplasmic anti-Marburg immunolabeling of scattered mononuclear cells in the red and white pulp (FIG. 7W), and marked immunolabeling in the white pulp (FIG. 7X). Abbreviations: GP, guinea pig; MARV, Marburg virus.
Figure 7Z:
Figure 7Y:

No gross lesions were present in the mock-infected control GPs (FIG. 5C). Gross lesions present at necropsy of both MARV-Rav-infected GPs and MARV-Ang-infected GPs appeared on day 3 and increased in severity over the course of the study. The most significant gross lesions included splenic mottling with enlargement, multifocal to diffuse hepatic pallor, lymphadenomegaly, and gastrointestinal congestion with ulceration (FIG. 5D-F). The severity of gastrointestinal and hepatic lesions in the terminal MARV-Ang-infected GPs (FIGS. 5D and 5F) were more prominent than those in the terminal MARV-Rav-infected GPs (FIG. 5E).

Hematologic Findings. Total and differential white blood cell counts for both strains of MARV elicited marked evidence of neutrophilia-mediated leukocytosis. Strikingly elevated circulating levels of neutrophils were noted beginning on 3 day and peaked on day 5 after infection for both strains. A concurrent marked lymphopenia was observed, as evidenced by declining mean lymphocyte counts. Thrombocytopenia, compared with control values, was marked, beginning at day 5 and continuing through terminal collection. Increases in mean platelet volume were also noted, beginning on day 5 and continuing through death for both infected groups. Basophilia and eosinophilia began on day 5 and progressed through death (Table 6).

TABLE 6

Results of Hematologic and Serum Biochemistry Analyses

| Parameter, Strain | Control | Day 1 | Day 3 | Day 5 | Day 7 | Terminal Time Point |
|---|---|---|---|---|---|---|
| Hematologic | | | | | | |
| WBC count, ×1000 cells/µL | 3.4 ± 1.6 | ... | ... | ... | ... | ... |
| Ravn | ... | 3.1 ± 1.2 | 2.6 ± 0.5 | 1.4 ± 0.5 | 3.2 ± 2.2 | 9.1 ± 1.6 |
| Angola | ... | 3.3 ± 1.2 | 2.8 ± 0.4 | 3.7 ± 1.9 | 5.2 ± 2.6 | 7.1 ± 4.4 |
| Neutrophils, % | 36.8 ± 7.2 | ... | ... | ... | ... | ... |
| Ravn | ... | 41.7 ± 3.9 | 60.3 ± 7.7 | 61.2 ± 6.9 | 53.9 ± 8.1 | 57.3 ± 7.6 |
| Angola | ... | 47.3 ± 10.7 | 60.7 ± 7.0 | 68.2 ± 10.2 | 50.9 ± 4.5 | 52.7 ± 4.0 |
| Lymphocytes, % | 59.3 ± 9.5 | ... | ... | ... | ... | ... |
| Ravn | ... | 55.8 ± 3.5 | 36.4 ± 8.1 | 31.8 ± 7.3 | 28.3 ± 4.0 | 29.8 ± 9.3 |
| Angola | ... | 46.3 ± 12.2 | 37.0 ± 6.0 | 26.7 ± 11.9 | 33.6 ± 2.8 | 34.1 ± 5.4 |
| Monocytes, % | 2.0 ± 0.9 | ... | ... | ... | ... | ... |
| Ravn | ... | 1.2 ± 0.5 | 1.3 ± 1.2 | 3.1 ± 2.0 | 1.6 ± 1.2 | 0.5 ± 0.3 |
| Angola | ... | 3.6 ± 2.5 | 2.0 ± 1.1 | 2.2 ± 0.5 | 1.5 ± 1.0 | 1.3 ± 0.7 |
| Eosinophils, % | 1.8 ± 1.6 | ... | ... | ... | ... | ... |
| Ravn | ... | 1.3 ± 1.4 | 2.0 ± 2.2 | 3.3 ± 1.4 | 12.8 ± 4.9 | 9.1 ± 1.8 |
| Angola | ... | 2.9 ± 2.6 | 0.2 ± 0.1 | 2.6 ± 2.8 | 11.3 ± 1.4 | 8.9 ± 2.8 |
| Basophils, % | 0 | ... | ... | ... | ... | ... |
| Ravn | ... | 0 | 0 | 0.6 ± 0.4 | 3.4 ± 1.8 | 3.4 ± 0.7 |
| Angola | ... | 0 | 0 | 0.4 ± 0.4 | 2.8 ± 0.6 | 3.0 ± 1.3 |
| Platelet count, ×1000 platelets/dL | 468.3 ± 23.7 | ... | ... | ... | ... | ... |
| Ravn | ... | 445.8 ± 69.0 | 390.0 ± 116.6 | 222.5 ± 65.5 | 187.8 ± 18.2 | 307.0 ± 83.5 |
| Angola | ... | 446.3 ± 74.6 | 469.3 ± 102.4 | 228.3 ± 93.9 | 153.8 ± 62.5 | 228.5 ± 83.6 |
| Mean platelet volume, fL | 5.4 ± 0.6 | ... | ... | ... | ... | ... |
| Ravn | ... | 5.7 ± 0.4 | 6.0 ± 0.4 | 10.6 ± 0.8 | 10.2 ± 6.9 | 13.1 ± 0.6 |
| Angola | ... | 5.8 ± 0.5 | 6.0 ± 0.4 | 9.9 ± 1.8 | 10.9 ± 2.2 | 13.2 ± 1.2 |
| Clinical | | | | | | |
| Albumin level, g/dL | 4.3 ± 0.2 | ... | ... | ... | ... | ... |
| Ravn | ... | 4.3 ± 0.4 | 4.1 ± 0.3 | 3.6 ± 0.1 | 3.0 ± 0.3 | 0.4 ± 0.5 |
| Angola | ... | 4.5 ± 0.1 | 4.3 ± 0.2 | 3.5 ± 0.3 | 1.2 ± 1.1 | 0.5 ± 0.1 |
| Total protein level, g/dL | 4.8 ± 0.1 | ... | ... | ... | ... | ... |
| Ravn | ... | 5.0 ± 0.6 | 5.0 ± 0.2 | 5.1 ± 0.2 | 4.8 ± 0.4 | 1.6 ± 0.7 |
| Angola | ... | 5.0 ± 0.3 | 4.9 ± 0.2 | 4.8 ± 0.3 | 2.7 ± 1.2 | 1.9 ± 0.1 |
| ALP level, U/L | 190.5 ± 28.3 | ... | ... | ... | ... | ... |
| Ravn | ... | 183.5 ± 31.1 | 155.8 ± 24.2 | 489.8 ± 126.9 | 1613.0 ± 937.5 | 1393.8 ± 688.4 |
| Angola | ... | 201.3 ± 16.9 | 187.3 ± 30.2 | 197.5 ± 59.7 | 1225.3 ± 381.5 | 1131.0 ± 208.7 |
| ALT level, U/L | 28.0 ± 5.9 | ... | ... | ... | ... | ... |
| Ravn | ... | 46.0 ± 10.1 | 31.3 ± 2.2 | 40.0 ± 8.0 | 80.0 ± 24.8 | 63.5 ± 34.9 |
| Angola | ... | 45.0 ± 13.7 | 40.3 ± 14.5 | 42.5 ± 12.0 | 55.5 ± 21.3 | 60.5 ± 21.7 |
| AST level, U/L | 84.8 ± 34.4 | ... | ... | ... | ... | ... |
| Ravn | ... | 100.0 ± 54.3 | 63.8 ± 14.0 | 239.3 ± 51.8 | 1228.0 ± 610.5 | 1030.3 ± 506.1 |
| Angola | ... | 115.3 ± 25.5 | 81.5 ± 17.8 | 201.8 ± 138.3 | 853.5 ± 285.7 | 692.0 ± 275.4 |
| GGT level, U/L | 7.0 ± 0.8 | ... | ... | ... | ... | ... |
| Ravn | ... | 7.3 ± 1.3 | 7.0 ± 0.8 | 14.5 ± 3.7 | 44.3 ± 22.3 | 35.8 ± 19.2 |
| Angola | ... | 7.0 ± 0.8 | 6.8 ± 1.0 | 11.3 ± 4.2 | 39.3 ± 14.7 | 24.3 ± 15.1 |
| Glucose level, mg/dL | 187.3 ± 57.5 | ... | ... | ... | ... | ... |
| Ravn | ... | 225.5 ± 41.8 | 216.3 ± 39.5 | 184.3 ± 3.5 | 226.5 ± 45.4 | 51.5 ± 29.9 |
| Angola | ... | 197.3 ± 45.8 | 211.8 ± 39.4 | 202.8 ± 36.8 | 118.0 ± 50.2 | 90.0 ± 19.6 |
| Amylase level, U/L | 1190.3 ± 129.0 | ... | ... | ... | ... | ... |
| Ravn | ... | 1550.0 ± 161.8 | 1000.0 ± 148.2 | 1016.0 ± 155.4 | 1342.3 ± 322.1 | 683.3 ± 304.0 |
| Angola | ... | 1379.8 ± 274.2 | 1075.8 ± 259.3 | 956.0 ± 195.3 | 901.0 ± 282.0 | 719.3 ± 117.4 |
| TBIL level, mg/dL | 0.3 ± 0.1 | ... | ... | ... | ... | ... |
| Ravn | ... | 0.3 ± 0.0 | 0.3 ± 0.1 | 0.3 ± 0.1 | 0.6 ± 0.3 | 0.5 ± 0.2 |
| Angola | ... | 0.3 ± 0.1 | 0.3 ± 0.0 | 0.3 ± 0.1 | 1.0 ± 0.6 | 1.3 ± 0.5 |
| BUN level, mg/dL | 16.5 ± 0.6 | ... | ... | ... | ... | ... |
| Ravn | ... | 15.8 ± 2.1 | 13.8 ± 1.9 | 10.8 ± 1.3 | 27.8 ± 15.2 | 33.3 ± 16.3 |
| Angola | ... | 17.5 ± 0.6 | 15.5 ± 2.4 | 11.8 ± 0.5 | 15.0 ± 8.2 | 15.5 ± 6.5 |

Abbreviations:
ALP, alkaline phosphatase;
ALT, alanine transaminase;
AST, aspartate transaminase;
BUN, blood urea nitrogen;
GGT, γ-glutamyl transpeptidase;
TBIL, total bilirubin;
WBC, white blood cells.

Figure 8B:
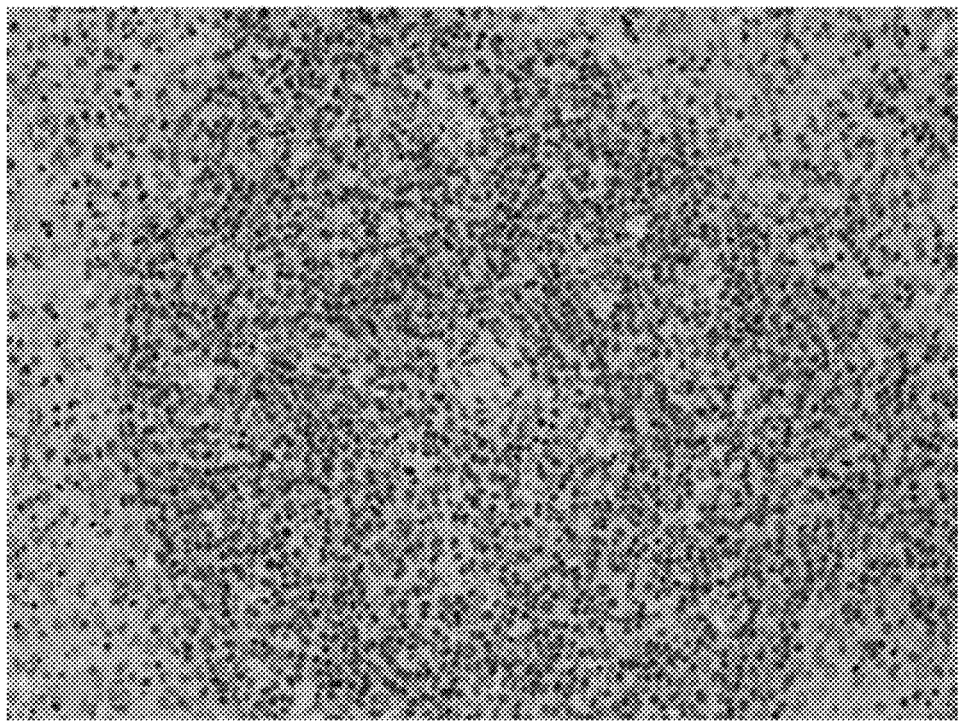
Figure 8A:
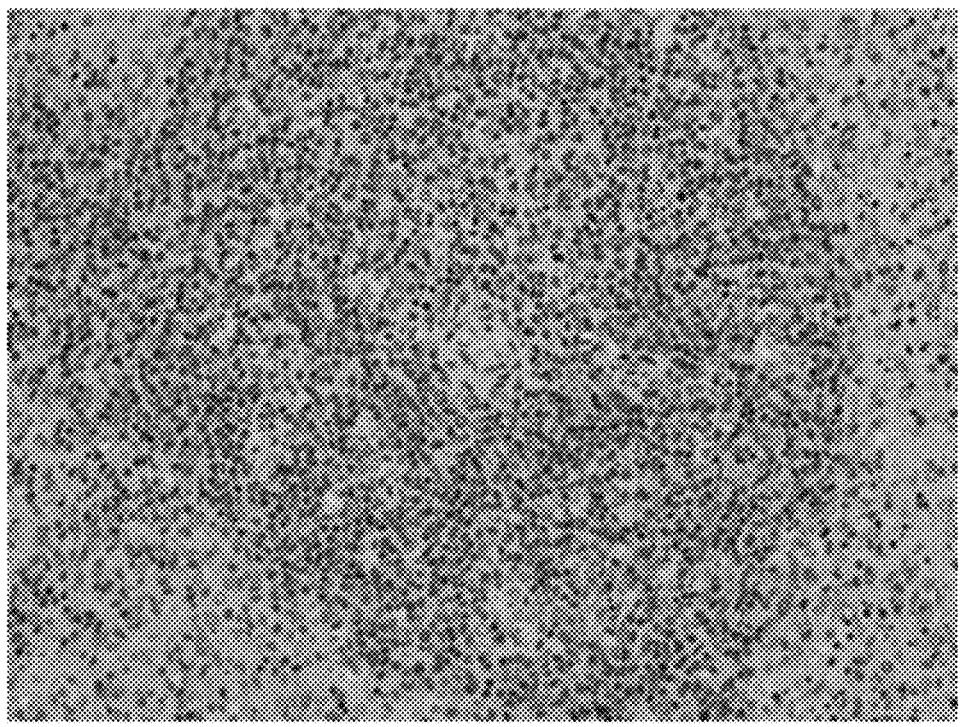
Figure 8C:
Figure 8D:
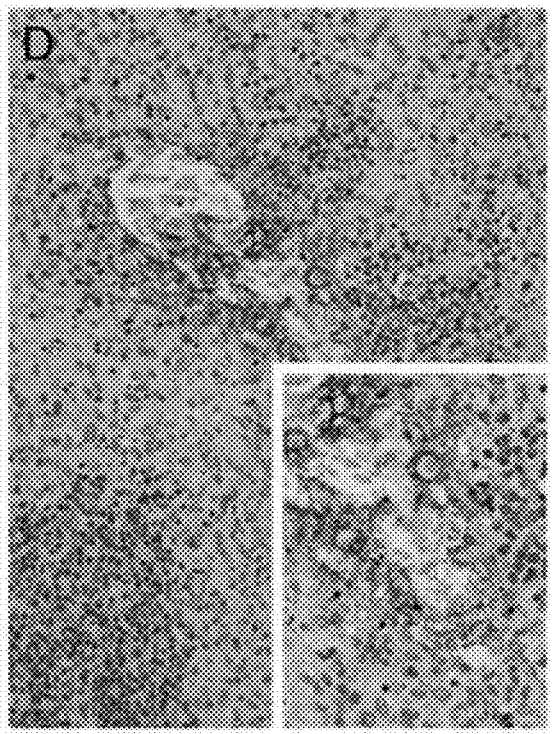

Serum Biochemistry Findings. No remarkable changes were noted in early serum enzyme levels but most were elevated in late disease. Beginning day 7 and continuing to death, remarkable 10-fold increases in circulating levels of aspartate transaminase and alkaline phosphatase were present in both MARV strains. More-modest increases in levels of alanine transaminase (approximately 2.5-fold) and gammaglutamyl transpeptidase (approximately 6-fold) were detected at late-stage disease. The total bilirubin level was within normal limits until day 7, after which it doubled in MARV-Rav-infected animals and tripled in MARV-Ang-infected animals at termination time points. Blood urea nitrogen levels remained consistent throughout infection in MARV-Ang-infected animals; however, a 2-fold increase was observed at final time points in MARV-Rav-infected animals. Hypoalbuminemia with concurrent hypoproteinemia began on day 5 (Table 3).

Histopathologic and Immunohistochemistry Findings. Histopathologic lesions and immunoreactivity for MARV antigen in tissues of MARV-infected GPs were most apparent by day 3, with the severity of the lesions increasing over the duration of the study. MARV antigen associated with histologic lesion severity was similar between both MARV-Rav-infected animals and MARV-Ang-infected animals; however, infection by cell type was different, with obvious progression of up to 2 days sooner in the MARV-Ang group, compared with the MARV-Rav group. No significant histopathologic lesions, presence of viral antigen, or abnormal fibrin was observed in mockinfected control GP tissues.

Liver. Beginning on day 3, MARV antigen-positive Kupffer cells were observed for both MARV-Rav-infected GPs (3 of 4; FIG. 6B) and MARV-Ang-infected GPs (4 of 4; FIG. 6D). Additionally, minimal individualized hepatocytes (MARV-Rav-infected GPs) and small clusters of adjacent hepatocytes (MARVAng-infected GPs) had immunoreactivity. Lesions on hematoxylin and eosin (H/E)-stained sections associated with MARV antigen were detected on day 3, with hepatocellular degeneration/necrosis and sinusoidal leukocytosis in 3 of 4 MARV-Rav-infected GPs and 4 of 4 MARV-Ang-infected GPs. The prevalence of MARV antigen-positive Kupffer cells and clusters of hepatocytes increased throughout the study for both MARV-Rav-infected GPs (12 of 12) and MARV-Ang-infected GPs (12 of 12). Progressive hepatocellular vacuolation, degeneration/necrosis with mineralization, and sinusoidal leukocytosis on H/E-stained sections corresponded with MARV antigen in all GP livers on day 5, day 7, and in terminal groups (12 of 12 in the MARV-Rav group and 12 of 12 in the MARVAng group). Councilman-like bodies were occasionally observed on day 5 in 2 of 4 MARV-Rav-infected GPs and 4 of 4 MARV-Ang-infected GPs and on day 7 in 1 of 4 MARVRav-infected GPs and 2 of 4 MARV-Ang-infected GPs (FIGS. 6H and 6E). Beginning on day 1 and progressing through death, MARV-Rav-infected animals displayed an earlier onset of marked increases in nuclear and cytoplasmic expression of high-mobility group B1 (HMGB-1) in Kupffer cells and hepatocytes as compared to MARV-Ang-infected GPs and control animals (data not shown).

Spleen. On day 3, MARV antigen-positive mononuclear/dendritiform cells were observed for both MARV-Rav-infected GPs (3 of 4) and MARV-Ang-infected GPs (4 of 4; FIGS. 7B and 7E). Key differences on day 3 were immunoreactive cells scattered throughout the red pulp only for MARV-Rav-infected GPs and small clusters of immunoreactive cells within the red and white pulp for MARV-Ang-infected GPs. Corresponding congestion and tingible body macrophages were noted on H/Estained sections of spleens from both MARV-Rav-infected GPs and MARV-Ang-infected GPs. Immunoreactive cells within the spleen peaked at day 3 for MARV-Ang-infected GPs (FIG. 7E) and by day 5 for MARV-Rav-infected GPs (FIG. 7H), with dispersion of MARV antigen-positive cells throughout the spleen by the end of the study. All animals, beginning on day 3 and continuing to death, had progressive lymphocyte depletion with tingible body macrophages, hemorrhage, and fibrin deposition within the white pulp. TUNEL staining of apoptotic populations within the splenic germinal centers increased over time, with peak intensity on day 5 for MARV-Ang-infected GPs (FIG. 7L) and in terminal specimens for MARV-Rav-infected GPs (FIG. 7U). Fibrin was scattered throughout the red pulp and clustered within the white pulp in MARV-Rav-infected GPs (FIG. 8B). Fibrin immunolabeling of strands and aggregates within vessels, along the endothelium, and in clusters that disperse into the adjacent red and white pulp were present in MARV-Ang-infected GPs (FIGS. 8C and 8D).

Lymphoid Tissues. Beginning on day 5 and increasing in severity to the end of the study, lymphoid depletion was observed in mandibular (10 of 12 MARV-Rav-infected GPs and 11 of 12 MARV-Ang-infected GPs), axillary (8 of 12 and 8 of 12, respectively), and inguinal (8 of 12 and 8 of 12, respectively) lymph nodes. MARV antigen was noted in scattered mononuclear cells within the subcapsular and medullary sinuses of lymph nodes for both MARV-Rav and MARV-Ang groups. TUNEL staining of apoptotic populations within the mandibular lymph nodes increased over time, with peak intensity on day 5 for MARV-Ang-infected GPs and day 7 for MARV-Rav-infected GPs.

Adrenal Gland. MARV antigen-positive interstitial cells of the adrenal medulla were present in 4 of 4 MARV-Ang-infected GPs on day 3 and 4 of 4 MARV-Rav-infected GPs on day 5, yet no significant lesions were observed on H/E-stained sections. Subsequently, infection progressively extended into the interstitial cells of the cortex and cortical cells until death for both the MARV-Rav group (12 of 12 GPs) and the MARV-Ang group (12 of 12 GPs). Beginning on day 7, hemorrhage at the corticomedullary junction corresponded with immunoreactivity for both MARV-Rav-infected GPs (7 of 8) and MARV-Ang-infected GPs (7 of 8).

Lung. MARV antigen-positive alveolar macrophages and mononuclear cells within alveolar septae were observed on day 7 and at terminal time points for both MARV-Rav-infected GPs (7 of 8) and MARV-Ang-infected GPs (8 of 8), which corresponded with interstitial pneumonia (data not shown).

Urogenital Tract. Beginning on day 7, MARV antigen was observed in submucosal interstitial cells and the transitional epithelium of the urinary bladder in MARV-Rav-infected GPs (3 of 8) and MARV-Ang-infected GPs (4 of 8). Lymphohistiocytic vasculitis of the urinary bladder submucosa was present in terminal specimens from MARVRav-infected animals, yet no lesions were noted in MARVAng-infected GPs. MARV antigen-positive mononuclear interstitial cells within the uterus, often surrounding small vessels and follicular thecal cells, were present at terminal time points of both MARV-Rav-infected GPs (2 of 2) and MARVAng-infected GPs (2 of 2), yet no significant lesions were observed on H/E-stained sections (data not shown).

Gastrointestinal Tract. A focal gastric ulceration was noted in a terminal specimen from 1 MARV-Ang GP. Beginning on day 7, with progression to death, lymphoid depletion in MARV-Rav GPs was noted in the thymus (7 of 8 animals), ileocecal junction (8 of 8), and duodenum (8 of 8); similar findings were also observed in MARVAng-infected GPs (8 of 8, 8 of 8, and 6 of 8, respectively). TUNEL staining of apoptotic populations within the lamina propria of the duodenum at death of a MARV-Ang-infected GP was most striking, extending from the villar tips to the submucosa, compared with that of a MARV-Rav-infected GP, which extended approximately one fourth of the way down the villar tip (data not shown).

Coagulation Parameters. Prothrombin times began to extend significantly beginning at day 3 and continued to lengthen throughout the course of disease. Activated partial thromboplastin times (APTTs) were not extended until late in disease, beginning on day 7. Beginning on day 1, decreases in thrombin times corresponded with increases in fibrinogen content throughout the disease course. Circulating protein C activity and tissue factor levels progressively decreased; however, plasminogen activator inhibitor 1 (PAI-1) and von Willebrand factor levels were markedly increased in late disease. The mean thrombin-activated fibrinolysis inhibitor (TAFI) level began to increase markedly on day 3 in MARV-Rav-infected GPs and stayed elevated through death. Conversely, MARVAng-infected GPs did not have an increased mean level of TAFI until late in disease. Interestingly, circulating tissue factor levels decreased gradually until the time of death. Bradykinin levels gradually increased to approximately 6-fold higher than those in control animals at late points in disease. Conversely, prekallikrein levels were severely depressed until late in the disease course, when, at day 7, a striking increase was recorded in MARV-Ang-infected GPs but not in MARV-Rav-infected animals. Circulating levels of thrombin in complex with thrombomodulin were noted beginning on day 1 and increased throughout the disease course for both strains (FIGS. 8E-1 to 8E-3).

Circulating Eicanosoid, Cytokine, and Nitric Oxide Production Mean levels of prostaglandin E2 began to decrease on day 1, with a continued decrease to day 3. Beginning on day 5, however, marked increases were noted in mean values, with the terminal mean value approximately 3 times that of control animals. The mean leukotriene B4 value was elevated in MARVAng animals on day 1 and tended to increase over the disease course to approximately 4 times the level in control animals. MARV-Rav-infected animals demonstrated a similar trend, beginning on day 3, but with comparatively muted mean levels. Mean cysteinal leukotriene levels gradually increased throughout the course of infection, beginning on day 5. Thromboxane B2 levels were elevated in MARV-Rav-infected animals beginning on day 3 and continuing through terminal time points; conversely, MARV-Ang-infected animals did not have significant difference in levels of this eicansoid. Prostacyclin levels were measured via the stable metabolite 6-keto-prostaglandin F1a and were first elevated in MARV-Rav-infected animals beginning on day 3; MARV-Ang-infected animals demonstrated a marked increase on day 5. Transforming growth factor (3, interleukin 6, and tumor necrosis factor α values were marked late in disease through death. Very soon after infection, mean levels of HMGB-1 were higher in MARV-Rav-infected GPs, compared with MARVAng-infected GPs, yet both were markedly elevated as compared to those in control animals throughout the study. Circulating nitrite levels were increased in both species, beginning on day 5; however, striking increases were recorded in MARV-Ang-infected animals in late disease (FIGS. 8E-1 to 8E-3).

The increased frequency and severity of filovirus outbreaks in recent years underscores the dire need for medical countermeasures. The development of rodent models that faithfully represent MHF processes yet maintain predictive power for filovirus-specific countermeasures could facilitate scale up of screening efforts of these medical interventions and thereby restrict precious primate resources to only the most likely candidate countermeasures. Inbred rodent models are commonly used to model a variety of disease processes but have limitations in regard to their well-documented depressed immune capacity. This caveat is a major shortcoming for vaccines and therapeutic development, which maintain heavy reliance on various aspects of host immunity for efficacy. To further complicate the issue, limited descriptions of coagulopathies or vascular leak in rodent models of MHF exist, thereby limiting the power of these models.

To address the need for improved rodent models, the present inventors developed two outbred GP models that demonstrate not only hallmark features of MHF, but also provide systematic evidence for differences in pathogenicity among phylogenetically diverse MARV strains. Both models recapitulate important aspects of NHP and human MHF pathogenic features, including fever, weight loss, and early infection of macrophage/dendritiform cells, followed by remarkable splenic and hepatic pathology, lymphocyte apoptosis, neutrophilia, thrombocytopenia, and marked granulocytosis. Perturbations in serum biochemistry findings in NHP and human MHF were also similar, specifically in regard to marked increases in liver-associated enzyme levels, proinflammatory cytokine levels, nitric oxide species and hypoalbuminemia. This work also details a severe coagulopathy, which includes increased prothrombin and APTTs, decreased thrombin times, decreased protein C activity, marked fibrinogen deregulation, increased prostacyclin, thromboxane, von Willebrand factor, PAI-1, and circulating thrombin-thrombomodulin complex levels, and deposition of fibrin in tissues, all of which have been demonstrated in MHF in NHPs and humans [15-19]. Decreased serum tissue factor was also documented.

Given the similarities in pathogenesis between viral hemorrhagic fever and sepsis [21, 22], the inventors probed this model for several pathologically relevant phenomena that are important in bacterial sepsis. The inventors detected evidence for activation of the kallikrein-kinin system and disruption of fibrinolysis processes, as evidenced by abrogated bradykinin, prekallikrein, and TAFI metabolism. Deregulation of circulating eicanosoids has also been associated with sepsis [23, 24]. Accordingly, the inventors documented deregulation of several important species of prostaglandins and leukotrienes late in disease. Recent work in sepsis has also suggested the importance of proinflammatory cytokine/transcription factor HMGB-1 in disease severity [25, 26]. These data suggest a role for this molecule in early MHF that may lend to differences in pathogenesis between MARV strains. Prior work with the Musoke strain of MARV identified several mutations necessary for lethality in strain 13 GPs; however, sequencing of the GPA MARVs from this work revealed multiple changes, of which none had been previously described [27]. Both MARV strains adopted genetic mutations that resulted in amino acid changes within the VP40 proteins; however, only MARV-Ang had changes in VP24, a protein recognized to be important in formation of infectious particles and interaction with cytoprotective antioxidant response pathways [28, 29]. Given the higher viral burden in tissues and plasma, marked increases in severe inflammation, and shorter mean time to death, this finding suggests that VP24 is a potential molecular landmark responsible for virulence differences between MARV species. The recently developed reverse genetics system for MARV will allow for a more mechanistic approach to identify which mutations directly contribute to pathogenesis in these models [30, 31]. This study represents the first systematic pathogenesis study of MARV strains in vivo and demonstrates the need for strain consideration when developing countermeasures against MARV.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Field of Invention," such claims should not be limited by the language under this heading to describe the so-called technical field. Further, a description of technology in the "Background of the Invention" section is not to be construed as an admission that technology is prior art to any invention(s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A uniformly lethal MARV-Angola Filovirus strain adapted for virulence in a small mammal, wherein the original strain has the nucleotide/amino acid sequence of Mary Angola isolate Ang1379c having the GenBank Accession No. DQ447653, that comprises all of the following mutations:

| Nucleotide | Base Change | Result | Gene |
| --- | --- | --- | --- |
| 2931 | U > A |  | Non-coding |
| 4735 | U > A | N56K | VP40 |
| 10402 | G > A | V66I | VP24 |
| 10853 | U > C | L216S | VP24 |
| 13115 | U > C | Silent | L |
| 17249 | U > A | Silent | L |

-continued

| Nucleotide | Base Change | Result | Gene |
|---|---|---|---|
| 18713 | C > A | | Non-coding; and |
| 19105 | A > U | | Non-coding. |

* * * * *